(12) United States Patent
Zettl et al.

(10) Patent No.: US 11,028,169 B2
(45) Date of Patent: Jun. 8, 2021

(54) ANTIBODY MOLECULES FOR CANCER TREATMENT

(71) Applicant: Boehringer Ingelheim International GmbH, Ingelheim am Rhein (DE)

(72) Inventors: Markus Zettl, Vienna (AT); Ivo Lorenz, Brooklyn, NY (US); Otmar Schaaf, Vienna (AT); Melanie Wurm, Vienna (AT); Jean-Francois Fortin, Laval (CA); Scott Ronald Brodeur, New Hope, PA (US); Keith A. Canada, Freehold, NJ (US); Lukasz Chlewicki, Indianapolis, IN (US); Priyanka Gupta, Danbury, CT (US); Rocío K. Pérez, Danbury, CT (US); Joseph Robert Woska, Yorktown Heights, NY (US); Haiguang Xiao, Ridgefield, CT (US); Danlin Yang, Bethel, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/598,356

(22) Filed: May 18, 2017

(65) Prior Publication Data

US 2017/0334995 A1    Nov. 23, 2017

(30) Foreign Application Priority Data

May 18, 2016   (EP) .................................... 16170174

(51) Int. Cl.
| | | |
|---|---|---|
| A61K 39/00 | (2006.01) | |
| C07K 16/28 | (2006.01) | |
| A61K 39/395 | (2006.01) | |
| A61K 45/06 | (2006.01) | |

(52) U.S. Cl.
CPC ...... *C07K 16/2803* (2013.01); *A61K 39/3955* (2013.01); *A61K 45/06* (2013.01); *C07K 16/2818* (2013.01); *C07K 16/2827* (2013.01); *A61K 2039/505* (2013.01); *A61K 2039/507* (2013.01); *C07K 2317/24* (2013.01); *C07K 2317/34* (2013.01); *C07K 2317/73* (2013.01); *C07K 2317/76* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | |
|---|---|---|
| 5,624,821 A | 4/1997 | Winter et al. |
| 5,648,260 A | 7/1997 | Winter et al. |
| 2016/0376367 A1 | 12/2016 | Yuan et al. |

FOREIGN PATENT DOCUMENTS

| | | |
|---|---|---|
| EP | 388151 A1 | 9/1990 |
| JP | 2013521769 A | 6/2013 |
| WO | 88/01649 A1 | 3/1988 |
| WO | 90/05144 A1 | 5/1990 |
| WO | 91/17271 A1 | 11/1991 |
| WO | 94/04678 A1 | 3/1994 |
| WO | 94/13804 A1 | 6/1994 |
| WO | 94/29348 A2 | 12/1994 |
| WO | 98/25971 A1 | 6/1998 |
| WO | 98/48837 A1 | 11/1998 |
| WO | 2002056910 A1 | 7/2002 |
| WO | 2004003019 A2 | 1/2004 |
| WO | 2004041865 A2 | 5/2004 |
| WO | 2004081026 A2 | 9/2004 |
| WO | 2010019570 A2 | 2/2010 |
| WO | 2011110621 A1 | 9/2011 |
| WO | 2014008218 A1 | 1/2014 |
| WO | 2014140180 A1 | 9/2014 |
| WO | 2014179664 A2 | 11/2014 |
| WO | 2015042246 A1 | 3/2015 |
| WO | 2015069571 A1 | 5/2015 |
| WO | 2015085847 A1 | 6/2015 |
| WO | 2015138920 A1 | 9/2015 |
| WO | 2016028672 A1 | 2/2016 |
| WO | 2016057846 A1 | 4/2016 |
| WO | 2016061142 A1 | 4/2016 |
| WO | 2016092419 A1 | 6/2016 |
| WO | 2016168716 A1 | 10/2016 |
| WO | 2016200782 A1 | 12/2016 |
| WO | 2017062888 A1 | 4/2017 |

OTHER PUBLICATIONS

Li et al. (J. Immunol. Dec. 1, 2004; 173 (11): 6806-12).*
Jiang et al. (J. Biol. Chem. Feb. 11, 2005; 280 (6): 4656-4662).*
Riemer et al. (Mol. Immunol. 2005; 42: 1121-1124).*
Holmes (Expert Opinion on Investigational Drugs. 2001; 10: 511-9).*
Shukuya, Takehito et al. "Predictive Markers for the Efficacy of Anti-PD-1/PDI-L1 Antibodies in Lung Cancer" (2016) Journal of Thoracic Oncology, vol. 11, No. 7, 976-988.
International Search Report for PCT/EP2017/061901 dated Sep. 15, 2017. 22 pgs.
U.S. Appl. No. 16/871,382, filed May 11, 2020. Inventor: Markus Zettl.
Altschul, Stephen F et al. "Basic local alignment search tool" (1990) Journal of Molecular Biology, vol. 215, Issue 3, 403-410 (Abstract only).

(Continued)

*Primary Examiner* — Stephen L Rawlings
(74) *Attorney, Agent, or Firm* — Edouard G. Lebel

(57) ABSTRACT

The present invention relates to novel anti-PD1 and anti-LAG3 antibody molecules. The invention also relates to nucleic acids encoding such antibody molecules; to methods for preparing such antibody molecules; to host cells expressing or capable of expressing such antibody molecules; to compositions comprising such antibody molecules; and to uses of such antibody molecules or such compositions, in particular for therapeutic purposes in the field of cancer diseases.

67 Claims, 23 Drawing Sheets

Specification includes a Sequence Listing.

(56) References Cited

OTHER PUBLICATIONS

Altschul, Stephen F. et al. "Gapped Blast and PSI-Blast: a new generation of protein database search programs" (1997) Nucleic Acids Research, vol. 25, No. 17, 3389-3402.
Barbas III, Carlos F. et al. "In vitro evolution of a neutralizing human antibody to human immunodeficiency virus type 1 to enhance affinity and broaden strain cross-reactivity" (1994) PNAS, vol. 91, 3809-3813.
Billetta, Rosario, et al. "Chimeric Antibodies" (1993) International Reviews of Immunology, vol. 10, 165-176.
Bruggemann, Marianne et al. "Production of human antibody repertoires in transgenic mice" (1997) Current Opinion in Biotechnology, 8: 455-458.
Darmen, Sara et al. "Concepts in antibody phage display" (2002) Briefing in Functional Genomics and Proteomics, vol. 1, No. 2, 189-203.
Chothia, Cyrus et al. "Canonical Structures for the Hypervariable Regions of Immunoglobins" (1987) J. Mol. Biol., vol. 196, 901-917.
Cole, S.P.C. et al. "Human monoclonal antibodies" (1984) Molecular and Cellular Biochemistry, 62, 109-120.
Cote, Richard J. et al. "Generation of human monoclonal antibodies reactive with cellular antigens" PNAS, (1983) vol. 80, 2026-2030.
Higgins, Desmond G. et al. "Using Clustal for Multiple Sequence Alignments" (1996) Methods in Enzymology, vol. 266, 383-402.
Holliger, Philipp et al. ""Diabodies": Small bivalent and bispecific antibody fragments" (1993) Proc. Natl. Acad. Sci., vol. 90, 6444-6448.
Huston, James S. et al. "Medical Applications of Single-Chain Antibodies" (1993) Intern. Rev. Immunol., vol. 10, 195-217.
Karlin, Samuel et al. "Applications and statistics for multiple high-scoring segments in molecular sequences" (1993) PNAS, vol. 90, 5873-5877.
Karlin, Samuel et al. "Methods for assessing the statistical significance of molecular sequence features by using general scoring schemes" (1990) PNAS, vol. 87, 2264-2268.
Kipriyanov, S.M. et al. "Recent advances in the generation of bispecific antibodies for tumor immunotherapy" (2004) Current Opinion Drug Discovery Development, vol. 2, 233-242, (Abstract only).
Knappik, Achim et al. "Fully Synthetic Human Combinatorial Antibody Libraries (HuCAL) Based on Modular Consensus Frameworks and CDRs Randomized with Trinucleotides" (2000) 296, 57-86.
Kohler, G. et al. "Continuous cultures of fused cells secreting antibody of predefined specificity" (1975) Nature, 256, 195-497 (Abstract only).
Kozbor, D. et al. "Specific Immunoglobulin Production and Enhanced Tumorigenicity Following Ascites Growth of Human Hybridomas" (1985) Journal of Immunological Methods, vol. 81, 31-42.
Lonberg, Nils et al. "Human Antibodies from Transgenic Mice" (1995) International Reviews of Immunology, vol. 13, 35-93, (Abstract only).

Marks, James D. et al. "By-passing Immunization Human Antibodies from V-gene Libraries Displayed on Phage" (1991) J. Mol. Biol., vol. 222, 581-597.
Marks, James D. et al. "By-Passing Immunization: Building High Affinity Human Antibodies by Chain Shuffling" (1992) Biotechnology, vol. 10, 779-783, (Abstract only).
Myers, Eugene W. et al. "Optimal alignments in linear space" (1988) CABIOS, vol. 4, No. 1, 11-17.
Norderhaug, Lars et al. "Versatile vectors for transient and stable expression of recombinant antibody molecules in mammalian cells" (1997) 204, 77-87.
Orlandi, Rosana et al. "Cloning immunoglobulin variable domains for expression by the polymerase chain reaction" (1989) PNAS, vol. 86, 3833-3837.
Pearson, William R. et al. "Improved tools for biological sequence comparison" (1988) PNAS, vol. 85, 2444-2448.
Revets, Ride et al. "Nanobodies as novel agents for cancer therapy" (2005) Expert Opinion on Biological Therapy, vol. 5, 111-124 (Abstract only).
Riechmann, Lutz et al. "Reshaping human antibodies for therapy" (1998) Nature, vol. 332, 323-327.
Rippmann, Jorg F. et al. "Procaryotic Expression of Single-Chain Variable -Fragment (scFv) Antibodies: Secretion in L-Form Cells of Proteus mirabilis Leads to Active Product and Overcomes the Limitations of Periplasmic Expression in *Escherichia coli*" (1998) Applied and Enviromental Microbiology, vol. 64, No. 12, 4862-4869.
Schier, Robert et al. "Identification of functional and structural amino-acid residues by parsimonious mutagenesis" (1996) Gene, 147-155.
Shukla, Abhinav A. et al. "Downstream processing of monoclonal antibodies—Application of platform approaches" (2007) Journal of Chromatography B, 848, 28-39.
Sonoda, Hiroyuki et al. "Functional expression of single-chain Fv antibody in the cytoplasm of *Escherichia coli* by thioredoxin fusion and co-expression of molecular chaperones" (2010) Protein Expression and Purification, vol. 70, 248-253.
Srinivasan, Mythily et al. "Immunomodulatory Peptides from IgSF Proteins: A Review" (2005) Current Protein & Peptide Science, vol. 6, Issue 2, (Abstract only).
Torelli, Alberto et al. "Advance and Adam: two algorithms for the analysis of global similarity between homologous informational sequences" (1994) Cabios, vol. 10, No. 1, 3-5.
Wang, Changyu et al. "In Vitro Characterization of the Anti-PD-1 Antibody Nivolumab, BMS-93655, and In Vivo Toxicology in Non-Human Primates" Cancer Immunology Research (2014) 846-856.
Ward, E. Sally et al. "Binding activites of a repertoire of single immunoglobulin variable domains secreted from *Escherichia coli*" (1989) Letters to Nature, vol. 341, 544-546.
Winter, Greg et al. "Man-made antibodies" (1991) Nature, vol. 349, 293-299.
Yamawaki, Shinya et al. "Production of Single-Chain Variable Fragment Antibody (scFv) in Fed-Batch and Continuous Culture in Pichia pastoris by Two Different Methanol Feeding Methods" (2007) Journal of Bioscience and Bioengineering, vol. 104, No. 5, 403-407.

\* cited by examiner

A – VK SEQUENCES

77E11　DIVLTQSPASLAVSLGQRATMSC<u>RASENIDNSGISFMN</u>WFQQKPGQPPKLLIY

PD1-1　EIVLTQSPATLSLSPGERATMSC<u>RASENIDTSGISFMN</u>WYQQKPGQAPKLLIY

PD1-2　EIVLTQSPATLSLSPGERATMSC<u>RASENIDTSGISFMN</u>WYQQKPGQAPKLLIY

PD1-3　EIVLTQSPATLSLSPGERATMSC<u>RASENIDVSGISFMN</u>WYQQKPGQAPKLLIY

PD1-4　EIVLTQSPATLSLSPGERATMSC<u>RASENIDVSGISFMN</u>WYQQKPGQAPKLLIY

PD1-5　EIVLTQSPATLSLSPGERATMSC<u>RASENIDVSGISFMN</u>WYQQKPGQAPKLLIY (B)

A – VK SEQUENCES

77E11　<u>VASNQGSGV</u>PARFSGSGSGTDFRLTIHPLEEDDTAMYFC<u>QQSKEVPWT</u>FGGGTKLEIK

PD1-1　<u>VASNQGSGI</u>PARFSGSGSGTDFTLTISRLEPEDFAVYYC<u>QQSKEVPWT</u>FGQGTKLEIK

PD1-2　<u>VASNQGSGI</u>PARFSGSGSGTDFTLTISRLEPEDFAVYYC<u>QQSKEVPWT</u>FGQGTKLEIK

PD1-3　<u>VASNQGSGI</u>PARFSGSGSGTDFTLTISRLEPEDFAVYYC<u>QQSKEVPWT</u>FGQGTKLEIK

PD1-4　<u>VASNQGSGI</u>PARFSGSGSGTDFTLTISRLEPEDFAVYYC<u>QQSKEVPWT</u>FGQGTKLEIK

PD1-5　<u>VASNQGSGI</u>PARFSGSGSGTDFTLTISRLEPEDFAVYYC<u>QQSKEVPWT</u>FGQGTKLEIK

B – VH SEQUENCES

```
77E11  EVMLVESGGGLVKPGGSLKLSCTASGFTFSNSAMSWVRQTPERRLEWVA
PD1-1  EVMLVESGGGLVQPGGSLRLSCTASGFTFSASAMSWVRQAPGKGLEWVA
PD1-2  EVMLVESGGGLVQPGGSLRLSCTASGFTFSASAMSWVRQAPGKGLEWVA
PD1-3  EVMLVESGGGLVQPGGSLRLSCTASGFTFSKSAMSWVRQAPGKGLEWVA
PD1-4  EVMLVESGGGLVQPGGSLRLSCTASGFTFSKSAMSWVRQAPGKGLEWVA
PD1-5  EVMLVESGGGLVQPGGSLRLSCTASGFTFSKSAMSWVRQAPGKGLEWVA
```

(B)

B – VH SEQUENCES

```
77E11  YISGGGGDTYYSDSVKGRFTISRDNAKDTLYLHMSSLRSEDTALHYCARHSNSNYYAMDYWGQGTSVTVSS
PD1-1  YISGGGGDTYYSSSVKGRFTISRDNAKNSLYLQMNSLRAEDTAVYYCARHSNVNYYAMDYWGQGTLVTVSS
PD1-2  YISGGGGDTYYSSSVKGRFTISRDNAKNSLYLQMNSLRAEDTAVYYCARHSNPNYYAMDYWGQGTLVTVSS
PD1-3  YISGGGGDTYYSSSVKGRFTISRDNAKNSLYLQMNSLRAEDTAVYYCARHSNVNYYAMDYWGQGTLVTVSS
PD1-4  YISGGGGDTYYSSSVKGRFTISRDNAKNSLYLQMNSLRAEDTAVYYCARHSNVNYYAMDYWGQGTLVTVSS
PD1-5  YISGGGGDTYYSSSVKGRFTISRDNAKNSLYLQMNSLRAEDTAVYYCARHSNVNYYAMDYWGQGTLVTVSS
```

FIGURE 5a
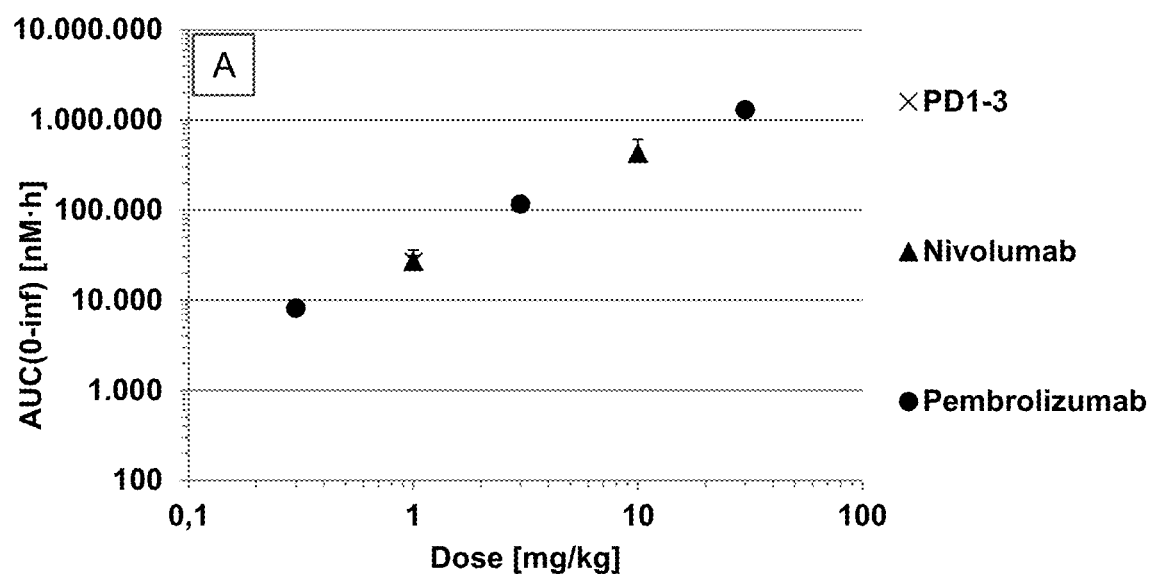
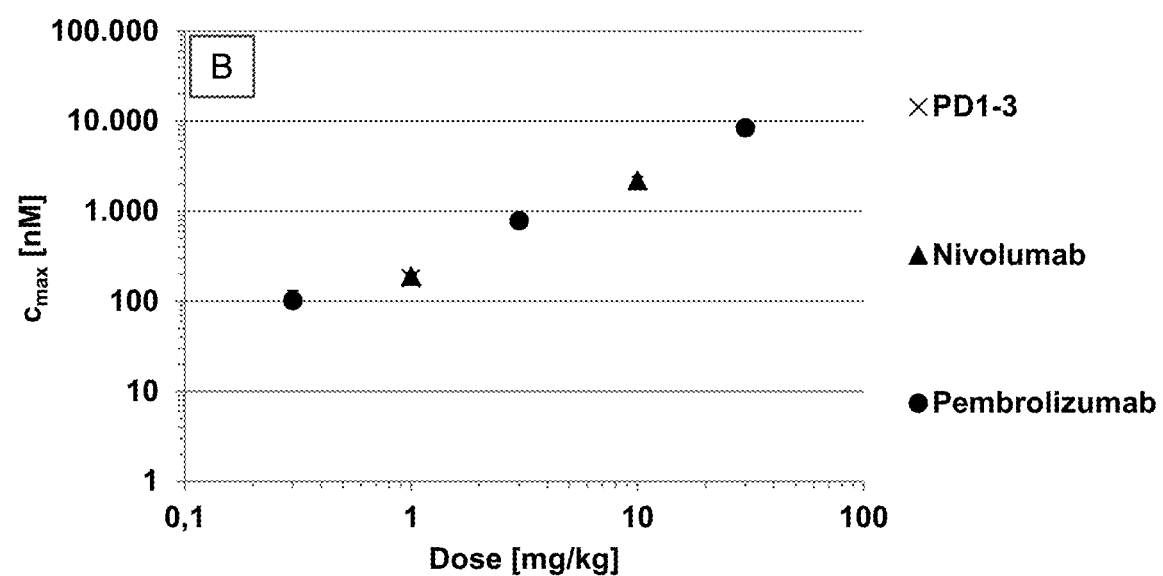

FIGURE 5b
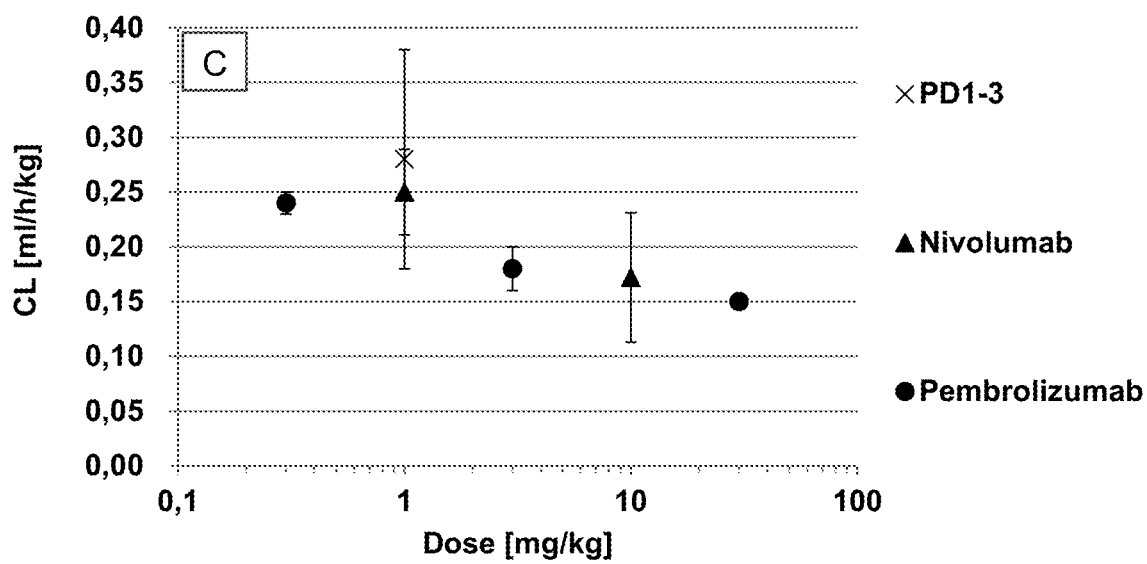
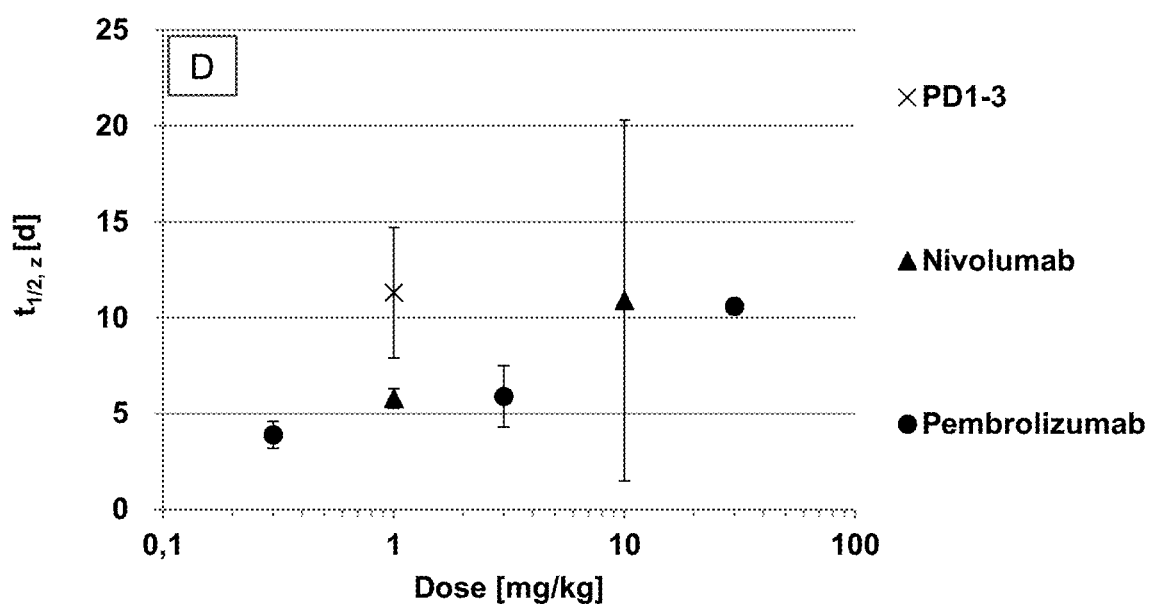

A – VK SEQUENCES

```
496G6    DIVMTQSHKFMSTSVGDRVSFTCKASQDVNTAVAWYQQKPGQSPKLLIY
LAG3-1   DIQMTQSPSFLSASVGDRVSITCKASQDVSTAVAWYQQKPGKAPKLLIY
LAG3-2   DIQMTQSPSFLSASVGDRVTFTCKASQDVSTAVAWYQQKPGKAPKLLIY
LAG3-3   DIQMTQSPSFLSASVGDRVTITCKASQDVSTAVAWYQQKPGKAPKLLIY
LAG3-4   DIVMTQSPSFLSASVGDRVTITCKASQDVSTAVAWYQQKPGKAPKLLIY
LAG3-5   DIQMTQSPSFLSASVGDRVSITCKASQDVSTAVAWYQQKPGKAPKLLIY
```

(B)

A – VK SEQUENCES

```
496G6    SASYRYTGVPDRFTGSGSGTDFTFTISSVQAEDLALYYCQQHYSIPLTFGAGTKLELK
LAG3-1   SASYRYTGVPDRFSGSGSGTDFTLTISSLQPEDFATYYCQQHYSIPLTFGQGTKLEIK
LAG3-2   SASYRYTGVPDRFSGSGSGTDFTLTISSLQPEDFATYYCQQHYSIPLTFGQGTKLEIK
LAG3-3   SASYRYTGVPDRFSGSGSGTDFTLTISSLQPEDFATYYCQQHYSIPLTFGAGTKLEIK
LAG3-4   SASYRYTGVPDRFSGSGSGTDFTLTISSLQPEDFATYYCQQHYSIPLTFGQGTKLEIK
LAG3-5   SASYRYTGVPDRFSGSGSGTDFTLTISSLQPEDFAVYYCQQHYSIPLTFGQGTKLEIK
```

B – VH SEQUENCES

```
496G6    QVTLKESGPGILQPSQTLSLTCSFSGFSLSTSDMGVGWIRQPSGKGLEWLA
LAG3-1   QVTLVESGGGVVQPGRSLRLSCAFSGFSLSTSDMGVGWIRQAPGKGLEWVA
LAG3-2   QVTLKESGPTLVKPTQTLTLTCSFSGFSLSTSDMGVGWIRQPPGKALEWLA
LAG3-3   QVTLVESGGGVVQPGRSLSLSCAFSGFSLSTSDMGVGWVRQPPGKGLEWVA
LAG3-4   QVTLVESGGGVVQPGRSLRLSCAFSGFSLSTSDMGVGWIRQAPGKGLEWVA
LAG3-5   QVTLKESGPTLVKPTQTLTLTCSFSGFSLSTSDMGVGWIRQPPGKALEWLA
```

(D)

B – VH SEQUENCES

```
496G6    HIWWDDVKRYNPALKSRLTISKDTSSSQVFLMIASVDTADTATYFCARIEDYGVSYYFDYWGQGTTLTVSS
LAG3-1   HIWWDDVKRYNPALKSRFTISRDNSKNTLYLQMNSLRAEDTAVYFCARIEDYGVSYYFDYWGQGTTVTVSS
LAG3-2   HIWWDDVKRYNPALKSRLTITKDTSKNQVVLTMTNMDPVDTATYFCARIEDYGVSYYFDYWGQGTTVTVSS
LAG3-3   HIWWDDVKRYNPALKSRFTISRDNSKNTLYLQMNSLRAEDTATYYCARIEDYGVSYYFDYWGQGTTVTVSS
LAG3-4   HIWWDDVKRYNPALKSRFTISRDNSKNTLYLQMNSLRAEDTATYFCARIEDYGVSYYFDYWGQGTTVTVSS
LAG3-5   HIWWDDVKRYNPALKSRLTITKDTSKNQVVLTMTNMDPVDTATYFCARIVDYGVSYYFDYWGQGTTVTVSS
```

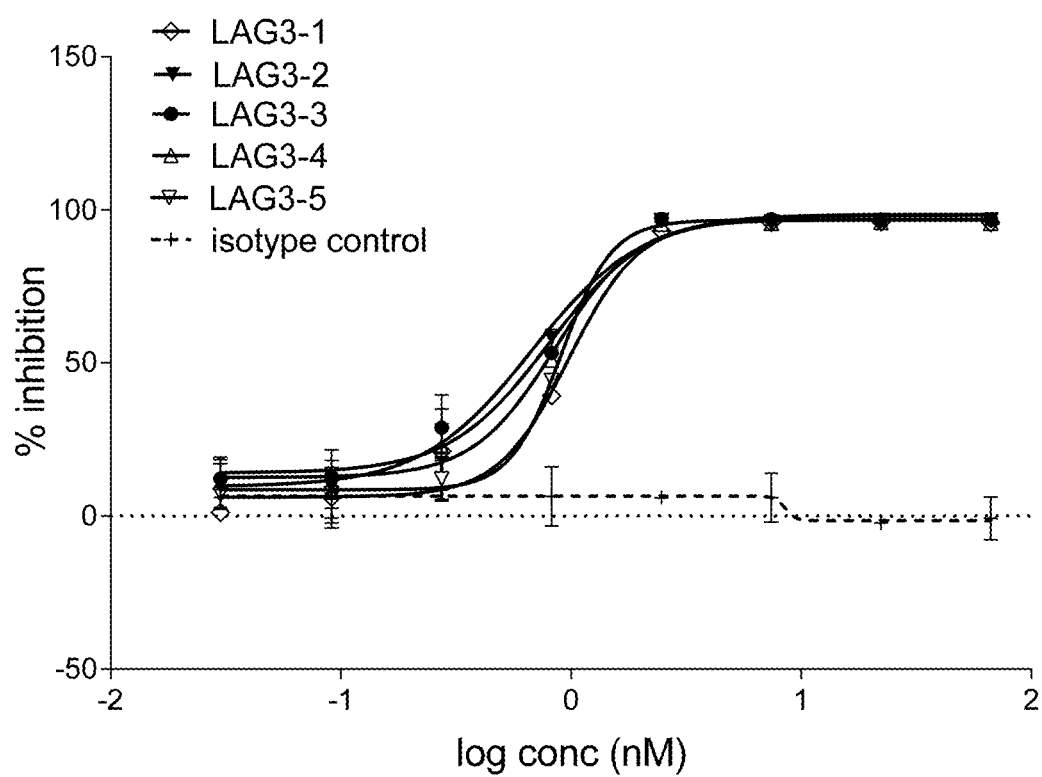

FIGURE 8
A)
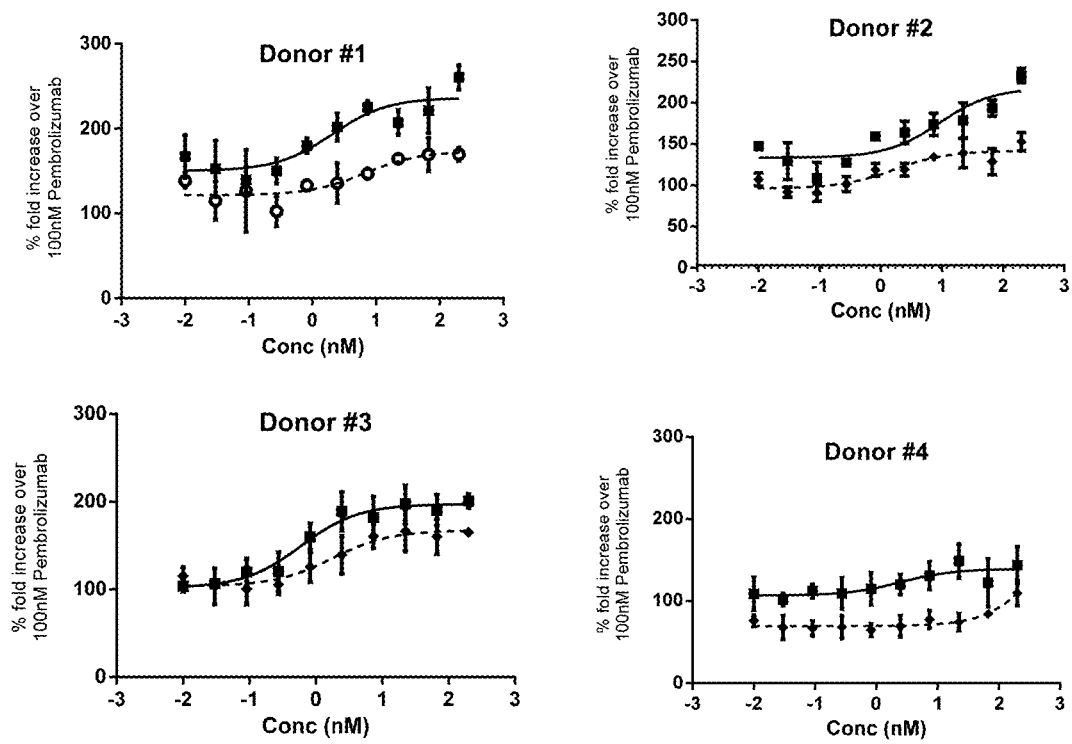
B)
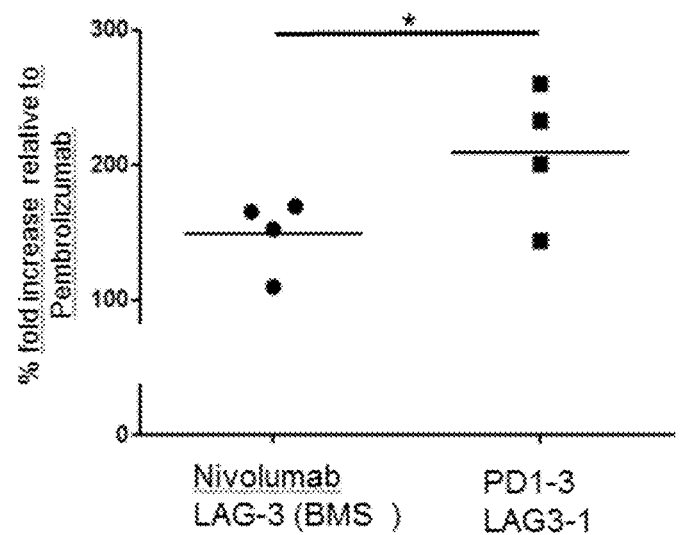

SEQUENCE LISTING

```
<160> NUMBER OF SEQ ID NOS: 118

<210> SEQ ID NO 1
<211> LENGTH: 10
<212> TYPE: PRT
<213> ORGANISM: Artificial Sequence
<220> FEATURE:
<223> OTHER INFORMATION: CDR sequence

<400> SEQUENCE: 1

Gly Phe Thr Phe Ser Ala Ser Ala Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR sequence

<400> SEQUENCE: 2

Tyr Ile Ser Gly Gly Gly Gly Asp Thr Tyr Tyr Ser Ser Ser Val Lys
1               5                   10                  15
```

Gly

<210> SEQ ID NO 3
<211> LENGTH: 11
<212> TYPE: PRT
<213> ORGANISM: Artificial Sequence
<220> FEATURE:
<223> OTHER INFORMATION: CDR sequence

<400> SEQUENCE: 3

His Ser Asn Val Asn Tyr Tyr Ala Met Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDR sequence

<400> SEQUENCE: 4

Arg Ala Ser Glu Asn Ile Asp Thr Ser Gly Ile Ser Phe Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR sequence

<400> SEQUENCE: 5

Val Ala Ser Asn Gln Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR sequence

<400> SEQUENCE: 6

Gln Gln Ser Lys Glu Val Pro Trp Thr
1               5

<210> SEQ ID NO 7
<211> LENGTH: 10
<212> TYPE: PRT
<213> ORGANISM: Artificial Sequence
<220> FEATURE:
<223> OTHER INFORMATION: CDR sequence

<400> SEQUENCE: 7

Gly Phe Thr Phe Ser Ala Ser Ala Met Ser
1               5                   10

<210> SEQ ID NO 8
<211> LENGTH: 17
<212> TYPE: PRT
<213> ORGANISM: Artificial Sequence
<220> FEATURE:
<223> OTHER INFORMATION: CDR sequence

<400> SEQUENCE: 8

Tyr Ile Ser Gly Gly Gly Gly Asp Thr Tyr Tyr Ser Ser Ser Val Lys

Gly

<210> SEQ ID NO 9
<211> LENGTH: 11
<212> TYPE: PRT
<213> ORGANISM: Artificial Sequence
<220> FEATURE:
<223> OTHER INFORMATION: CDR sequence

<400> SEQUENCE: 9

His Ser Asn Pro Asn Tyr Tyr Ala Met Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: CDR sequence

<400> SEQUENCE: 10

Arg Ala Ser Glu Asn Ile Asp Thr Ser Gly Ile Ser Phe Met Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: CDR sequence

<400> SEQUENCE: 11

Val Ala Ser Asn Gln Gly Ser
1               5

<210> SEQ ID NO 12
<211> LENGTH: 9
<212> TYPE: PRT
<213> ORGANISM: Artificial Sequence
<220> FEATURE:
<223> OTHER INFORMATION: CDR sequence

<400> SEQUENCE: 12

Gln Gln Ser Lys Glu Val Pro Trp Thr
1               5

<210> SEQ ID NO 13
<211> LENGTH: 10
<212> TYPE: PRT
<213> ORGANISM: Artificial Sequence
<220> FEATURE:
<223> OTHER INFORMATION: CDR sequence

<400> SEQUENCE: 13

Gly Phe Thr Phe Ser Lys Ser Ala Met Ser
1               5                   10

<210> SEQ ID NO 14
<211> LENGTH: 17
<212> TYPE: PRT
<213> ORGANISM: Artificial Sequence
<220> FEATURE:
<223> OTHER INFORMATION: CDR sequence

<400> SEQUENCE: 14

Tyr Ile Ser Gly Gly Gly Asp Thr Tyr Tyr Ser Ser Ser Val Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: CDR sequence

<400> SEQUENCE: 15

His Ser Asn Val Asn Tyr Tyr Ala Met Asp Tyr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: CDR sequence

<400> SEQUENCE: 16

Arg Ala Ser Glu Asn Ile Asp Val Ser Gly Ile Ser Phe Met Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDR sequence

<400> SEQUENCE: 17

Val Ala Ser Asn Gln Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR sequence

<400> SEQUENCE: 18

Gln Gln Ser Lys Glu Val Pro Trp Thr
1               5

<210> SEQ ID NO 19
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 19

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg His Ser Asn Val Asn Tyr Tyr Ala Met Asp Tyr Trp Gly Gln
        100                 105                 110

Gly Thr Leu Val Thr Val Ser Ser
        115                 120

<210> SEQ ID NO 20
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 20

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
            85                  90                  95

Glu Val Pro Trp Thr Phe Gly Gln Gly Thr Lys Leu Glu Ile Lys
        100                 105                 110

<210> SEQ ID NO 21
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 21

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg His Ser Asn Pro Asn Tyr Tyr Ala Met Asp Tyr Trp Gly Gln
        100                 105                 110

Gly Thr Leu Val Thr Val Ser Ser
        115                 120

<210> SEQ ID NO 22

```
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 22

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 23

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Ala Met Asp Tyr Trp Gly Gln
            100                 105                 110

Gly Thr Leu Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 24

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30
```

```
Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys
             100                 105                 110

<210> SEQ ID NO 25
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 25

Glu Val Met Leu Val Glu Ser Gly Gly Gly Leu Val Gln Pro Gly Gly
 1               5                  10                  15

Ser Leu Arg Leu Ser Cys Thr Ala Ser Gly Phe Thr Phe Ser Lys Ser
             20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Val Asn Tyr Tyr Ala Met Asp Tyr Trp Gly Gln
             100                 105                 110

Gly Thr Leu Val Thr Val Ser Ser
        115                 120

<210> SEQ ID NO 26
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 26

Glu Ile Val Leu Thr Gln Ser Pro Ala Thr Leu Ser Leu Ser Pro Gly
 1               5                  10                  15

Glu Arg Ala Thr Met Ser Cys Arg Ala Ser Glu Asn Ile Asp Val Ser
             20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys
             100                 105                 110
```

<210> SEQ ID NO 27
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 27

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser
        115                 120
```

<210> SEQ ID NO 28
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 28

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110
```

<210> SEQ ID NO 29
<211> LENGTH: 446
<212> TYPE: PRT
<213> ORGANISM: Artificial Sequence
<220> FEATURE:
<223> OTHER INFORMATION: Antibody chain

<400> SEQUENCE: 29

```
Glu Val Met Leu Val Glu Ser Gly Gly Gly Leu Val Gln Pro Gly Gly
1               5                   10                  15
```

```
Ser Leu Arg Leu Ser Cys Thr Ala Ser Gly Phe Thr Phe Ser Ala Ser
         20                  25                  30

Ala Met Ser Trp Val Arg Gln Ala Pro Gly Lys Gly Leu Glu Trp Val
     35                  40                  45

Ala Tyr Ile Ser Gly Gly Gly Asp Thr Tyr Tyr Ser Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
```

435                 440                 445

<210> SEQ ID NO 30
<211> LENGTH: 218
<212> TYPE: PRT
<213> ORGANISM: Artificial Sequence
<220> FEATURE:
<223> OTHER INFORMATION: Antibody chain

<400> SEQUENCE: 30

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 31
<211> LENGTH: 446
<212> TYPE: PRT
<213> ORGANISM: Artificial Sequence
<220> FEATURE:
<223> OTHER INFORMATION: Antibody chain

<400> SEQUENCE: 31

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

-continued

```
Leu Gln Met Asn Ser Leu Arg Ala Glu Asp Thr Ala Val Tyr Tyr Cys
             85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 32
<211> LENGTH: 218
<212> TYPE: PRT
<213> ORGANISM: Artificial Sequence
<220> FEATURE:
<223> OTHER INFORMATION: Antibody chain

<400> SEQUENCE: 32
```

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 33
<211> LENGTH: 446
<212> TYPE: PRT
<213> ORGANISM: Artificial Sequence
<220> FEATURE:
<223> OTHER INFORMATION: Antibody chain

<400> SEQUENCE: 33

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

-continued

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 34
<211> LENGTH: 218
<212> TYPE: PRT
<213> ORGANISM: Artificial Sequence
<220> FEATURE:
<223> OTHER INFORMATION: Antibody chain

<400> SEQUENCE: 34

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

```
Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 35
<211> LENGTH: 446
<212> TYPE: PRT
<213> ORGANISM: Artificial Sequence
<220> FEATURE:
<223> OTHER INFORMATION: Antibody chain

<400> SEQUENCE: 35

```
Glu Val Met Leu Val Glu Ser Gly Gly Gly Leu Val Gln Pro Gly Gly
  1               5                  10                  15

Ser Leu Arg Leu Ser Cys Thr Ala Ser Gly Phe Thr Phe Ser Lys Ser
             20                  25                  30

Ala Met Ser Trp Val Arg Gln Ala Pro Gly Lys Gly Leu Glu Trp Val
         35                  40                  45

Ala Tyr Ile Ser Gly Gly Gly Gly Asp Thr Tyr Tyr Ser Ser Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 36
<211> LENGTH: 218
<212> TYPE: PRT
<213> ORGANISM: Artificial Sequence
<220> FEATURE:
<223> OTHER INFORMATION: Antibody chain

<400> SEQUENCE: 36

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 37
<211> LENGTH: 446
<212> TYPE: PRT
<213> ORGANISM: Artificial Sequence
<220> FEATURE:
<223> OTHER INFORMATION: Antibody chain

<400> SEQUENCE: 37

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 38
<211> LENGTH: 218
<212> TYPE: PRT
<213> ORGANISM: Artificial Sequence
<220> FEATURE:
<223> OTHER INFORMATION: Antibody chain

<400> SEQUENCE: 38

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 39
<211> LENGTH: 12
<212> TYPE: PRT
<213> ORGANISM: Artificial Sequence
<220> FEATURE:
<223> OTHER INFORMATION: CDR sequence

<400> SEQUENCE: 39

Gly Phe Ser Leu Ser Thr Ser Asp Met Gly Val Gly
1               5                   10

<210> SEQ ID NO 40
<211> LENGTH: 16
<212> TYPE: PRT
<213> ORGANISM: Artificial Sequence
<220> FEATURE:
<223> OTHER INFORMATION: CDR sequence

<400> SEQUENCE: 40

His Ile Trp Trp Asp Asp Val Lys Arg Tyr Asn Pro Ala Leu Lys Ser
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: CDR sequence

<400> SEQUENCE: 41

Ile Glu Asp Tyr Gly Val Ser Tyr Tyr Phe Asp Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: CDR sequence

<400> SEQUENCE: 42

Lys Ala Ser Gln Asp Val Ser Thr Ala Val Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: CDR sequence

<400> SEQUENCE: 43

Ser Ala Ser Tyr Arg Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: CDR sequence

```
<400> SEQUENCE: 44

Gln Gln His Tyr Ser Ile Pro Leu Thr
1               5

<210> SEQ ID NO 45
<211> LENGTH: 12
<212> TYPE: PRT
<213> ORGANISM: Artificial Sequence
<220> FEATURE:
<223> OTHER INFORMATION: CDR sequence

<400> SEQUENCE: 45

Gly Phe Ser Leu Ser Thr Ser Asp Met Gly Val Gly
1               5                   10

<210> SEQ ID NO 46
<211> LENGTH: 16
<212> TYPE: PRT
<213> ORGANISM: Artificial Sequence
<220> FEATURE:
<223> OTHER INFORMATION: CDR sequence

<400> SEQUENCE: 46

His Ile Trp Trp Asp Asp Val Lys Arg Tyr Asn Pro Ala Leu Lys Ser
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: CDR sequence

<400> SEQUENCE: 47

Ile Val Asp Tyr Gly Val Ser Tyr Tyr Phe Asp Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: CDR sequence

<400> SEQUENCE: 48

Lys Ala Ser Gln Asp Val Ser Thr Ala Val Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: CDR sequence

<400> SEQUENCE: 49

Ser Ala Ser Tyr Arg Tyr Thr
1               5

<210> SEQ ID NO 50
<211> LENGTH: 9
<212> TYPE: PRT
<213> ORGANISM: Artificial Sequence
<220> FEATURE:
<223> OTHER INFORMATION: CDR sequence

<400> SEQUENCE: 50
```

Gln Gln His Tyr Ser Ile Pro Leu Thr
1               5

<210> SEQ ID NO 51
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 51

Gln Val Thr Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Asp Met Gly Val Gly Trp Ile Arg Gln Ala Pro Gly Lys Gly Leu Glu
            35                  40                  45

Trp Val Ala His Ile Trp Trp Asp Asp Val Lys Arg Tyr Asn Pro Ala
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Ile Glu Asp Tyr Gly Val Ser Tyr Tyr Phe Asp Tyr Trp
            100                 105                 110

Gly Gln Gly Thr Thr Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: Immunoglobulin domain

<400> SEQUENCE: 52

Asp Ile Gln Met Thr Gln Ser Pro Ser Phe Leu Ser Ala Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Gln Gly Thr Lys Leu Glu Ile Lys
            100                 105

<210> SEQ ID NO 53
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 53

-continued

```
Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
            85                  90                  95

Cys Ala Arg Ile Glu Asp Tyr Gly Val Ser Tyr Tyr Phe Asp Tyr Trp
        100                 105                 110

Gly Gln Gly Thr Thr Val Thr Val Ser Ser
            115                 120
```

<210> SEQ ID NO 54
<211> LENGTH: 107
<212> TYPE: PRT
<213> ORGANISM: Artificial Sequence
<220> FEATURE:
<223> OTHER INFORMATION: Immunoglobulin domain

<400> SEQUENCE: 54

```
Asp Ile Gln Met Thr Gln Ser Pro Ser Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
            85                  90                  95

Thr Phe Gly Gln Gly Thr Lys Leu Glu Ile Lys
        100                 105
```

<210> SEQ ID NO 55
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 55

```
Gln Val Thr Leu Val Glu Ser Gly Gly Val Val Gln Pro Gly Arg
1               5                   10                  15

Ser Leu Ser Leu Ser Cys Ala Phe Ser Gly Phe Ser Leu Ser Thr Ser
            20                  25                  30

Asp Met Gly Val Gly Trp Val Arg Gln Pro Pro Gly Lys Gly Leu Glu
        35                  40                  45

Trp Val Ala His Ile Trp Trp Asp Asp Val Lys Arg Tyr Asn Pro Ala
    50                  55                  60

Leu Lys Ser Arg Phe Thr Ile Ser Arg Asp Asn Ser Lys Asn Thr Leu
65                  70                  75                  80
```

Tyr Leu Gln Met Asn Ser Leu Arg Ala Glu Asp Thr Ala Thr Tyr Tyr
                85                  90                  95

Cys Ala Arg Ile Glu Asp Tyr Gly Val Ser Tyr Tyr Phe Asp Tyr Trp
            100                 105                 110

Gly Gln Gly Thr Thr Val Thr Val Ser Ser
            115                 120

<210> SEQ ID NO 56
<211> LENGTH: 107
<212> TYPE: PRT
<213> ORGANISM: Artificial Sequence
<220> FEATURE:
<223> OTHER INFORMATION: Immunoglobulin domain

<400> SEQUENCE: 56

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Ala Gly Thr Lys Leu Glu Ile Lys
            100                 105

<210> SEQ ID NO 57
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 57

Gln Val Thr Leu Val Glu Ser Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Asp Met Gly Val Gly Trp Ile Arg Gln Ala Pro Gly Lys Gly Leu Glu
        35                  40                  45

Trp Val Ala His Ile Trp Trp Asp Asp Val Lys Arg Tyr Asn Pro Ala
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Thr Tyr Phe
                85                  90                  95

Cys Ala Arg Ile Glu Asp Tyr Gly Val Ser Tyr Tyr Phe Asp Tyr Trp
            100                 105                 110

Gly Gln Gly Thr Thr Val Thr Val Ser Ser
            115                 120

<210> SEQ ID NO 58
<211> LENGTH: 107
<212> TYPE: PRT

```
<213> ORGANISM: Artificial Sequence
<220> FEATURE:
<223> OTHER INFORMATION: Immunoglobulin domain

<400> SEQUENCE: 58

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Gln Gly Thr Lys Leu Glu Ile Lys
            100                 105

<210> SEQ ID NO 59
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 59

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Ala Arg Ile Val Asp Tyr Gly Val Ser Tyr Tyr Phe Asp Tyr Trp
            100                 105                 110

Gly Gln Gly Thr Thr Val Thr Val Ser Ser
        115                 120

<210> SEQ ID NO 60
<211> LENGTH: 107
<212> TYPE: PRT
<213> ORGANISM: Artificial Sequence
<220> FEATURE:
<223> OTHER INFORMATION: Immunoglobulin domain

<400> SEQUENCE: 60

Asp Ile Gln Met Thr Gln Ser Pro Ser Phe Leu Ser Ala Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

Tyr Ser Ala Ser Tyr Arg Tyr Thr Gly Val Pro Asp Arg Phe Ser Gly
                50                  55                  60

Ser Gly Ser Gly Thr Asp Phe Thr Leu Thr Ile Ser Ser Leu Gln Pro
 65              70                  75                      80

Glu Asp Phe Ala Val Tyr Tyr Cys Gln Gln His Tyr Ser Ile Pro Leu
                85                  90                  95

Thr Phe Gly Gln Gly Thr Lys Leu Glu Ile Lys
               100                 105

<210> SEQ ID NO 61
<211> LENGTH: 448
<212> TYPE: PRT
<213> ORGANISM: Artificial Sequence
<220> FEATURE:
<223> OTHER INFORMATION: Antibody chain

<400> SEQUENCE: 61

Gln Val Thr Leu Val Glu Ser Gly Gly Val Val Gln Pro Gly Arg
 1               5                  10                  15

Ser Leu Arg Leu Ser Cys Ala Phe Ser Gly Phe Ser Leu Ser Thr Ser
                20                  25                  30

Asp Met Gly Val Gly Trp Ile Arg Gln Ala Pro Gly Lys Gly Leu Glu
                35                  40                  45

Trp Val Ala His Ile Trp Trp Asp Asp Val Lys Arg Tyr Asn Pro Ala
 50                  55                  60

Leu Lys Ser Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Phe
                85                  90                  95

Cys Ala Arg Ile Glu Asp Tyr Gly Val Ser Tyr Tyr Phe Asp Tyr Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Cys Ser Arg Ser Thr Ser Glu Ser Thr
 130                 135                 140

Ala Ala Leu Gly Cys Leu Val Lys Asp Tyr Phe Pro Glu Pro Val Thr
145                  150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
 210                 215                 220

Gly Pro Pro Cys Pro Pro Cys Pro Ala Pro Glu Phe Leu Gly Gly Pro
225                  230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
 290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 62
<211> LENGTH: 214
<212> TYPE: PRT
<213> ORGANISM: Artificial Sequence
<220> FEATURE:
<223> OTHER INFORMATION: Antibody chain

<400> SEQUENCE: 62

Asp Ile Gln Met Thr Gln Ser Pro Ser Phe Leu Ser Ala Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 448
<212> TYPE: PRT
<213> ORGANISM: Artificial Sequence
<220> FEATURE:
<223> OTHER INFORMATION: Antibody chain

<400> SEQUENCE: 63

```
Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Ala Arg Ile Glu Asp Tyr Gly Val Ser Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365
```

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 64
<211> LENGTH: 214
<212> TYPE: PRT
<213> ORGANISM: Artificial Sequence
<220> FEATURE:
<223> OTHER INFORMATION: Antibody chain

<400> SEQUENCE: 64

Asp Ile Gln Met Thr Gln Ser Pro Ser Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 448
<212> TYPE: PRT
<213> ORGANISM: Artificial Sequence
<220> FEATURE:
<223> OTHER INFORMATION: Antibody chain

<400> SEQUENCE: 65

Gln Val Thr Leu Val Glu Ser Gly Gly Gly Val Val Gln Pro Gly Arg

-continued

```
1               5                   10                  15
Ser Leu Ser Leu Ser Cys Ala Phe Gly Phe Ser Leu Ser Thr Ser
                20                  25                  30
Asp Met Gly Val Gly Trp Val Arg Gln Pro Gly Lys Gly Leu Glu
                35                  40                  45
Trp Val Ala His Ile Trp Trp Asp Asp Val Lys Arg Tyr Asn Pro Ala
    50                  55                  60
Leu Lys Ser Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Thr Tyr Tyr
                85                  90                  95
Cys Ala Arg Ile Glu Asp Tyr Gly Val Ser Tyr Tyr Phe Asp Tyr Trp
                100                 105                 110
Gly Gln Gly Thr Thr Val Thr Val Ser Ser Ala Ser Thr Lys Gly Pro
                115                 120                 125
Ser Val Phe Pro Leu Ala Pro Cys Ser Arg Ser Thr Ser Glu Ser Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
                195                 200                 205
His Lys Pro Ser Asn Thr Lys Val Asp Lys Arg Val Glu Ser Lys Tyr
            210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
```

```
Ala Leu His Asn His Tyr Thr Gln Lys Ser Leu Ser Leu Ser Leu Gly
        435                 440                 445

<210> SEQ ID NO 66
<211> LENGTH: 214
<212> TYPE: PRT
<213> ORGANISM: Artificial Sequence
<220> FEATURE:
<223> OTHER INFORMATION: Antibody chain

<400> SEQUENCE: 66

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 67
<211> LENGTH: 448
<212> TYPE: PRT
<213> ORGANISM: Artificial Sequence
<220> FEATURE:
<223> OTHER INFORMATION: Antibody chain

<400> SEQUENCE: 67

Gln Val Thr Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Asp Met Gly Val Gly Trp Ile Arg Gln Ala Pro Gly Lys Gly Leu Glu
        35                  40                  45

Trp Val Ala His Ile Trp Trp Asp Asp Val Lys Arg Tyr Asn Pro Ala
50                  55                  60

Leu Lys Ser Arg Phe Thr Ile Ser Arg Asp Asn Ser Lys Asn Thr Leu
```

```
            65                  70                  75                  80
        Tyr Leu Gln Met Asn Ser Leu Arg Ala Glu Asp Thr Ala Thr Tyr Phe
                        85                  90                  95

Cys Ala Arg Ile Glu Asp Tyr Gly Val Ser Tyr Tyr Phe Asp Tyr Trp
                       100                 105                 110

Gly Gln Gly Thr Thr Val Thr Val Ser Ser Ala Ser Thr Lys Gly Pro
                       115                 120                 125

Ser Val Phe Pro Leu Ala Pro Cys Ser Arg Ser Thr Ser Glu Ser Thr
               130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                       165                 170                 175

Ala Val Leu Gln Ser Ser Gly Leu Tyr Ser Leu Ser Ser Val Val Thr
                       180                 185                 190

Val Pro Ser Ser Ser Leu Gly Thr Lys Thr Tyr Thr Cys Asn Val Asp
                       195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Leu Gly Gly Pro
        225                 230                 235                 240

Ser Val Phe Leu Phe Pro Pro Lys Pro Lys Asp Thr Leu Met Ile Ser
                       245                 250                 255

Arg Thr Pro Glu Val Thr Cys Val Val Val Asp Val Ser Gln Glu Asp
                       260                 265                 270

Pro Glu Val Gln Phe Asn Trp Tyr Val Asp Gly Val Glu Val His Asn
                       275                 280                 285

Ala Lys Thr Lys Pro Arg Glu Glu Gln Phe Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Gly Leu Pro Ser Ser Ile Glu Lys
                       325                 330                 335

Thr Ile Ser Lys Ala Lys Gly Gln Pro Arg Glu Pro Gln Val Tyr Thr
                       340                 345                 350

Leu Pro Pro Ser Gln Glu Glu Met Thr Lys Asn Gln Val Ser Leu Thr
                       355                 360                 365

Cys Leu Val Lys Gly Phe Tyr Pro Ser Asp Ile Ala Val Glu Trp Glu
               370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Arg Leu Thr Val Asp Lys
                       405                 410                 415

Ser Arg Trp Gln Glu Gly Asn Val Phe Ser Cys Ser Val Met His Glu
                       420                 425                 430

Ala Leu His Asn His Tyr Thr Gln Lys Ser Leu Ser Leu Ser Leu Gly
                       435                 440                 445

<210> SEQ ID NO 68
<211> LENGTH: 214
<212> TYPE: PRT
<213> ORGANISM: Artificial Sequence
<220> FEATURE:
<223> OTHER INFORMATION: Antibody chain
```

<400> SEQUENCE: 68

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 69
<211> LENGTH: 448
<212> TYPE: PRT
<213> ORGANISM: Artificial Sequence
<220> FEATURE:
<223> OTHER INFORMATION: Antibody chain

<400> SEQUENCE: 69

```
Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Ala Arg Ile Val Asp Tyr Gly Val Ser Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
```

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 70
<211> LENGTH: 214
<212> TYPE: PRT
<213> ORGANISM: Artificial Sequence
<220> FEATURE:
<223> OTHER INFORMATION: Antibody chain

<400> SEQUENCE: 70

Asp Ile Gln Met Thr Gln Ser Pro Ser Phe Leu Ser Ala Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Asp Arg Phe Ser Gly
```

```
                50             55              60
Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln His Tyr Ser Ile Pro Leu
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 360
<212> TYPE: DNA
<213> ORGANISM: Artificial Sequence
<220> FEATURE:
<223> OTHER INFORMATION: Immunoglobulin domain

<400> SEQUENCE: 71
gaggtgatgc tggtcgagag cggcggcggt ctcgtgcagc caggcggtag cctgcgcctc     60
agctgcaccg ccagcggctt cacctttcagc gctagcgcca tgagctgggt gcgccaagcc    120
ccaggcaagg gcctggagtg ggtggcctac atcagcggcg gcggcggcga cacctactac    180
agctccagcg tgaagggccg cttcaccatc agccgcgaca cgccaaaaa cagcctgtac    240 ctgcaaatga acagcctgcg cgccgaggac accgccgtgt actactgcgc ccgccacagc    300
aacgtcaact actacgccat ggactactgg ggccagggca ccctggtgac cgtgagcagc    360

<210> SEQ ID NO 72
<211> LENGTH: 333
<212> TYPE: DNA
<213> ORGANISM: Artificial Sequence
<220> FEATURE:
<223> OTHER INFORMATION: Immunoglobulin domain

<400> SEQUENCE: 72
gagatcgtgc tgacccagag cccagccacc ctgagcctga gcccaggcga gcgcgccacc     60
atgagctgcc gcgccagcga gaacatcgac accagcggca tcagcttcat gaactggtac    120
cagcagaagc caggccaggc cccaaagctg ctgatctacg tggccagcaa ccagggcagc    180
ggcatcccag cccgcttcag cggcagcggc agcggcaccg acttcaccct gaccatcagc    240
cgcctggagc cagaggactt cgccgtgtac tactgccagc agagcaagga agtcccatgg    300
accttcggcc aaggtactaa gctggagatc aag                                 333

<210> SEQ ID NO 73
<211> LENGTH: 360
```

```
<212> TYPE: DNA
<213> ORGANISM: Artificial Sequence
<220> FEATURE:
<223> OTHER INFORMATION: Immunoglobulin domain

<400> SEQUENCE: 73
gaggtgatgc tggtcgagag cggcggcggt ctcgtgcagc caggcggtag cctgcgcctc    60
agctgcaccg ccagcggctt caccttcagc gctagcgcca tgagctgggt gcgccaagcc   120
ccaggcaagg gcctggagtg ggtggcctac atcagcggcg gcggcggcga cacctactac   180
agctccagcg tgaagggccg cttcaccatc agccgcgaca acgccaaaaa cagcctgtac   240
ctgcaaatga acagcctgcg cgccgaggac accgccgtgt actactgcgc cgccacagc   300 aacccaaact actacgccat ggactactgg ggccagggca cctggtgac cgtgagcagc   360

<210> SEQ ID NO 74
<211> LENGTH: 333
<212> TYPE: DNA
<213> ORGANISM: Artificial Sequence
<220> FEATURE:
<223> OTHER INFORMATION: Immunoglobulin domain

<400> SEQUENCE: 74
gagatcgtgc tgacccagag cccagccacc ctgagcctga gcccaggcga gcgcgccacc    60
atgagctgcc gcgccagcga gaacatcgac accagcggca tcagcttcat gaactggtac   120
cagcagaagc caggccaggc cccaaagctg ctgatctacg tggccagcaa ccagggcagc   180
ggcatcccag cccgcttcag cggcagcggc agcggcaccg acttcaccct gaccatcagc   240
cgcctggagc cagaggactt cgccgtgtac tactgccagc agagcaagga agtcccatgg   300
accttcggcc aaggtactaa gctggagatc aag                                 333

<210> SEQ ID NO 75
<211> LENGTH: 360
<212> TYPE: DNA
<213> ORGANISM: Artificial Sequence
<220> FEATURE:
<223> OTHER INFORMATION: Immunoglobulin domain

<400> SEQUENCE: 75
gaggtgatgc tggtcgagag cggcggcggt ctcgtgcagc caggcggtag cctgcgcctc    60
agctgcaccg ccagcggctt caccttcagc aagagcgcca tgagctgggt gcgccaagcc   120
ccaggcaagg gcctggagtg ggtggcctac atcagcggcg gcggcggcga cacctactac   180
agctccagcg tgaagggccg cttcaccatc agccgcgaca acgccaagaa cagcctgtac   240
ctgcaaatga acagcctgcg cgccgaggac accgccgtgt actactgcgc cgccacagc   300 aacgtcaact actacgccat ggactactgg ggccagggca cctggtgac cgtgagcagc   360

<210> SEQ ID NO 76
<211> LENGTH: 333
<212> TYPE: DNA
<213> ORGANISM: Artificial Sequence
<220> FEATURE:
<223> OTHER INFORMATION: Immunoglobulin domain

<400> SEQUENCE: 76
gagatcgtgc tgacccagag cccagccacc ctaagcctga gcccaggcga gcgcgccacc    60
atgagctgcc gcgccagcga gaacatcgac cacagcggca tcagcttcat gaactggtac   120
cagcagaagc caggccaggc cccaaagctg ctgatctacg tggccagcaa ccagggcagc   180
```

-continued

```
ggcatcccag cccgcttcag cggcagcggc agcggcaccg acttcaccct gaccatcagc    240
cgcctggagc cagaggactt cgccgtgtac tactgccagc agagcaagga agtcccatgg    300
accttcggcc aaggtactaa gctggagatc aag                                 333
```

<210> SEQ ID NO 77
<211> LENGTH: 360
<212> TYPE: DNA
<213> ORGANISM: Artificial Sequence
<220> FEATURE:
<223> OTHER INFORMATION: Immunoglobulin domain

<400> SEQUENCE: 77

```
gaggtgatgc tggtcgagag cggcggcggt ctcgtgcagc caggcggtag cctgcgcctc    60
agctgcaccg ccagcggctt caccttcagc aagagcgcca tgagctgggt gcgccaagcc    120
ccaggcaagg gcctggagtg ggtggcctac atcagcggcg gcggcggcga cacctactac    180
agctccagcg tgaagggccg cttcaccatc agccgcgaca cgccaagaa cagcctgtac    240 ctgcaaatga acagcctgcg cgccgaggac accgccgtgt actactgcgc cgccacagc    300 aacgtcaact actacgccat ggactactgg ggccagggca ccctggtgac cgtgagcagc    360
```

<210> SEQ ID NO 78
<211> LENGTH: 333
<212> TYPE: DNA
<213> ORGANISM: Artificial Sequence
<220> FEATURE:
<223> OTHER INFORMATION: Immunoglobulin domain

<400> SEQUENCE: 78

```
gagatcgtgc tgacccagag cccagccacc ctaagcctga gcccaggcga gcgcgccacc    60
atgagctgcc gcgccagcga gaacatcgac acacagcgga tcagcttcat gaactggtac    120
cagcagaagc caggccaggc cccaaagctg ctgatctacg tggccagcaa ccagggcagc    180
ggcatcccag cccgcttcag cggcagcggc agcggcaccg acttcaccct gaccatcagc    240
cgcctggagc cagaggactt cgccgtgtac tactgccagc agagcaagga agtcccatgg    300
accttcggcc aaggtactaa gctggagatc aag                                 333
```

<210> SEQ ID NO 79
<211> LENGTH: 360
<212> TYPE: DNA
<213> ORGANISM: Artificial Sequence
<220> FEATURE:
<223> OTHER INFORMATION: Immunoglobulin domain

<400> SEQUENCE: 79

```
gaggtgatgc tggtcgagag cggcggcggt ctcgtgcagc caggcggtag cctgcgcctc    60
agctgcaccg ccagcggctt caccttcagc aagagcgcca tgagctgggt gcgccaagcc    120
ccaggcaagg gcctggagtg ggtggcctac atcagcggcg gcggcggcga cacctactac    180
agctccagcg tgaagggccg cttcaccatc agccgcgaca cgccaagaa cagcctgtac    240 ctgcaaatga acagcctgcg cgccgaggac accgccgtgt actactgcgc cgccacagc    300 aacgtcaact actacgccat ggactactgg ggccagggca ccctggtgac cgtgagcagc    360
```

<210> SEQ ID NO 80
<211> LENGTH: 333
<212> TYPE: DNA
<213> ORGANISM: Artificial Sequence
<220> FEATURE:
<223> OTHER INFORMATION: Immunoglobulin domain

<400> SEQUENCE: 80

```
gagatcgtgc tgacccagag cccagccacc ctgagcctga gcccaggcga gcgcgccacc    60
atgagctgcc gcgccagcga gaacatcgac gtaagcggca tcagcttcat gaactggtac   120
cagcagaagc caggccaggc cccaaagctg ctgatctacg tggccagcaa ccagggcagc   180
ggcatcccag cccgcttcag cggcagcggc agcggcaccg acttcaccct gaccatcagc   240
cgcctggagc agaggacttt cgccgtgtac tactgccagc agagcaagga agtcccatgg   300
accttcggcc aaggtactaa gctggaaatc aag                                333
```

<210> SEQ ID NO 81
<211> LENGTH: 1338
<212> TYPE: DNA
<213> ORGANISM: Artificial Sequence
<220> FEATURE:
<223> OTHER INFORMATION: Antibody chain

<400> SEQUENCE: 81

```
gaggtgatgc tggtcgagag cggcggcggt ctcgtgcagc caggcggtag cctgcgcctc    60
agctgcaccg ccagcggctt caccttcagc gctagcgcca tgagctgggt cgccaagcc   120
ccaggcaagg gcctggagtg ggtggcctac atcagcggcg gcggcggcga cacctactac   180
agctccagcg tgaagggccg cttcaccatc agcgcgacaa cgccaaaaa cagcctgtac   240
ctgcaaatga acagcctgcg cgccgaggac accgccgtgt actactgcgc cgccacagc   300
aacgtcaact actacgccat ggactactgg ggccagggca ccctggtgac cgtgagcagc   360
gcctccacaa agggcccttc cgtgttcccc ctggccccttt gctccggtc cacctccgag   420
tctaccgccg ctctgggctg cctggtcaag gactacttcc ccgagcccgt gaccgtgtcc   480
tggaactctg gcgccctgac ctccggcgtg cacaccttcc ctgctgtgct gcagtcctcc   540
ggcctgtact ccctgtcctc cgtcgtgacc gtgccctcct ctagcctggg caccaagacc   600
tacacctgta acgtggacca caagccctcc aacaccaagg tggacaagcg ggtggaatct   660
aagtacggcc ctcccctgccc ccctgccct gccctgaat ttctgggcgg accctccgtg   720
ttcctgttcc cccaaagcc aaggacacc ctgatgatct cccggacccc cgaagtgacc   780
tgcgtggtgg tggacgtgtc ccaggaagat cccgaggtcc agtttaattg gtacgtggac   840
ggcgtggaag tgcacaacgc caagaccaag cccagagagg aacagttcaa ctccacctac   900
cgggtggtgt ccgtgctgac cgtgctgcac caggactggc tgaacggcaa agagtacaag   960
tgcaaggtgt ccaacaaggg cctgcccctcc agcatcgaaa agaccatctc caaggccaag  1020
ggccagcccc gcgagcccca ggtgtacacc ctgcctccaa gccaggaaga tgaccaag    1080
aaccaggtgt ccctgacctg tctggtcaag ggcttctacc cctccgatat cgccgtggaa  1140
tgggagtcca acggccagcc cgagaacaac tacaagacca ccccccctgt gctggactcc  1200
gacggctcct tcttcctgta ctctcggctg accgtggaca gtcccggtg gcaggaaggc  1260
aacgtcttct cctgctccgt gatgcacgag gccctgcaca accactacac ccagaagtcc  1320
ctgtccctga gcctgggc                                              1338
```

<210> SEQ ID NO 82
<211> LENGTH: 654
<212> TYPE: DNA
<213> ORGANISM: Artificial Sequence
<220> FEATURE:
<223> OTHER INFORMATION: Antibody chain

<400> SEQUENCE: 82

```
gagatcgtgc tgacccagag cccagccacc ctgagcctga gcccaggcga gcgcgccacc    60
atgagctgcc gcgccagcga gaacatcgac accagcggca tcagcttcat gaactggtac   120
cagcagaagc caggccaggc cccaaagctg ctgatctacg tggccagcaa ccagggcagc   180
ggcatcccag cccgcttcag cggcagcggc agcggcaccg acttcaccct gaccatcagc   240
cgcctggagc cagaggactt cgccgtgtac tactgccagc agagcaagga agtcccatgg   300
accttcggcc aaggtactaa gctggagatc aagcgtactg tggctgcacc atctgtcttc   360
atcttcccgc catctgatga gcaattgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca aagtctacgc ctgcgaagtc   600
acccatcagg gcctgagctc gcccgtcaca aagagcttca caggggaga gtgt           654
```

<210> SEQ ID NO 83
<211> LENGTH: 1338
<212> TYPE: DNA
<213> ORGANISM: Artificial Sequence
<220> FEATURE:
<223> OTHER INFORMATION: Antibody chain

<400> SEQUENCE: 83

```
gaggtgatgc tggtcgagag cggcggcggt ctcgtgcagc caggcggtag cctgcgcctc    60
agctgcaccg ccagcggctt caccttcagc gctagcgcca tgagctgggt gcgccaagcc   120
ccaggcaagg gcctggagtg ggtggcctac atcagcggcg gcggcggcga cacctactac   180
agctccagcg tgaagggccg cttcaccatc agcgcgcgaca acgccaaaaa cagcctgtac   240
ctgcaaatga acagcctgcg cgccgaggac accgccgtgt actactgcgc cgccacagc   300
aacccaaact actacgccat ggactactgg ggccagggca ccctggtgac cgtgagcagc   360
gcctccacaa agggcccttc cgtgttcccc ctggcccctt gctccggtc cacctccgag   420
tctaccgccg ctctgggctg cctggtcaag gactacttcc ccgagcccgt gaccgtgtcc   480
tggaactctg gcgccctgac ctccggcgtg cacaccttcc ctgctgtgct gcagtcctcc   540
ggcctgtact ccctgtcctc cgtcgtgacc gtgccctcct ctagcctggg caccaagacc   600
tacacctgta acgtggacca caagcccctcc aacaccaagg tggacaagcg ggtggaatct   660
aagtacggcc ctccctgccc ccctgcccct gccctgaat ttctgggcgg accctccgtg   720
ttcctgttcc cccaaagcc caaggacacc ctgatgatct cccggaccc cgaagtgacc   780
tgcgtggtgg tggacgtgtc ccaggaagat cccgaggtcc agtttaattg gtacgtggac   840
ggcgtggaag tgcacaacgc caagaccaag cccagagagg aacagttcaa ctccacctac   900
cgggtggtgt ccgtgctgac cgtgctgcac caggactggc tgaacggcaa agagtacaag   960
tgcaaggtgt ccaacaaggg cctgcctcc agcatcgaaa agaccatctc caaggccaag  1020
ggccagcccc gcgagcccca ggtgtacacc ctgcctccaa gccaggaaga gatgaccaag  1080
aaccaggtgt ccctgacctg tctggtcaag ggcttctacc cctccgatat cgccgtggaa  1140
tgggagtcca acggccagcc cgagaacaac tacaagacca ccccccctgt gctggactcc  1200
gacggctcct tcttcctgta ctctcggctg accgtggaca gtcccggtg gcaggaaggc  1260
aacgtcttct cctgctccgt gatgcacgag gccctgcaca accactacac ccagaagtcc  1320
ctgtccctga gctgggc                                                  1338
```

<210> SEQ ID NO 84
<211> LENGTH: 654
<212> TYPE: DNA
<213> ORGANISM: Artificial Sequence
<220> FEATURE:
<223> OTHER INFORMATION: Antibody chain

<400> SEQUENCE: 84

```
gagatcgtgc tgacccagag cccagccacc ctgagcctga gcccaggcga gcgcgccacc    60
atgagctgcc gcgccagcga gaacatcgac accagcggca tcagcttcat gaactggtac   120
cagcagaagc caggccaggc cccaaagctg ctgatctacg tggccagcaa ccagggcagc   180
ggcatcccag cccgcttcag cggcagcggc agcggcaccg acttcaccct gaccatcagc   240
cgcctggagc agaggacttt cgccgtgtac tactgccagc agagcaagga agtcccatgg   300
accttcggcc aaggtactaa gctggagatc aagcgtactg tggctgcacc atctgtcttc   360
atcttcccgc catctgatga gcaattgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc tgcgaagtc    600
acccatcagg gcctgagctc gcccgtcaca aagagcttca caggggaga gtgt         654
```

<210> SEQ ID NO 85
<211> LENGTH: 1338
<212> TYPE: DNA
<213> ORGANISM: Artificial Sequence
<220> FEATURE:
<223> OTHER INFORMATION: Antibody chain

<400> SEQUENCE: 85

```
gaggtgatgc tggtcgagag cggcggcggt ctcgtgcagc caggcggtag cctgcgcctc    60
agctgcaccg ccagcggctt caccttcagc aagagcgcca tgagctgggt gcgccaagcc   120
ccaggcaagg gcctggagtg ggtggcctac atcagcggcg gcggcggcga cacctactac   180
agctccagcg tgaagggccg cttcaccatc agccgcgaca cgccaagaa cagcctgtac   240
ctgcaaatga acagcctgcg cgccgaggac accgccgtgt actactgcgc ccgccacagc   300
aacgtcaact actacgccat ggactactgg ggccagggca ccctggtgac cgtgagcagc   360
gcctccacaa agggcccttc cgtgttcccc ctggcccctt gctccgggtc cacctccgag   420
tctaccgccg ctctgggctg cctggtcaag gactacttcc ccgagcccgt gaccgtgtcc   480
tggaactctg gcgccctgac ctccggcgtg cacaccttcc ctgctgtgct gcagtcctcc   540
ggcctgtact ccctgtcctc cgtcgtgacc gtgccctcct tagcctgggg caccaagacc   600
tacacctgta acgtggacca caagcccctcc aacaccaagg tggacaagcg ggtggaatct   660
aagtacggcc ctcccctgcc ccctgccct gccctgaat ttctgggcgg accctccgtg   720
ttcctgttcc ccccaaagcc caaggacacc ctgatgatct cccggaccc cgaagtgacc   780
tgcgtggtgg tggacgtgtc ccaggaagat cccgaggtcc agtttaattg gtacgtggac   840
ggcgtggaag tgcacaacgc caagaccaag cccagagagg aacagttcaa ctccacctac   900
cgggtggtgt ccgtgctgac cgtgctgcac caggactggc tgaacggcaa agagtacaag   960
tgcaaggtgt ccaacaaggg cctgcccctcc agcatcgaaa agaccatctc caaggccaag  1020
ggccagcccc gcgagcccca ggtgtacacc ctgcctccaa gccaggaaga gatgaccaag  1080
```

| | |
|---|---|
| aaccaggtgt ccctgacctg tctggtcaag ggcttctacc cctccgatat cgccgtggaa | 1140 |
| tgggagtcca acggccagcc cgagaacaac tacaagacca ccccccctgt gctggactcc | 1200 |
| gacggctcct tcttcctgta ctctcggctg accgtggaca agtcccggtg gcaggaaggc | 1260 |
| aacgtcttct cctgctccgt gatgcacgag gccctgcaca accactacac ccagaagtcc | 1320 |
| ctgtccctga gcctgggc | 1338 |

<210> SEQ ID NO 86
<211> LENGTH: 654
<212> TYPE: DNA
<213> ORGANISM: Artificial Sequence
<220> FEATURE:
<223> OTHER INFORMATION: Antibody chain

<400> SEQUENCE: 86

| | |
|---|---|
| gagatcgtgc tgacccagag cccagccacc ctgagcctga gccaggcga gcgcgccacc | 60 |
| atgagctgcc gcgccagcga gaacatcgac gtaagcggca tcagcttcat gaactggtac | 120 |
| cagcagaagc caggccaggc cccaaagctg ctgatctacg tggccagcaa ccagggcagc | 180 |
| ggcatcccag cccgcttcag cggcagcggc agcggcaccg acttcaccct gaccatcagc | 240 |
| cgcctggagc cagaggactt cgccgtgtac tactgccagc agagcaagga agtcccatgg | 300 |
| accttcggcc aaggtactaa gctggaaatc aagcgtactg tggctgcacc atctgtcttc | 360 |
| atcttcccgc catctgatga gcaattgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgt | 654 |

<210> SEQ ID NO 87
<211> LENGTH: 1347
<212> TYPE: DNA
<213> ORGANISM: Artificial Sequence
<220> FEATURE:
<223> OTHER INFORMATION: Antibody chain

<400> SEQUENCE: 87

| | |
|---|---|
| gaggtgatgc tggtcgagag cggcggcggt ctcgtgcagc caggcggtag cctgcgcctc | 60 |
| agctgcaccg ccagcggctt caccttcagc cgcagcgcca tgagctgggt cgccaagcc | 120 |
| ccaggcaagg gcctggagtg ggtggcctac atcagcggcg gcggcggcga cacctactac | 180 |
| agcgtcagcg tgaagggccg cttcaccatc agccgcgaca cgccaagaa cagcctgtac | 240 |
| ctgcaaatga acagcctgcg cgccgaggac accgccgtgt actactgcgc ccgccacagc | 300 |
| aactacaact actacgccat ggactactgg ggccagggca cctggtgac cgtgagcagc | 360 |
| gcctccacca agggcccatc ggtcttcccg ctagcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagcg cgttgagccc | 660 |
| aaatcttgtg acaaaactca cacatgccca ccgtgcccag cacctgaagc cgctggggga | 720 |
| ccgtcagtct tcctcttccc cccaaaaccc aaggacaccc tcatgatctc ccggaccct | 780 |
| gaggtcacat gcgtggtggt ggacgtgagc cacgaagacc ctgaggtcaa gttcaactgg | 840 |

```
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgcgaggag      1080
atgaccaaga accaggtaag tttgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctat agcaagctca ccgtggacaa gagcaggtgg     1260
cagcagggga acgtcttctc atgctccgtg atgcatgagg ctctgcacaa ccactacacg     1320
cagaagagcc tctccctgtc tccgggt                                          1347
```

<210> SEQ ID NO 88
<211> LENGTH: 654
<212> TYPE: DNA
<213> ORGANISM: Artificial Sequence
<220> FEATURE:
<223> OTHER INFORMATION: Antibody chain

<400> SEQUENCE: 88

```
gagatcgtgc tgacccagag cccagccacc ctaagcctga gcccaggcga gcgcgccacc       60
atgagctgcc gcgccagcga gaacatcgac cacagcggca tcagcttcat gaactggtac      120
cagcagaagc caggccaggc cccaaagctg ctgatctacg tggccagcaa ccagggcagc      180
ggcatcccag cccgcttcag cggcagcggc agcggcaccg acttcaccct gaccatcagc      240
cgcctggagc cagaggactt cgccgtgtac tactgccagc agagcaagga agtcccatgg      300
accttcggcc aaggtactaa gctggagatc aagcgtactg tggctgcacc atctgtcttc      360
atcttcccgc catctgatga gcaattgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc      600 acccatcagg gcctgagctc gcccgtcaca aagagcttca caggggaga gtgt            654
```

<210> SEQ ID NO 89
<211> LENGTH: 1338
<212> TYPE: DNA
<213> ORGANISM: Artificial Sequence
<220> FEATURE:
<223> OTHER INFORMATION: Antibody chain

<400> SEQUENCE: 89

```
gaggtgatgc tggtcgagag cggcggcggt ctcgtgcagc caggcggtag cctgcgcctc       60
agctgcaccg ccagcggctt caccttcagc cgcagcgcca tgagctgggt gcgccaagcc      120
ccaggcaagg gcctggagtg ggtggcctac atcagcggcg gcggcggcga cacctactac      180
agcgtcagcg tgaagggccg cttcaccatc agccgcgaca cgccaagaa cagcctgtac      240 ctgcaaatga acagcctgcg cgccgaggac accgccgtgt actactgcgc ccgccacagc      300
aactacaact actacgccat ggactactgg ggccagggca ccctggtgac cgtgagcagc      360
gcctccacaa agggcccttc cgtgttcccc ctggcccctt gctccggtc cacctccgag      420 tctaccgccg ctctgggctg cctggtcaag gactacttcc ccgagcccgt gaccgtgtcc      480
tggaactctg gcgccctgac ctccggcgtg cacaccttcc ctgctgtgct gcagtcctcc      540
```

```
ggcctgtact ccctgtcctc cgtcgtgacc gtgccctcct ctagcctggg caccaagacc    600
tacacctgta acgtggacca caagccctcc aacaccaagg tggacaagcg ggtggaatct    660
aagtacggcc ctccctgccc ccctgccct gcccctgaat ttctgggcgg accctccgtg    720
ttcctgttcc ccccaaagcc caaggacacc ctgatgatct cccggacccc cgaagtgacc    780
tgcgtggtgg tggacgtgtc ccaggaagat cccgaggtcc agtttaattg gtacgtggac    840
ggcgtggaag tgcacaacgc caagaccaag cccagagagg aacagttcaa ctccacctac    900
cgggtggtgt ccgtgctgac cgtgctgcac caggactggc tgaacggcaa agagtacaag    960
tgcaaggtgt ccaacaaggg cctgcccctc agcatcgaaa agaccatctc caaggccaag   1020
ggccagcccc gcgagcccca ggtgtacacc ctgcctccaa gccaggaaga gatgaccaag   1080
aaccaggtgt ccctgacctg tctggtcaag ggcttctacc cctccgatat cgccgtggaa   1140
tgggagtcca acggccagcc cgagaacaac tacaagacca cccccctgt gctggactcc   1200 gacggctcct tcttcctgta ctctcggctg accgtggaca gtcccggtg caggaaggc   1260 aacgtcttct cctgctccgt gatgcacgag gccctgcaca accactacac ccagaagtcc   1320
ctgtccctga gcctgggc                                                 1338

<210> SEQ ID NO 90
<211> LENGTH: 654
<212> TYPE: DNA
<213> ORGANISM: Artificial Sequence
<220> FEATURE:
<223> OTHER INFORMATION: Antibody chain

<400> SEQUENCE: 90
gagatcgtgc tgacccagag cccagccacc ctaagcctga gcccaggcga gcgcgccacc     60
atgagctgcc gcgccagcga gaacatcgac cacagcggca tcagcttcat gaactggtac    120
cagcagaagc caggccaggc cccaaagctg ctgatctacg tggccagcaa ccagggcagc    180
ggcatcccag cccgcttcag cggcagcggc agcggcaccg acttcaccct gaccatcagc    240
cgcctggagc cagaggactt cgccgtgtac tactgccagc agagcaagga agtcccatgg    300
accttcggcc aaggtactaa gctggagatc aagcgtactg tggctgcacc atctgtcttc    360
atcttcccgc catctgatga gcaattgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca caggggaga gtgt            654

<210> SEQ ID NO 91
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 91
caggtcaccc tgaaggagag cggcccaacc ctggtgaagc caacccagac cctgaccctg     60
acctgcagct tcagcggctt ctccctgagc accagcgaca tgggcgtggg ctggattcgc    120
caaccaccag gcaaggccct ggagtggctg gcccacatct ggtgggacga cgtgaagcgc    180
tacaacccag ccctgaagag ccgcctgacc atcaccaagg acaccagcaa gaaccaggtg    240
gtgctgacca tgacc                                                     255
```

```
<210> SEQ ID NO 92
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 92
gacatccaga tgacccagag ccctagcttc ctgagcgcca gcgtcggcga ccgcgtgacc    60
ttcacctgca aggccagcca ggacgtgagc accgccgtcg cctggtatca gcagaagcct   120
ggcaaggccc caaagctgct gatctacagc gccagctacc gctacaccgg cgtgccagac   180
cgcttcagcg gcagcggcag cggcaccgac ttcaccctga ccatcagcag cctgcaacca   240
gaggacttcg ccacc                                                   255

<210> SEQ ID NO 93
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 93
caggtgaccc tggtggagag cggcggcggc gtcgtgcagc caggccgcag cctgagcctg    60
agctgcgctt tcagcggctt cagcctcagc accagcgaca tgggcgtggg ctgggtccgc   120
caaccaccag gcaagggcct ggagtgggtg cccacatct ggtgggacga cgtgaagcgc   180
tacaacccag ccctgaagag ccgctttacc atcagccgcg acaacagcaa gaacaccctg   240
tacctgcaaa tgaac                                                   255

<210> SEQ ID NO 94
<211> LENGTH: 254
<212> TYPE: DNA
<213> ORGANISM: Artificial Sequence
<220> FEATURE:
<223> OTHER INFORMATION: Immunoglobulin domain

<400> SEQUENCE: 94
acatccagat gacccagagc cctagcttcc tgagcgccag cgtcggcgac cgcgtgacga    60
tcacctgcaa ggccagccag gacgtgagca ccgccgtcgc ctggtatcag cagaagcctg   120
gcaaggcccc aaagctgctg atctacagcg ccagctaccg ctacaccggc gtgccagacc   180
gcttcagcgg cagcggcagc ggcaccgact tcaccctgac catcagcagc ctgcaaccag   240
aggacttcgc cacc                                                    254

<210> SEQ ID NO 95
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 95
caggtgaccc tggtggagag cggcggcggc gtcgtgcagc caggccgcag cctgcgcctg    60
agctgcgctt tcagcggctt cagcctcagc accagcgaca tgggcgtggg ctggatccgc   120
caagccccag gcaagggcct ggagtgggtg cccacatct ggtgggacga cgtgaagcgc   180
tacaacccag ccctgaagag ccgctttacc atcagccgcg acaacagcaa gaacaccctg   240
```
tacctgcaaa tgaac                                                       255

<210> SEQ ID NO 96
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 96
gacatcgtga tgacccagag ccctagcttc ctgagcgcca gcgtcggcga ccgcgtgacc        60
atcacctgca aggccagcca ggacgtgagc accgccgtcg cctggtatca gcagaagcct       120
ggcaaggccc caaagctgct gatctacagc gccagctacc gctacaccgg cgtgccagac       180
cgcttcagcg gcagcggcag cggcaccgac ttcaccctga ccatcagcag cctgcaacca       240
gaggacttcg ccacc                                                       255

<210> SEQ ID NO 97
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 97
caggtgaccc tggtggagag cggcggcggc gtcgtgcagc caggccgcag cctgcgcctg        60
agctgcgctt tcagcggctt cagcctcagc accagcgaca tgggcgtggg ctggatccgc       120
caagccccag gcaagggcct ggagtgggtg gcccacatct ggtgggacga cgtgaagcgc       180
tacaacccag ccctgaagag ccgctttacc atcagccgcg acaacagcaa gaacaccctg       240
tacctgcaaa tgaac                                                       255

<210> SEQ ID NO 98
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 98
gacatccaga tgacccagag ccctagcttc ctgagcgcca gcgtcggcga ccgcgtgagc        60
atcacctgca aggccagcca ggacgtgagc accgccgtcg cctggtatca gcagaagcct       120
ggcaaggccc caaagctgct gatctacagc gccagctacc gctacaccgg cgtgccagac       180
cgcttcagcg gcagcggcag cggcaccgac ttcaccctga ccatcagcag cctgcaacca       240
gaggacttcg ccacc                                                       255

<210> SEQ ID NO 99
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 99
caggtcaccc tgaaggagag cggcccaacc ctggtgaagc caacccagac cctgaccctg        60
acctgcagct tcagcggctt ctcccctgagc accagcgaca tgggcgtggg ctggattcgc       120
caaccaccag gcaaggccct ggagtggctg gcccacatct ggtgggacga cgtgaagcgc       180
tacaacccag ccctgaagag ccgcctgacc atcaccaagg acaccagcaa gaaccaggtg       240

```
gtgctgacca tgacc                                                      255

<210> SEQ ID NO 100
<211> LENGTH: 255
<212> TYPE: DNA
<213> ORGANISM: Artificial Sequence
<220> FEATURE:
<223> OTHER INFORMATION: Immunoglobulin domain

<400> SEQUENCE: 100
gacatccaga tgacccagag ccctagcttc ctgagcgcca gcgtcggcga ccgcgtgagc       60
atcacctgca aggccagcca ggacgtgagc accgccgtcg cctggtatca gcagaagcct      120
ggcaaggccc caaagctgct gatctacagc gccagctacc gctacaccgg cgtgccagac      180
cgcttcagcg gcagcggcag cggcaccgac ttcaccctga ccatcagcag cctgcaacca      240
gaggacttcg ccgtg                                                      255

<210> SEQ ID NO 101
<211> LENGTH: 1344
<212> TYPE: DNA
<213> ORGANISM: Artificial Sequence
<220> FEATURE:
<223> OTHER INFORMATION: Antibody chain

<400> SEQUENCE: 101
caggtcaccc tgaaggagag cggcccaacc ctggtgaagc aacccagac cctgaccctg        60 acctgcagct tcagcggctt ctccctgagc accagcgaca tgggcgtggg ctggattcgc      120
caaccaccag gcaaggccct ggagtggctg gcccacatct ggtgggacga cgtgaagcgc      180
tacaacccag ccctgaagag ccgcctgacc atcaccaagg acaccagcaa gaaccaggtg      240
gtgctgacca tgaccaacat ggacccagtg acaccgcca cctacttctg cgcccgcatc       300
gaggactacg gcgtgagcta ctacttcgac tactggggcc agggcaccac cgtgaccgtg      360
agcagcgcct ccacaaaggg cccttccgtg ttccccctgg ccccttgctc ccggtccacc      420
tccgagtcta ccgccgctct gggctgcctg gtcaaggact acttcccga gcccgtgacc       480 gtgtcctgga actctggcgc cctgaccctc ggcgtgcaca ccttccctgc tgtgctgcag      540
tcctccggcc tgtactccct gtcctccgtc gtgaccgtgc cctcctctag cctgggcacc      600
aagacctaca cctgtaacgt ggaccacaag ccctccaaca ccaaggtgga caagcgggtg      660
gaatctaagt acggccctcc ctgcccccc tgccctgccc ctgaatttct gggcggaccc       720
tccgtgttcc tgttcccccc aaagccccaag gacaccctga tgatctcccg gacccccgaa     780
gtgacctgcg tggtggtgga cgtgtcccag gaagatcccg aggtccagtt taattggtac      840
gtggacggcg tggaagtgca caacgccaag accaagccca gagaggaaca gttcaactcc      900
acctaccggg tggtgtccgt gctgaccgtg ctgcaccagg actggctgaa cggcaaagag      960
tacaagtgca aggtgtccaa caagggcctg cctccagca tcgaaaagac catctccaag      1020
gccaagggcc agccccgcga gccccaggtg tacaccctgc ctccaagcca ggaagagatg     1080
accaagaacc aggtgtccct gacctgtctg gtcaagggct tctacccctc cgatatcgcc     1140
gtggaatggg agtccaacgg ccagcccgag aacaactaca gaccacccc cctgtgctg       1200 gactccgacg gctccttctt cctgtactct cggctgaccg tggacaagtc ccggtggcag     1260
gaaggcaacg tcttctcctg ctccgtgatg cacgaggccc tgcacaacca ctacacccag     1320
aagtccctgt ccctgagcct gggc                                            1344
```

<210> SEQ ID NO 102
<211> LENGTH: 642
<212> TYPE: DNA
<213> ORGANISM: Artificial Sequence
<220> FEATURE:
<223> OTHER INFORMATION: Antibody chain

<400> SEQUENCE: 102

```
gacatccaga tgacccagag ccctagcttc ctgagcgcca gcgtcggcga ccgcgtgacc    60
ttcacctgca aggccagcca ggacgtgagc accgccgtcg cctggtatca gcagaagcct   120
ggcaaggccc caaagctgct gatctacagc gccagctacc gctacaccgg cgtgccagac   180
cgcttcagcg gcagcggcag cggcaccgac ttcaccctga ccatcagcag cctgcaacca   240
gaggacttcg ccacctacta ctgccagcag cactacagca tcccactgac ctttggccag   300
ggcaccaagc tggagatcaa gcgtactgtg gctgcaccat ctgtcttcat cttcccgcca   360
tctgatgagc aattgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gt                      642
```

<210> SEQ ID NO 103
<211> LENGTH: 1344
<212> TYPE: DNA
<213> ORGANISM: Artificial Sequence
<220> FEATURE:
<223> OTHER INFORMATION: Antibody chain

<400> SEQUENCE: 103

```
caggtgaccc tggtggagag cggcggcggc gtcgtgcagc caggccgcag cctgagcctg    60
agctgcgctt tcagcggctt cagcctcagc accagcgaca tgggcgtggg ctgggtccgc   120
caaccaccag gcaagggcct ggagtgggtg gcccacatct ggtgggacga cgtgaagcgc   180
tacaacccag ccctgaagag ccgctttacc atcagccgcg acaacagcaa gaacaccctg   240
tacctgcaaa tgaacagcct gcgcgccgag gacaccgcca cctactactg cgcccgcatc   300
gaggactacg gcgtgagcta ctacttcgac tactgggcc agggcaccac cgtgaccgtg   360
agcagcgcct ccacaaaggg cccttccgtg ttccccctgg ccccttgctc ccggtccacc   420
tccgagtcta ccgccgctct gggctgcctg gtcaaggact acttccccga gcccgtgacc   480
gtgtcctgga actctggcgc cctgacctcc ggcgtgcaca ccttccctgc tgtgctgcag   540
tcctccggcc tgtactccct gtcctccgtc gtgaccgtgc cctcctctag cctgggcacc   600
aagacctaca cctgtaacgt ggaccacaag ccctccaaca ccaaggtgga caagcgggtg   660
gaatctaagt acggcccctcc ctgcccccc tgccctgccc ctgaatttct gggcggaccc   720
tccgtgttcc tgttccccccc aaagcccaag gacaccctga tgatctcccg gacccccgaa   780
gtgacctgcg tggtggtgga cgtgtcccag gaagatcccg aggtccagtt taattggtac   840
gtggacggcg tggaagtgca caacgccaag accaagccca gaggaacaa gttcaactcc   900
acctaccggg tggtgtccgt gctgaccgtg ctgcaccagg actggctgaa cggcaaagag   960
tacaagtgca aggtgtccaa caaggggcctg cctccagca tcgaaaagac catctccaag  1020
gccagggcc agccccgcga gccccaggtg tacaccctgc ctccaagcca ggaagagatg  1080
accaagaacc aggtgtccct gacctgtctg gtcaagggct tctacccctc cgatatcgcc  1140
```

```
gtggaatggg agtccaacgg ccagcccgag aacaactaca agaccacccc ccctgtgctg      1200
gactccgacg gctccttctt cctgtactct cggctgaccg tggacaagtc ccggtggcag      1260
gaaggcaacg tcttctcctg ctccgtgatg cacgaggccc tgcacaacca ctacacccag      1320
aagtccctgt ccctgagcct gggc                                             1344

<210> SEQ ID NO 104
<211> LENGTH: 642
<212> TYPE: DNA
<213> ORGANISM: Artificial Sequence
<220> FEATURE:
<223> OTHER INFORMATION: Antibody chain

<400> SEQUENCE: 104
gacatccaga tgacccagag ccctagcttc ctgagcgcca gcgtcggcga ccgcgtgacg       60
atcacctgca aggccagcca ggacgtgagc accgccgtcg cctggtatca gcagaagcct      120
ggcaaggccc caaagctgct gatctacagc gccagctacc gctacaccgg cgtgccagac      180
cgcttcagcg gcagcggcag cggcaccgac ttcaccctga ccatcagcag cctgcaacca      240
gaggacttcg ccacctacta ctgccagcag cactacagca tcccactgac ctttggcgcc      300
ggcaccaagc tggagatcaa gcgtactgtg gctgcaccat ctgtcttcat cttcccgcca      360
tctgatgagc aattgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642

<210> SEQ ID NO 105
<211> LENGTH: 1344
<212> TYPE: DNA
<213> ORGANISM: Artificial Sequence
<220> FEATURE:
<223> OTHER INFORMATION: Antibody chain

<400> SEQUENCE: 105
caggtgaccc tggtggagag cggcggcggc gtcgtgcagc caggccgcag cctgcgcctg       60
agctgcgctt tcagcggctt cagcctcagc accagcgaca tgggcgtggg ctggatccgc      120 caagcccag gcaagggcct ggagtgggtg gcccacatct ggtgggacga cgtgaagcgc      180
tacaacccag ccctgaagag ccgctttacc atcagccgcg acaacagcaa gaacaccctg      240
tacctgcaaa tgaacagcct gcgcgccgag gacaccgcca cctacttctg cgcccgcatc      300
gaggactacg gcgtgagcta ctacttcgac tactggggcc agggcaccac cgtgaccgtg      360
agcagcgcct ccacaaaggg cccttccgtg ttccccctgg ccccttgctc ccggtccacc      420
tccgagtcta ccgccgctct gggctgcctg gtcaaggact acttcccga gcccgtgacc      480 gtgtcctgga actctggcgc cctgaccctcc ggcgtgcaca ccttccctgc tgtgctgcag      540
tcctccggcc tgtactccct gtcctccgtc gtgaccgtgc cctcctctag cctgggcacc      600
aagacctaca cctgtaacgt ggaccacaag ccctccaaca ccaaggtgga caagcgggtg      660
gaatctaagt acggcccctcc ctgccccccc tgccctgccc ctgaatttct gggcggaccc      720
tccgtgttcc tgttccccccc aaagcccaag gacaccctga tgatctcccg gacccccgaa      780
gtgacctgcg tggtggtgga cgtgtcccag gaagatcccg aggtccagtt taattggtac      840
```

```
gtggacggcg tggaagtgca caacgccaag accaagccca gagaggaaca gttcaactcc    900
acctaccggg tggtgtccgt gctgaccgtg ctgcaccagg actggctgaa cggcaaagag    960
tacaagtgca aggtgtccaa caagggcctg ccctccagca tcgaaaagac catctccaag   1020
gccaagggcc agccccgcga gccccaggtg tacaccctgc ctccaagcca ggaagagatg   1080
accaagaacc aggtgtccct gacctgtctg gtcaagggct ctacccctc cgatatcgcc    1140 gtggaatggg agtccaacgg ccagcccgag aacaactaca agaccacccc ccctgtgctg   1200
gactccgacg gctccttctt cctgtactct cggctgaccg tggacaagtc ccggtggcag   1260
gaaggcaacg tcttctcctg ctccgtgatg cacgaggccc tgcacaacca ctacacccag   1320
aagtccctgt ccctgagcct gggc                                          1344
```

<210> SEQ ID NO 106
<211> LENGTH: 642
<212> TYPE: DNA
<213> ORGANISM: Artificial Sequence
<220> FEATURE:
<223> OTHER INFORMATION: Antibody chain

<400> SEQUENCE: 106

```
gacatcgtga tgacccagag ccctagcttc ctgagcgcca gcgtcggcga ccgcgtgacc     60
atcacctgca aggccagcca ggacgtgagc accgccgtcg cctggtatca gcagaagcct    120
ggcaaggccc caaagctgct gatctacagc gccagctacc gctacaccgg cgtgccagac    180
cgcttcagcg gcagcggcag cggcaccgac ttcaccctga ccatcagcag cctgcaacca    240
gaggacttcg ccacctacta ctgccagcag cactacagca tcccactgac ctttggccag    300
ggcaccaagc tggagatcaa gcgtactgtg gctgcaccat ctgtcttcat cttcccgcca    360
tctgatgagc aattgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg    540 ctgagcaaag cagactacga aaacacaaa gtctacgcct gcgaagtcac ccatcagggc    600
ctgagctcgc ccgtcacaaa gagcttcaac aggggagagt gt                      642
```

<210> SEQ ID NO 107
<211> LENGTH: 1344
<212> TYPE: DNA
<213> ORGANISM: Artificial Sequence
<220> FEATURE:
<223> OTHER INFORMATION: Antibody chain

<400> SEQUENCE: 107

```
caggtgaccc tggtggagag cggcggcggc gtcgtgcagc caggccgcag cctgcgcctg     60
agctgcgctt tcagcggctt cagcctcagc accagcgaca tgggcgtggg ctggatccgc    120
caagccccag gcaagggcct ggagtgggtg gcccacatct ggtgggacga cgtgaagcgc    180
tacaacccag ccctgaagag ccgctttacc atcagccgcg acaacagcaa gaacaccctg    240
tacctgcaaa tgaacagcct gcgcgccgag gacaccgccg tgtacttctg cgcccgcatc    300
gaggactacg gcgtgagcta ctacttcgac tactggggcc agggcaccac cgtgaccgtg    360
agcagcgcct ccacaaaggg cccttccgtg ttccccctgg ccccttgctc ccggtccacc    420
tccgagtcta ccgccgctct gggctgcctg gtcaaggact acttccccga gcccgtgacc    480
gtgtcctgga actctggcgc cctgaccctc ggcgtgcaca ccttccctgc tgtgctgcag    540
tcctccggcc tgtactccct gtcctccgtc gtgaccgtgc cctcctctag cctgggcacc    600
```

```
aagacctaca cctgtaacgt ggaccacaag ccctccaaca ccaaggtgga caagcgggtg      660
gaatctaagt acggccctcc ctgccccccc tgccctgccc ctgaatttct gggcggaccc      720
tccgtgttcc tgttccccccc aaagcccaag acaccctga tgatctcccg accccgaa       780 gtgacctgcg tggtggtgga cgtgtcccag aagatcccg aggtccagtt taattggtac       840
gtggacggcg tggaagtgca caacgccaag accaagccca gagaggaaca gttcaactcc     900
acctaccggg tggtgtccgt gctgaccgtg ctgaccagg actggctgaa cggcaaagag      960
tacaagtgca aggtgtccaa caagggcctg ccctccagca tcgaaaagac catctccaag    1020
gccaagggcc agccccgcga gccccaggtg tacaccctgc ctccaagcca ggaagagatg    1080
accaagaacc aggtgtccct gacctgtctg gtcaagggct tctaccccte cgatatcgcc    1140 gtggaatggg agtccaacgg ccagcccgag aacaactaca agaccacccc ccctgtgctg    1200
gactccgacg gctccttctt cctgtactct cggctgaccg tggacaagtc ccggtggcag    1260
gaaggcaacg tcttctcctg ctccgtgatg cacgaggccc tgcacaacca ctacacccag    1320
aagtccctgt ccctgagcct gggc                                            1344
```

<210> SEQ ID NO 108
<211> LENGTH: 642
<212> TYPE: DNA
<213> ORGANISM: Artificial Sequence
<220> FEATURE:
<223> OTHER INFORMATION: Antibody chain

<400> SEQUENCE: 108

```
gacatccaga tgacccagag ccctagcttc ctgagcgcca gcgtcggcga ccgcgtgagc       60
atcacctgca aggccagcca ggacgtgagc accgccgtcg cctggtatca gcagaagcct     120
ggcaaggccc caaagctgct gatctacagc gccagctacc gctacaccgg cgtgccagac     180
cgcttcagcg gcagcggcag cggcaccgac ttcaccctga ccatcagcag cctgcaacca     240
gaggacttcg ccacctacta ctgccagcag cactacagca tcccactgac cttggccag     300 ggcaccaagc tggagatcaa gcgtactgtg gctgcaccat ctgtcttcat cttccgcca     360 tctgatgagc aattgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 109
<211> LENGTH: 1344
<212> TYPE: DNA
<213> ORGANISM: Artificial Sequence
<220> FEATURE:
<223> OTHER INFORMATION: Antibody chain

<400> SEQUENCE: 109

```
caggtcaccc tgaaggagag cggcccaacc ctggtgaagc caacccagac cctgaccctg       60
acctgcagct tcagcggctt ctccctgagc accagcgaca tgggcgtggg ctggattcgc     120
caaccaccag gcaaggccct ggagtggctg gcccacatct ggtgggacga cgtgaagcgc     180
tacaacccag ccctgaagag ccgcctgacc atcaccaagg acaccagcaa gaaccaggtg     240
gtgctgacca tgaccaacat ggaccagtg gacaccgcca cctacttctg cgcccgcatc     300
```

| | |
|---|---|
| gtggactacg gcgtgagcta ctacttcgac tactggggcc agggcaccac cgtgaccgtg | 360 |
| agcagcgcct ccacaaaggg cccttccgtg ttcccctgg cccttgctc ccggtccacc | 420 |
| tccgagtcta ccgccgctct gggctgcctg gtcaaggact acttccccga gcccgtgacc | 480 |
| gtgtcctgga actctggcgc cctgaccctc ggcgtgcaca ccttccctgc tgtgctgcag | 540 |
| tcctccggcc tgtactccct gtcctccgtc gtgaccgtgc cctcctctag cctgggcacc | 600 |
| aagacctaca cctgtaacgt ggaccacaag ccctccaaca ccaaggtgga caagcgggtg | 660 |
| gaatctaagt acggccctcc ctgcccccc tgccctgccc ctgaatttct gggcggaccc | 720 |
| tccgtgttcc tgttccccc aaagcccaag gacaccctga tgatctcccg gacccccgaa | 780 |
| gtgacctgcg tggtggtgga cgtgtcccag gaagatcccg aggtccagtt taattggtac | 840 |
| gtggacggcg tggaagtgca caacgccaag accaagccca gaggaaca gttcaactcc | 900 |
| acctaccggg tggtgtccgt gctgaccgtg ctgcaccagg actggctgaa cggcaaagag | 960 |
| tacaagtgca aggtgtccaa caagggcctg ccctccagca tcgaaaagac catctccaag | 1020 |
| gccaagggcc agccccgcga gccccaggtg tacaccctgc ctccaagcca ggaagagatg | 1080 |
| accaagaacc aggtgtccct gacctgtctg gtcaagggct ctaccctc cgatatcgcc | 1140 |
| gtggaatggg agtccaacgg ccagcccgag aacaactaca gaccacccc cctgtgctg | 1200 |
| gactccgacg gctccttctt cctgtactct cggctgaccg tggacaagtc ccggtggcag | 1260 |
| gaaggcaacg tcttctcctg ctccgtgatg cacgaggccc tgcacaacca ctacacccag | 1320 |
| aagtccctgt ccctgagcct gggc | 1344 |

<210> SEQ ID NO 110
<211> LENGTH: 642
<212> TYPE: DNA
<213> ORGANISM: Artificial Sequence
<220> FEATURE:
<223> OTHER INFORMATION: Antibody chain

<400> SEQUENCE: 110

| | |
|---|---|
| gacatccaga tgacccagag ccctagcttc ctgagcgcca gcgtcggcga ccgcgtgagc | 60 |
| atcacctgca aggccagcca ggacgtgagc accgccgtcg cctggtatca gcagaagcct | 120 |
| ggcaaggccc caaagctgct gatctacagc gccagctacc gctacaccgg cgtgccagac | 180 |
| cgcttcagcg gcagcggcag cggcaccgac ttcaccctga ccatcagcag cctgcaacca | 240 |
| gaggacttcg ccgtgtacta ctgccagcag cactacagca tcccactgac ctttggccag | 300 |
| ggcaccaagc tggagatcaa gcgtactgtg gctgcaccat ctgtcttcat cttcccgcca | 360 |
| tctgatgagc aattgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 111
<211> LENGTH: 8
<212> TYPE: PRT
<213> ORGANISM: Artificial Sequence
<220> FEATURE:
<223> OTHER INFORMATION: Epitope sequence

<400> SEQUENCE: 111

Leu Leu Arg Arg Ala Gly Val Thr

```
1               5
```

<210> SEQ ID NO 112
<211> LENGTH: 11
<212> TYPE: PRT
<213> ORGANISM: Artificial Sequence
<220> FEATURE:
<223> OTHER INFORMATION: Epitope sequence

<400> SEQUENCE: 112

```
Tyr Arg Ala Ala Val His Leu Arg Asp Arg Ala
1               5                   10
```

<210> SEQ ID NO 113
<211> LENGTH: 111
<212> TYPE: PRT
<213> ORGANISM: Artificial Sequence
<220> FEATURE:
<223> OTHER INFORMATION: Immunoglobulin domain

<400> SEQUENCE: 113

```
Asp Ile Val Leu Thr Gln Ser Pro Ala Ser Leu Ala Val Ser Leu Gly
1               5                   10                  15

Gln Arg Ala Thr Met Ser Cys Arg Ala Ser Glu Asn Ile Asp Asn Ser
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Asn Gln Gly Ser Gly Val Pro Ala
    50                  55                  60

Arg Phe Ser Gly Ser Gly Ser Gly Thr Asp Phe Arg Leu Thr Ile His
65                  70                  75                  80

Pro Leu Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110
```

<210> SEQ ID NO 114
<211> LENGTH: 120
<212> TYPE: PRT
<213> ORGANISM: Artificial Sequence
<220> FEATURE:
<223> OTHER INFORMATION: Immunoglobulin domain

<400> SEQUENCE: 114

```
Glu Val Met Leu Val Glu Ser Gly Gly Gly Leu Val Lys Pro Gly Gly
1               5                   10                  15

Ser Leu Lys Leu Ser Cys Thr Ala Ser Gly Phe Thr Phe Ser Asn Ser
            20                  25                  30

Ala Met Ser Trp Val Arg Gln Thr Pro Glu Arg Arg Leu Glu Trp Val
        35                  40                  45

Ala Tyr Ile Ser Gly Gly Gly Asp Thr Tyr Tyr Ser Asp Ser Val
    50                  55                  60

Lys Gly Arg Phe Thr Ile Ser Arg Asp Asn Ala Lys Asp Thr Leu Tyr
65                  70                  75                  80

Leu His Met Ser Ser Leu Arg Ser Glu Asp Thr Ala Leu His Tyr Cys
                85                  90                  95

Ala Arg His Ser Asn Ser Asn Tyr Tyr Ala Met Asp Tyr Trp Gly Gln
            100                 105                 110

Gly Thr Ser Val Thr Val Ser Ser
            115                 120
```

<210> SEQ ID NO 115
<211> LENGTH: 14
<212> TYPE: PRT
<213> ORGANISM: Artificial Sequence
<220> FEATURE:
<223> OTHER INFORMATION: Epitope sequence

<400> SEQUENCE: 115

Ala Ile Ser Leu Ala Pro Lys Ala Gln Ile Lys Glu Ser Leu
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Epitope sequence

<400> SEQUENCE: 116

Ala Ala Phe Pro Glu Asp Arg Ser Gln Pro Gly Gln Asp Cys Arg Phe
1               5                   10                  15

<210> SEQ ID NO 117
<211> LENGTH: 107
<212> TYPE: PRT
<213> ORGANISM: Artificial Sequence
<220> FEATURE:
<223> OTHER INFORMATION: Immunoglobulin domain

<400> SEQUENCE: 117

Asp Ile Val Met Thr Gln Ser His Lys Phe Met Ser Thr Ser Val Gly
1               5                   10                  15

Asp Arg Val Ser Phe Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Ile Pro Leu
                85                  90                  95

Thr Phe Gly Ala Gly Thr Lys Leu Glu Leu Lys
            100                 105

<210> SEQ ID NO 118
<211> LENGTH: 122
<212> TYPE: PRT
<213> ORGANISM: Artificial Sequence
<220> FEATURE:
<223> OTHER INFORMATION: Immunoglobulin domain

<400> SEQUENCE: 118

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asp Met Gly Val Gly Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
    50                  55                  60

-continued

```
Leu Lys Ser Arg Leu Thr Ile Ser Lys Asp Thr Ser Ser Ser Gln Val
65              70                  75                  80

Phe Leu Met Ile Ala Ser Val Asp Thr Ala Asp Thr Ala Thr Tyr Phe
            85                  90                  95

Cys Ala Arg Ile Glu Asp Tyr Gly Val Ser Tyr Tyr Phe Asp Tyr Trp
            100                 105                 110

Gly Gln Gly Thr Thr Leu Thr Val Ser Ser
        115             120
```

ANTIBODY MOLECULES FOR CANCER TREATMENT

FIELD OF THE INVENTION

The present invention relates to novel anti-PD1 and anti-LAG3 antibody molecules. The invention also relates to nucleic acids encoding such antibody molecules; to methods for preparing such antibody molecules; to host cells expressing or capable of expressing such antibody molecules; to compositions comprising such antibody molecules; and to uses of such antibody molecules or such compositions, in particular for therapeutic purposes in the field of cancer diseases.

BACKGROUND OF THE INVENTION

Cancer is a disease characterised by abnormal localised cell growth with the potential to spread throughout the body. In the developed world it is the second most common cause of death. The most common types of cancer in males are lung cancer, prostate cancer, colorectal cancer, and stomach cancer, and in females, the most common types are breast cancer, colorectal cancer, lung cancer, and cervical cancer. While the chances of survival depends mainly on the type of cancer and the stage at identification, for lung cancer the overall 10 year survival rate is around 5%.

In the past the most frequent means of treating tumorous cancers (termed 'oncology') are through surgery, radiation treatment, or the use of chemotherapeutic drugs. However, in recent years, cancer immunotherapy has shown to offer much promise as a treatment modality for oncology.

Cancer immunotherapy is a branch of oncology in which the immune system is used to treat cancer, which is in stark contrast to existing common methods of treatment in which the tumor is directly excised or treated. This therapeutic concept is based on the identification of a number of proteins on the surface of T-cells which act to inhibit the immune function of these cells. Listed among these proteins is PD1.

PD1 (Programmed cell death 1) is a cell surface receptor protein expressed on T-cells. The protein functions as an "immune checkpoint" inhibitor, i.e. it acts to modulate the activity of cells in the immune system so as to regulate and limit autoimmune diseases. It has been recently understood that many cancers can protect themselves from the immune system by modifying "immune checkpoint" inhibitors and thus avoid detection.

With respect to PD1, this protein has two ligands, PD-L1 and PD-L2, which interact with the cell surface receptor. On binding, PD-1 induced an intracellular signal which negatively regulates T-cell response.

As detailed above, PD1 is a key regulator of T-cell activity. Recently it has been shown in a range of different cancer settings that the antagonistic PD-1 antibodies molecules nivolumab and pembrolizumab can be used to stimulate the immune system and thereby treat cancer.

Lymphocyte activation gene-3 (LAG3; CD223) is a type I transmembrane protein mainly expressed on the cell surface of activated T cells but also found on subsets of NK and dendritic cells LAG3 is closely related to CD4, which is a co-receptor for T helper cell activation. Both molecules have four extracellular Ig-like domains and require binding to their ligand, major histocompatibility complex (MHC) class II, for their functional activity. On binding to MHC-II, LAG3 induced an intracellular signal which negatively regulates T-cell response. Recent studies have revealed that LAG3 and PD1 are co-expressed on tumor infiltrating lymphocytes (TILs) suggesting that they may contribute to tumor-mediated immune suppression. It is thought that chronic exposure to antigens leads to a progressive inactivation of T cells through a process termed "exhaustion". Exhausted T cells often co-express negative regulatory receptors such as PD1 and LAG3.

Despite encouraging clinical results of PD1 antagonistic monoclonal antibodies nivolumab and pembrolizumab, up to 70% of treated patients do not respond to treatment. Preclinical data with patient-derived T cells as well as from syngeneic tumor mouse models have demonstrated that tumor-derived T cells frequently express other inhibitory receptors in addition to PD1. Combined neutralization of PD1 and LAG3 using antagonistic monoclonal antibody molecules increased reactivation of T cells and improved tumor rejection compared to PD1 neutralization alone, in in vitro and in vivo models. Based on these results, it is expected that neutralization of LAG3 will enhance the efficacy of antagonistic PD1 mAbs.

However, existing anti-PD1 antibody molecules suffer from problems associated with the failure of a large proportion of patients to respond to treatment. There is therefore a need to identify more efficacious PD1 antagonistic monoclonal antibodies with manageable side effect profiles when compared to the prior art existing antibody medicaments when used alone or in combination with other therapeutic molecules, particularly additional antagonistic molecules to further T-cell checkpoint inhibitors.

From this background, the inventors sought to generate further anti-PD1 and anti-LAG3 antibodies having improved therapeutic profile over the known molecules.

BRIEF SUMMARY OF THE INVENTION

According to a first aspect there are provided anti-PD1 antibody molecules. As described further herein, the anti-PD1 antibody molecules of the present invention have surprising and advantageous properties over other anti-PD1 antibodies. In particular, they demonstrate improved activation of T cells and longer terminal half-life than reference anti-PD1 antibody molecules. As will be appreciated, such properties are desirable for anti-PD1 antibody molecules for use in treating cancers.

Nucleic acid molecules encoding the anti-PD1 antibody molecules, expression vectors, host cells and methods of making the anti-PD1 antibody molecules of the invention are also provided. Pharmaceutical compositions comprising the anti-PD1 antibody molecules of the invention are also provided. The anti-PD-1 antibody molecules disclosed herein can be used to treat cancerous disorders, including solid and soft-tissue tumors.

More specifically, an anti-PD1 antibody molecule of the invention comprises: (a) heavy chain CDRs comprising the amino acid sequence of SEQ ID NO:1 (hcCDR1), SEQ ID NO:2 (hcCDR2) and SEQ ID NO:3 (hcCDR3) and has light chain CDRs comprising the amino acid sequence of SEQ ID NO:4 (lcCDR1), SEQ ID NO:5 (lcCDR2) and SEQ ID NO:6 (lcCDR3); or, b) heavy chain CDRs comprising the amino acid sequence of SEQ ID NO:7 (hcCDR1), SEQ ID NO:8 (hcCDR2) and SEQ ID NO:9 (hcCDR3) and has light chain CDRs comprising the amino acid sequence of SEQ ID NO:10 (lcCDR1), SEQ ID NO:11 (lcCDR2) and SEQ ID NO:12 (lcCDR3); or (c) heavy chain CDRs comprising the amino acid sequence of SEQ ID NO:13 (hcCDR1), SEQ ID NO:14 (hcCDR2) and SEQ ID NO:15 (hcCDR3) and has light chain CDRs comprising the amino acid sequence of SEQ ID NO:16 (lcCDR1), SEQ ID NO:17 (lcCDR2) and SEQ ID NO:18 (lcCDR3).

According to a further aspect of the invention, there is also provided anti-LAG3 antibody molecules. As described further herein, the anti-LAG3 antibody molecules of the present invention have surprising and advantageous properties over other anti-LAG3 antibody molecules. In particular, they demonstrate improved activation of T cells when used in combination with the anti-PD1 antibody molecules of the present invention than reference anti-PD1 antibody molecules and anti-LAG3 antibody molecules. As will be appreciated, such properties are desirable for anti-LAG3 antibody molecules for use in treating cancers.

Nucleic acid molecules encoding the antibody molecules, expression vectors, host cells and methods of making the anti-LAG3 antibody molecules are also provided. Pharmaceutical compositions comprising the anti-LAG3 antibody molecules of the invention are also provided. The anti-LAG3 antibody molecules disclosed herein can be used to treat cancerous disorders, including solid and soft-tissue tumors.

According to a preferred embodiment, an anti-LAG3 antibody molecule of the invention bind an epitope of human LAG3 comprising the amino acid sequence LLR-RAGVT (SEQ ID NO: 111) and/or YRAAVHLRDRA (SEQ ID NO: 112). Methods of determining the epitope to which an antibody binds are provided herein.

According to a preferred embodiment, the anti-LAG3 antibody molecule of the invention comprises (a) heavy chain CDRs comprising the amino acid sequence of SEQ ID NO:39 (hcCDR1), SEQ ID NO:40 (hcCDR2) and SEQ ID NO:41 (hcCDR3) and has light chain CDRs comprising the amino acid sequence of SEQ ID NO:42 (lcCDR1), SEQ ID NO:43 (lcCDR2) and SEQ ID NO:44 (lcCDR3); or (b) heavy chain CDRs comprising the amino acid sequence of SEQ ID NO:45 (hcCDR1), SEQ ID NO:46 (hcCDR2) and SEQ ID NO:47 (hcCDR3) and has light chain CDRs comprising the amino acid sequence of SEQ ID NO:48 (lcCDR1), SEQ ID NO:49 (lcCDR2) and SEQ ID NO:50 (lcCDR3).

According to a further aspect of the invention, there is also provided methods for the treatment of cancers in which anti-PD1 antibody molecules of the invention may be used in combination with the anti-LAG3 antibody molecules of the invention. Embodiments of these aspects of the invention include where the anti-LAG3 antibody is to be administered simultaneously, concurrently, sequentially, successively, alternatively or separately, with the anti-PD1 antibody molecules.

Further embodiments of these aspects of the invention include where the anti-PD1 antibody molecules is to be administered simultaneously, concurrently, sequentially, successively, alternatively or separately, with the anti-LAG3 antibody molecules. Further embodiments of these aspects of the invention include where said uses of the antibody molecules of the invention can be combined with other therapeutic agents.

Further aspects, embodiments, uses and methods involving the antibody molecules of the invention will become clear from the following detailed description of the invention and from the appended claims.

The invention provides for novel antibody molecules that allow a more efficient treatment of several cancer types, such as lung cancer, particularly NSCLC.

BRIEF DESCRIPTION OF THE DRAWINGS

FIGS. 1a and 1b: Amino acid sequences of the variable domain of anti-PD1 antibody molecules. 77E11 is the name of the murine progenitor antibody. PD1-1, PD1-2, PD1-3, PD1-4 and PD1-5 are anti-PD1 antibodies as defined herein. The CDR sequences are underlined. VK 77E11 (SEQ ID NO: 113); VK PD1-1 (SEQ ID NO: 20); VK PD1-2; (SEQ ID NO: 22); VK PD1-3 (SEQ ID NO: 24); VK PD1-4, (SEQ ID NO: 26); VK PD1-5 (SEQ ID NO: 28); VH 77E11 (SEQ ID NO: 114); VH PD1-1 (SEQ ID NO: 19); VH PD1-2; (SEQ ID NO: 21); VH PD1-3 (SEQ ID NO: 23); VH PD1-4, (SEQ ID NO: 25); VH PD1-5 (SEQ ID NO: 27).

FIGS. 2a(A) to 2a(C) show anti-PD1 antibodies of the invention induced blockade of PD-L1 binding to human PD-1 expressed on the surface of CHO cells. FIGS. 2b(D) to 2a((F) show anti-PD1 antibodies of the invention induced blockade of PD-L2 binding to human PD-1 expressed on the surface of CHO cells.

FIGS. 5a and 5b: Preclinical pharmacokinetics of anti-PD1 antibody molecules Pharmacokinetic parameters of PD1 antibodies upon intravenous dosing plotted against doses administered to Cynomolgus monkeys. (FIG. 5a(A)) Area-under-the-curve (AUC), (FIG. 5a(B)) maximum plasma concentration ($c_{max}$), (FIG. 5b(C)), plasma clearance (CL), (FIG. 5b(D)) elimination half-life in terminal phase ($t_{1/2, z}$).

FIGS. 6a and 6b: Amino acid sequences of the variable domain of anti-LAG3 antibody molecules. 496G6 is the name of the murine progenitor antibody. LAG3-1, LAG3-2, LAG3-3, LAG3-4 and LAG3-5 are anti-LAG3 antibodies as defined herein. VK 496G6 (SEQ ID NO: 117); VK LAG3-1 (SEQ ID NO: 52); VK LAG3-2; (SEQ ID NO: 54); VK LAG3-3 (SEQ ID NO: 56); VK LAG3-4, (SEQ ID NO: 58); VK LAG3-5 (SEQ ID NO: 60); VH 496G6 (SEQ ID NO: 118); VH LAG3-1 (SEQ ID NO: 51); VH LAG3-2; (SEQ ID NO: 53); VH LAG3-3 (SEQ ID NO: 55); VH LAG3-4, (SEQ ID NO: 57); VH LAG3-5 (SEQ ID NO: 59).

FIG. 7: Inhibition of human LAG3 binding to MHCII by anti-LAG3 antibody molecules. Shows potency of indicated LAG3 mAbs and control mAbs to block binding of recombinant LAG3 to MHCII expressed on the surface of Raji cells.

FIG. 8: Stimulation of antigen-specific T cell response by anti-PD1 and anti-LAG3 antibody molecules. (A) Shows % fold increase of PD1/LAG3 mAb combinations relative to saturating amounts of pembrolizumab (KEYTRUDA®). Fixed 100 nM concentrations of PD1-3 and nivolumab (OPDIVO®) were combined with increasing amount of LAG3 mAbs (LAG3-1 shown as black line or a reference antibody molecule having the same amino acid sequence as BMS-986016 shown as dotted line, an antagonistic LAG3 antibody). (B) Shows % fold increase of PD1/LAG3 mAb molecules of the invention combinations relative to pembrolizumab (KEYTRUDA®) activity. Level of combination mAb activity was assessed at 100 nM for PD1 and 200 nM for LAG3 mAbs. Statistical testing was performed using Graph Pad Prism by one-way ANOVA followed by Tukey post hoc test.

(FIGS. 9a(A) to 9b(D)) Mice bearing a colon carcinoma (MC38) were treated with PBS, anti-LAG3, anti-PD1 or the combination of anti-PD1 and anti-LAG3. Mice bearing a melanoma (B16-F10) (FIGS. 9c(E) to 9d(G)), lung carcinoma (LL/2) (FIGS. 9e(H) to 9f(J)), colon carcinoma (Colon-26) (FIGS. 9g(K) to 9h(M)) or a breast cancer (4T1) (FIGS. 9i(N) to 9j(P)) tumor were treated with PD1 Isotype, anti-PD1 or the combination of anti-PD1 and anti-LAG3.

DETAILED DESCRIPTION OF THE INVENTION

Definitions

Figure 2A:
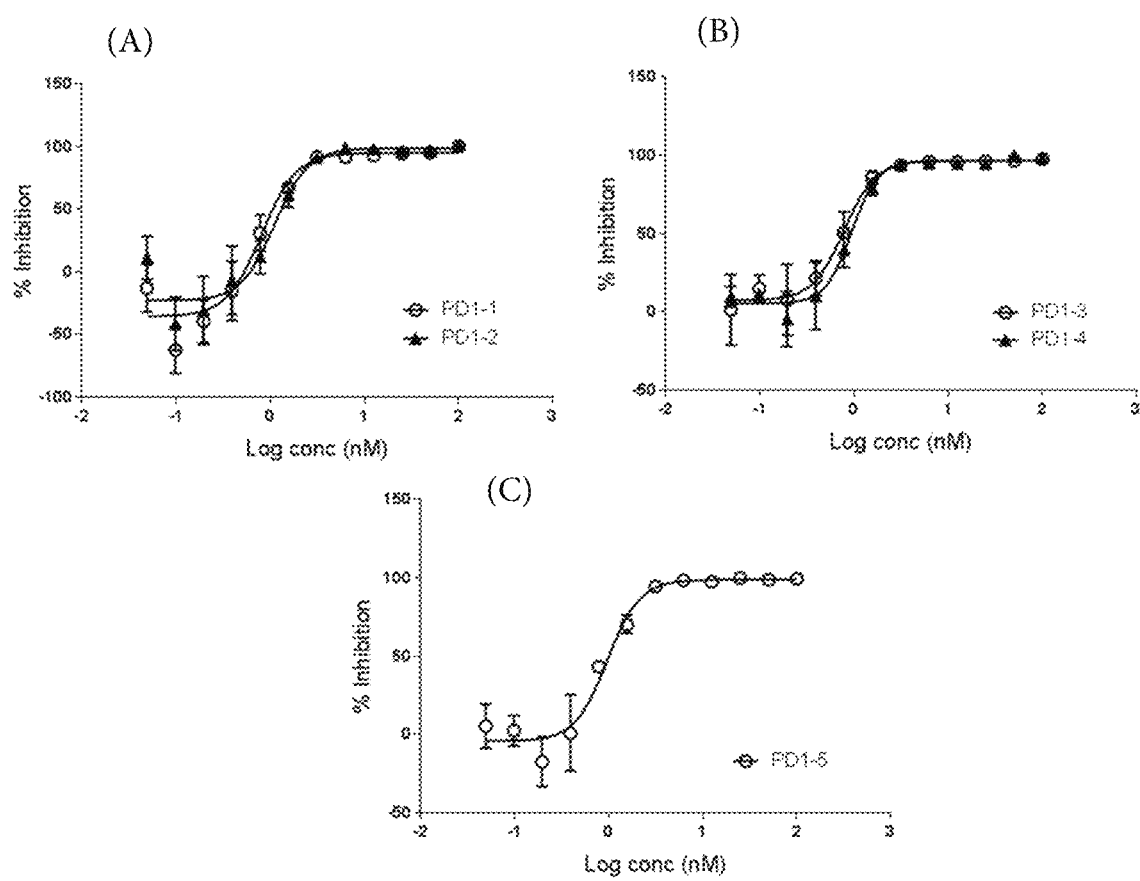
FIGS. 2a and 2b: Inhibition of human PD1-L1/L2 binding to PD1 by anti-PD1 antibody molecules.

The above and other aspects and embodiments of the invention will become clear from the further description herein.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, N.Y. (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Antibody molecules" or "antibodies" (used synonymously herein) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibody molecules can bind, by non-covalent interaction, to other molecules or structures known as antigens. This binding is specific in the sense that an antibody molecule will only bind to a specific structure with high affinity. The unique part of the antigen recognized by an antibody molecule is called an epitope, or antigenic determinant. The part of the antibody molecule binding to the epitope is sometimes called paratope and resides in the so-called variable domain, or variable region (Fv) of the antibody. The variable domain comprises three so-called complementary-determining regions (CDR's) spaced apart by framework regions (FR's).

Within the context of this invention, reference to CDR's is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

In some embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has effector function and can fix complement. In other embodiments the antibody does not recruit effector cells or fix complement. In certain embodiments, the antibody has reduced or no ability to bind an Fc receptor. For example, it may be an isotype or subtype, fragment or other mutant, which does not support binding to an Fc receptor, e.g., it has a mutagenized or deleted Fc receptor binding region.

The antibody constant region is altered in some embodiments. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388, 151 A1, U.S. Pat. Nos. 5,624,821 and 5,648,260, the contents of all of which are hereby incorporated by reference). Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

The term "variable domain" as used herein means an region of the antibody molecule which essentially consists of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The terms "variable heavy (or VH)" and "variable light (or VL)" refer to the variable domains from the heavy or light chains, respectively, of an antibody molecule.

The art has further developed antibody molecules and made them versatile tools in medicine and technology. Thus, in the context of the present invention the terms "antibody molecule" or "antibody" do not only include antibodies as they may be found in nature, comprising e.g. two light chains and two or heavy chains, but furthermore encompasses all molecules comprising at least one paratope with binding specificity to an antigen and structural similarity to a variable domain of an antibody molecule.

Thus, an antibody molecule according to the invention includes a monoclonal antibody, a human antibody, a humanized antibody, a chimeric antibody, a fragment of an antibody, in particular a Fv, Fab, Fab', or F(ab')$_2$ fragment, a single chain antibody, in particular a single chain variable fragment (scFv), a Small Modular Immunopharmaceutical (SMIP), a domain antibody, a nanobody, a diabody.

Monoclonal antibodies (mAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells.". J Immunol Methods 204 (1): 77-87.

For application in man, it is often desirable to reduce immunogenicity of antibodies originally derived from other species, like mouse. This can be done by construction of chimeric antibodies, or by a process called "humanization". In this context, a "chimeric antibody" is understood to be antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to make the overall sequence of that variable domain more closely resemble to a sequence of a human variable domain. Methods of chimerisation and humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". Nature: 332:323.).

Furthermore, technologies have been developed for creating antibodies based on sequences derived from the human genome, for example by phage display or use of transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Brüggemann M, Taussig M J. "Production of human antibody repertoires in transgenic mice". Curr Opin Biotechnol. 1997 August; 8(4):455-8.). Such antibodies are "human antibodies" in the context of the present invention.

Antibody molecules according to the present invention also include fragments of the molecules which retain antigen binding properties, like Fab, Fab', or F(ab')$_2$ fragments. Such fragments may be obtained by fragmentation of antibody molecules e.g. by proteolytic digestion, or by recombinant expression of such fragments. For example, antibody molecule digestion can be accomplished by means of routine techniques, e.g. using papain or pepsin (WO 94/29348). Papain digestion of antibodies typically produces two identical antigen binding fragments, so-called Fab fragments, each with a single antigen binding site, and a residual Fc fragment. Pepsin treatment yields an F(ab')$_2$. In Fab molecules, the variable domains are each fused to an immunoglobulin constant domain, preferably of human origin. Thus, the heavy chain variable domain may be fused to a CH$_1$ domain (a so-called Fd fragment), and the light chain variable domain may be fused to a CL domain. Fab molecules may be produced by recombinant expression of respective nucleic acids in host cells, see below.

A number of technologies have been developed for placing variable domains of antibody molecules, or molecules derived from such variable domains, in a different molecular context. Those should be also considered as "antibodies" in accordance with the present invention. In general, these antibody molecules are smaller in size compared to natural antibody molecules, and may comprise a single amino acid chain or several amino acid chains. For example, a single-chain variable fragment (scFv) is a fusion of the variable regions of the heavy and light chains of antibody molecules, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1):111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples of antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SMIP) which comprises a Fv domain linked to single-chain hinge and effector domains devoid of the constant domain CH1 (WO 02/056910).

The antibody molecule may be fused (as a fusion protein) or otherwise linked (by covalent or non-covalent bonds) to other molecular entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong the half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

The terms "epitope" and "antigenic determinant", which can be used interchangeably, refer to the part of a macromolecule, such as a polypeptide, that is recognized by antigen-binding molecules, such as the antibody molecules of the invention, and more particularly by the antigen-binding site of said molecules. Epitopes define the minimum binding site for an antibody molecule, and thus represent the target of specificity of an antibody molecule.

An antibody molecule that can "bind", "bind to", "specifically bind", or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein.

Generally, the term "specificity" refers to the number of different types of antigens or epitopes to which a particular antigen-binding molecule or antigen-binding protein (such as an immunoglobulin, an antibody, an immunoglobulin single variable domain) can bind. The specificity of an antigen-binding protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding protein: the lesser the value of the $K_D$, the stronger the binding strength between an epitope and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as an antibody of the invention) and the pertinent antigen. Avidity is related to both the affinity between an epitope and its antigen binding site on the antigen-binding molecule and the number of pertinent binding sites present on the antigen-binding molecule.

Typically, antigen-binding proteins (such as the antibody molecules of the invention) will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13 (as measured e.g. in a Kinexa assay; known in the art), and/or with an association constant ($K_A$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, an antibody of the invention will bind to the desired antigen with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays, and the different variants thereof known per se in the art.

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

The terms "compete" or "cross-compete" are used interchangeably herein to refer to the ability of an antibody molecule to interfere with binding of an antibody molecule, e.g., an anti-PD1 or LAG3 antibody molecule of the invention, to a target, e.g., human PD1 or LAG3. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-PD1 or LAG3 antibody molecule is said to compete for binding to the target with a second anti-PD1 or LAG3 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The compositions and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×00). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score-100, word-length-12, to obtain nucleotide sequences homologous to a nucleic acid encoding a protein of interest. BLAST protein searches can be performed with the XBLAST program, score-50, wordlength-3, to obtain amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO1998/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gin; (iii) polar, positively charged residues: His, Arg and Lys; (iv) large aliphatic, nonpolar residues: Met, Leu, lie, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; lie into Leu or into Val; Leu into lie or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp or into Phe; Val into lie or into Leu.

The terms "polypeptide", "peptide" and "protein" (if single chain) are used interchangeably herein.

The terms "nucleic acid," "nucleic acid sequence," "nucleotide sequence," or "polynucleotide sequence," and "polynucleotide" are used interchangeably.

The term "isolated," as used herein, refers to material that is removed from its original or native environment (e.g. the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Preferably, the nucleic acid will be part of an expression vector, wherein said nucleic acid molecule is operably linked to at least one regulatory sequence, wherein such regulatory sequence may be a promoter, enhancer, or terminator sequence, and most preferably a heterologous promoter, enhancer, or terminator sequence.

DETAILED DESCRIPTION OF THE INVENTION

Embodiments of the Invention Relating to Anti-PD1 Antibodies

As detailed above, PD1 plays an important role in regulating T-cell activity and hence immune system activity. It has been shown in a range of different cancer settings that antagonistic anti-PD1 antibody molecules can increase T-cell activity thereby activating the immune system to attack tumors and so treat cancer.

However, existing anti-PD1 antibody molecules suffer from problems associated with side-effects, and also the failure of a large proportion of patients to respond to treatment. There is therefore a need to identify alternative anti-PD1 antibody molecules which have an improved therapeutic index when compared to the prior art. Such molecules can be used in monotherapy, and also in combination with additional therapeutic agents, in particular other modulators of T-cell activity.

Against this background, the inventors sought to generate further anti-PD1 antibodies. Starting from a progenitor murine antibody to PD1 (termed 77E11), they prepared 5 humanized derivatives, which are the subject anti-PD1 antibody molecules of the present invention. The anti-PD1 antibody molecules of the present invention are termed PD1-1, PD1-2, PD1-3, PD1-4 and PD1-5.

Using an in-vitro T-cell activation assay (further described in Example 4) they examined functional characteristics of representative anti-PD1 antibodies of the present invention. As can be seen in Example 12 and FIGS. 8a and 8b, the tested antibodies were able to induce T-cell activation to a higher level when combined with anti-LAG3 antibodies in comparison to reference anti-PD1/LAG3 antibody combination, which suggests they have a more desirable therapeutic activity than the reference anti-PD1 antibodies.

As can be appreciated, this surprising ability of the anti-PD1 antibodies of the present invention to more effectively induce T-cell activation than the prior art reference anti-PD1 antibody suggests that they would be able to be used to treat cancer at a lower dosage level than the prior art reference anti-PD1 antibody, which may allow for a therapeutic application with less unwanted side effects.

Encouraged by the data, the inventors further investigated various other functional characteristics of the anti-PD1 antibody molecules of the present invention. Included in this assessment was the determination of in vivo pharmacokinetic properties. As outlined in Example 7 and shown in FIGS. 5a and 5b, as measured in Cynomolgus monkeys, the terminal elimination half-life observed for an example of the anti-PD1 antibodies of the present invention at an intravenous dose of 1 mg/kg was 1.5 to 2-fold higher than the reference prior art anti-PD1 antibodies.

In contrast to the anti-PD1 antibodies known in the art, this suggests that the anti-PD1 antibodies of the invention have a serum half-life of 11 days. This is in contrast to the known reference anti-PD1 antibody molecules which typically have a half-life of 4 to 6 days in the dose range 0.3-3 mg/kg, as can be seen from the accompanying examples. This surprising feature of the claimed antibody molecules may allow for a patient to be treated with the antibodies of the invention less frequently than those of the art, which can translate to a reduction in the amount of antibody which has to be supplied, either in the form of reduced frequency of administration or in reduced amount of antibody to be used. Given that anti-PD1 antibody molecules can induce unwanted side effects in patients, as discussed above, then the anti-PD1 antibodies of the invention may have a significant and surprising clinical advantage over the art.

Accordingly therefore a first aspect of the invention provides an anti-PD1 antibody molecules, comprising:
  (a) heavy chain CDRs comprising the amino acid sequence of SEQ ID NO:1 (hcCDR1), SEQ ID NO:2 (hcCDR2) and SEQ ID NO:3 (hcCDR3) and has light chain CDRs comprising the amino acid sequence of SEQ ID NO:4 (lcCDR1), SEQ ID NO:5 (lcCDR2) and SEQ ID NO:6 (lcCDR3); or,
  (b) heavy chain CDRs comprising the amino acid sequence of SEQ ID NO:7 (hcCDR1), SEQ ID NO:8 (hcCDR2) and SEQ ID NO:9 (hcCDR3) and has light chain CDRs comprising the amino acid sequence of SEQ ID NO:10 (lcCDR1), SEQ ID NO:11 (lcCDR2) and SEQ ID NO:12 (lcCDR3); or,
  (c) heavy chain CDRs comprising the amino acid sequence of SEQ ID NO:13 (hcCDR1), SEQ ID NO:14 (hcCDR2) and SEQ ID NO:15 (hcCDR3) and has light chain CDRs comprising the amino acid sequence of SEQ ID NO:16 (lcCDR1), SEQ ID NO:17 (lcCDR2) and SEQ ID NO:18 (lcCDR3).

As outlined above, the anti-PD1 antibody molecules of the present invention are termed PD1-1, PD1-2, PD1-3, PD1-4 and PD1-5. Provided herein is a sequence table which readily allows identification of individual amino acid sequences to specific anti-PD1 antibody molecules of the present invention. A summary is provided in Table 1 in Example 2.

In addition to the CDR sequences as set out herein, the antibody molecules of the invention include immunoglobulin framework region (FR) sequences. These sequences are preferably not immunogenic in humans, and are therefore preferably human or humanized FR sequences. Suitable human or humanized FR sequences are known in the art. Specifically preferred FR sequences can be taken from the embodiments shown herein, disclosing the complete antibody molecules and thereby CDR sequences as well as FR sequences.

Methods of preparing antibody molecules of the first aspect of the invention are well known in the art, and the skilled person would readily be able to prepare an antibody molecule having the characteristic of the first aspect of the invention. Examples of such methods are provided below.

For production of antibodies comprising two complete heavy and two complete light chains, like those of the IgG1 or IgG4 type, see Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39.

Processes for manufacturing scFv antibodies by recombinant expression of nucleic acids encoding scFv constructs in host cells (like *E. coli, Pichia pastoris*, or mammalian cell lines, e.g. CHO or NS0), yielding functional scFv molecules, are also known (Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

For the avoidance of doubt, each of the specific embodiments listed below for the first aspect of the invention can also be considered independent aspects of the invention.

A preferred embodiment of the first aspect of the invention is wherein the said antibody molecule is a humanized antibody molecule.

A further preferred embodiment of the first aspect of the invention is wherein said antibody molecule is a monoclonal antibody, Fab, F(ab')2, Fv or scFv.

The terms "humanized", "Fab", "F(ab')2", "Fv" and "scFv" are well known in the art and further discussed herein in the Definitions section of the specification.

In a preferred embodiment, the anti-PD1 antibody molecule has a heavy chain constant region selected from the group consisting of IgG1, IgG2, IgG3, IgG4, IgM, IgA and IgE constant regions. Preferably the heavy chain constant region is IgG4 with a S241P mutation.

In a preferred embodiment, the anti-PD1 antibody molecule has a light chain constant region which is kappa or lambda.

In a preferred embodiment, the anti-PD1 antibody molecule has a heavy chain variable domain comprising an amino acid sequence at least 85% identical to any of SEQ ID NOs: 19, 21, 23, 25 and 27. Preferably said antibody molecule has a heavy chain variable domain comprising an amino acid sequence of any of SEQ ID NOs: 19, 21, 23, 25 and 27.

In a preferred embodiment the anti-PD1 antibody molecules has a light chain variable domain comprising an amino acid sequence at least 85% identical to any of SEQ ID NOs: 20, 22, 24, 26 and 28. Preferably said antibody molecule has a light chain variable domain comprising the amino acid sequence of SEQ ID NOs: 20, 22, 24, 26 and 28.

Methods of calculating amino acid sequence identities are well known in the art and further discussed herein in the Definitions section of the specification.

In a preferred embodiment, the anti-PD1 antibody molecule has a heavy chain variable domain comprising the amino acid sequence of SEQ ID NO: 19.

In a preferred embodiment, the anti-PD1 antibody molecule has a heavy chain comprising the amino acid sequence of SEQ ID NO: 29.

In a preferred embodiment, the anti-PD1 antibody molecule has a heavy chain variable domain comprising the amino acid sequence of SEQ ID NO: 21.

In a preferred embodiment, the anti-PD1 antibody molecule has a heavy chain comprising the amino acid sequence of SEQ ID NO: 31.

In a preferred embodiment, the anti-PD1 antibody molecule has a heavy chain variable domain comprising the amino acid sequence of SEQ ID NO: 23.

In a preferred embodiment, the anti-PD1 antibody molecule has a heavy chain comprising the amino acid sequence of SEQ ID NO: 33.

In a preferred embodiment, the anti-PD1 antibody molecule has a heavy chain variable domain comprising the amino acid sequence of SEQ ID NO: 25.

In a preferred embodiment, the anti-PD1 antibody molecule has a heavy chain comprising the amino acid sequence of SEQ ID NO: 35.

In a preferred embodiment, the anti-PD1 antibody molecule has a heavy chain variable domain comprising the amino acid sequence of SEQ ID NO: 27.

In a preferred embodiment, the anti-PD1 antibody molecule has a heavy chain comprising the amino acid sequence of SEQ ID NO: 37.

In a preferred embodiment, the anti-PD1 antibody molecule has a light chain variable domain comprising the amino acid sequence of SEQ ID NO: 20.

In a preferred embodiment, the anti-PD1 antibody molecule has a light chain comprising the amino acid sequence of SEQ ID NO: 30.

In a preferred embodiment, the anti-PD1 antibody molecule has a light chain variable domain comprising the amino acid sequence of SEQ ID NO: 22.

In a preferred embodiment, the anti-PD1 antibody molecule has a light chain comprising the amino acid sequence of SEQ ID NO: 32.

In a preferred embodiment, the anti-PD1 antibody molecule has a light chain variable domain comprising the amino acid sequence of SEQ ID NO: 24.

In a preferred embodiment, the anti-PD1 antibody molecule has a light chain comprising the amino acid sequence of SEQ ID NO: 34.

In a preferred embodiment, the anti-PD1 antibody molecule has a light chain variable domain comprising the amino acid sequence of SEQ ID NO: 26.

In a preferred embodiment, the anti-PD1 antibody molecule has a light chain comprising the amino acid sequence of SEQ ID NO: 36.

In a preferred embodiment, the anti-PD1 antibody molecule has a light chain variable domain comprising the amino acid sequence of SEQ ID NO: 28.

In a preferred embodiment, the anti-PD1 antibody molecule has a light chain comprising the amino acid sequence of SEQ ID NO: 38.

In a preferred embodiment, the anti-PD1 antibody molecule has a heavy chain variable domain comprising the amino acid sequence of SEQ ID NO: 19 and a light chain variable domain comprising the amino acid sequence of SEQ ID NO: 20.

In a preferred embodiment, the anti-PD1 antibody molecule has a heavy chain variable domain comprising the amino acid sequence of SEQ ID NO: 21 and a light chain variable domain comprising the amino acid sequence of SEQ ID NO: 22.

In a preferred embodiment, the anti-PD1 antibody molecule has a heavy chain variable domain comprising the amino acid sequence of SEQ ID NO: 23 and a light chain variable domain comprising the amino acid sequence of SEQ ID NO: 24.

In a preferred embodiment, the anti-PD1 antibody molecule has a heavy chain variable domain comprising the amino acid sequence of SEQ ID NO: 25 and a light chain variable domain comprising the amino acid sequence of SEQ ID NO: 26.

In a preferred embodiment, the anti-PD1 antibody molecule has a heavy chain variable domain comprising the amino acid sequence of SEQ ID NO: 27 and a light chain variable domain comprising the amino acid sequence of SEQ ID NO: 28.

In a preferred embodiment, the anti-PD1 antibody molecule has a heavy chain comprising the amino acid sequence of SEQ ID NO: 29 and a light chain comprising the amino acid sequence of SEQ ID NO: 30.

In a preferred embodiment, the anti-PD1 antibody molecule has a heavy chain comprising the amino acid sequence of SEQ ID NO: 31 and a light chain comprising the amino acid sequence of SEQ ID NO: 32.

In a preferred embodiment, the anti-PD1 antibody molecule has a heavy chain comprising the amino acid sequence of SEQ ID NO: 33 and a light chain comprising the amino acid sequence of SEQ ID NO: 34.

In a preferred embodiment, the anti-PD1 antibody molecule has a heavy chain comprising the amino acid sequence of SEQ ID NO: 35 and a light chain comprising the amino acid sequence of SEQ ID NO: 36.

In a preferred embodiment, the anti-PD1 antibody molecule has a heavy chain comprising the amino acid sequence of SEQ ID NO: 37 and a light chain comprising the amino acid sequence of SEQ ID NO: 38.

For all of the above embodiments it shall be understood that, by using the term "comprising", it is intended to also include an embodiment in which the respective domain or molecule "consists" of the amino acid sequence as indicated.

In a preferred embodiment, the anti-PD1 antibody molecule is capable of binding to human PD1 with a dissociation constant (KD) of less than 10 nM.

In some embodiments, the anti-PD1 antibody molecule is capable of binding to human PD1 and cynomolgus monkey PD1 with high affinity. In some embodiments, high affinity refers to a $K_D$ of less than 10 nM e.g. 9, 8, 7, 6 or lower, as measured by SPR. A protocol for determining $K_D$ using SPR is provided in the accompanying examples.

In a preferred embodiment, the anti-PD1 antibody molecule does not bind to mouse PD1.

In a preferred embodiment, the anti-PD1 antibody molecule is capable of reducing the binding of human PD-L1/L2 with human PD1. An assay to determine binding of human PD-L1/L2 with human PD1 is provided in the accompanying examples.

In some embodiments, the anti-PD1 antibody molecule is capable of inhibiting the binding of ligands PD-L1 and PD-L2 to PD1 with an $IC_{90}$ of less than 10 nM, 9, 8, 7, 6, 5 or 4 nM or lower. A protocol for determining $IC_{90}$ is provided in the accompanying examples.

In a preferred embodiment, the anti-PD1 antibody molecule is capable of enhancing an antigen-specific T cell response. An assay to determine an antigen-specific T cell response is provided in Example 4.

A further aspect of the present invention provides isolated nucleic acid molecules encoding the heavy chain variable domain and/or the light chain variable domain of an anti-PD1 antibody molecule of any of the first aspect of the invention.

Preferably the nucleic acid molecule comprises the nucleotide sequence of SEQ ID NOs: 71, 73, 75, 77 or 79 respectively encoding the heavy chain variable domain of SEQ ID NOs 19, 21, 23, 25 or 27. Preferably the nucleic acid molecule comprises the nucleotide sequence of SEQ ID NOs: 72, 74, 76, 78 or 80 respectively encoding the light chain variable domain of SEQ ID NOs 20, 22, 24, 26 or 28.

A further aspect of the invention provides an expression vector containing a DNA molecule comprising the nucleotide sequence encoding the heavy chain variable domain and/or the light chain variable domain of an anti-PD1 antibody molecule of the invention. Preferably the expression vector contains a DNA molecule comprising the nucleotide sequence of SEQ ID NO: 71 and/or SEQ ID NO: 72, or comprising the nucleotide sequence of SEQ ID NO: 73 and/or SEQ ID NO: 74, or comprising the nucleotide sequence of SEQ ID NO: 75 and/or SEQ ID NO: 76, or comprising the nucleotide sequence of SEQ ID NO: 77 and/or SEQ ID NO: 78 or comprising the nucleotide sequence of SEQ ID NO: 79 and/or SEQ ID NO: 80.

Preferably the expression vector comprises, in addition, a nucleic acid molecule, preferably a DNA molecule, encoding the constant domains of a heavy chain and/or the constant domain of a light chain, respectively, linked to the nucleic acid molecule, preferably the DNA molecule, encoding the heavy chain variable domain and/or the light chain variable domain, respectively.

In a specifically preferred embodiment, two expression vectors may be used, one of them for expression of the heavy chain, the other one for expression of the light chain, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promoter, enhancer, or terminator sequence.

The nucleic acids of the invention may be prepared or obtained in a manner known per se (e.g. by automated DNA synthesis and/or recombinant DNA technology), based on the information on the amino acid sequences for the antibodies of the invention given herein.

In another aspect, the invention relates to a host cell having an expression vector encoding a heavy chain of an anti-PD1 antibody molecule of the invention and an expression vector encoding a light chain of an anti-PD1 antibody molecule of the invention.

According to a particularly preferred embodiment, said host cells are eukaryotic cells such as mammalian cells. In another embodiment, such host cells are bacterial cells. Other useful cells are yeast cells or other fungal cells.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

Embodiments of the Invention Relating to Anti-LAG3 Antibody Molecules and Combination with Anti-PD1 Antibodies As detailed above, PD1 plays an important role in regulating T-cell activity and hence immune system activity. It has been shown in a range of different cancer settings that antagonistic anti-PD1 antibodies molecules can increase T-cell activity thereby activating the immune system to attack tumors and so treat cancer.

It has also been shown that combinations of antagonistic anti-PD1 antibodies with antibody molecules which target further immune cell checkpoint inhibitors can potentiate the anti-cancer properties of antagonistic anti-PD1 antibodies. One such checkpoint inhibitor is called LAG3.

As with PD1, LAG3 appears to play a role in mediating T-cell activity. Moreover, it is known in the art that duel blockade of the PD1 pathway and LAG3 is more effective for anti-tumor immunity than blocking either molecule alone.

Against this background, the inventors sought to generate further anti-LAG3 antibody molecules which could be used either alone or in combination with the anti-PD1 antibody molecules of the present invention. Starting from a progenitor murine antibody to LAG3 (termed 496G6), they prepared five humanized derivates, which are the subject anti-LAG3 antibody molecules of the present invention. The anti-LAG3 antibody molecules of the present invention are termed LAG3-1, LAG3-2, LAG3-3, LAG3-4 and LAG3-5.

Using an in-vitro T-cell activation assay (further outlined in Example 12) they examined functional characteristics of representative anti-LAG3 antibody molecules of the present invention. As can be seen in Example 12 and FIG. 8, the combination of anti-LAG3 antibody molecule of the present invention with anti-PD1 antibody molecule of the present invention is surprisingly superior to reference anti-PD1/LAG3 antibody combinations known in the art.

As can be appreciated, this superiority of the combination of the anti-LAG3 antibody molecules of the present invention with anti-PD1 antibody molecules of the present invention suggests that they would be able to be used to treat cancer at a lower dosage level than the prior art antibody therapeutics, which may allow for a therapeutic application with less unwanted side effects.

Given that anti-PD1 and anti-LAG3 antibody molecules may induce unwanted side effects in patients, as discussed above, then the anti-PD1 antibodies and anti-LAG3 antibodies of the invention could have a significant and surprising clinical advantage over the art by using lower dosage and/or less frequent administration regimes.

Encouraged by the data, the inventors further investigated various other functional characteristics of the anti-LAG3 antibody molecules of the invention. Included in this assessment was the determination of the epitope bound by examples of the anti-LAG3 antibody molecules of the present invention. As can be seen in Example 11 the inventors determined that the anti-LAG3 antibody molecules of the invention can bind to two distinct regions of human LAG-3, LLRRAGVT (SEQ ID NO: 111) and/or YRAAVHLRDRA (SEQ ID NO: 112).

To the best of the knowledge of the inventors, no known prior art anti-LAG3 antibody has the same epitope binding profile as the anti-LAG3 antibody molecules of the invention. While not wishing to be bound to any particular theory, the inventors speculate that the surprising improved effectiveness of the combination of the anti-LAG3 antibody molecules of the present invention with anti-PD1 antibodies of the present invention when compared to the prior art molecules may be attributable to the epitope binding profile of the anti-LAG3 antibody molecules of the invention.

Therefore a further aspect of the invention provides an isolated anti-LAG3 antibody molecule, wherein said anti-LAG3 antibody molecule binds an epitope of human LAG3 comprising the amino acid sequence LLRRAGVT (SEQ ID NO: 111) and/or YRAAVHLRDRA (SEQ ID NO: 112). Such molecules are termed herein "anti-LAG3 antibody molecules of the present invention"

Methods of preparing anti-LAG3 antibody molecules having the epitope binding characteristics of the invention are well known in the art.

Methods of generating antibodies and antibody fragments are well known in the art. For example, antibodies may be generated via any one of several methods which employ induction of in vivo production of antibody molecules, screening of immunoglobulin libraries (Orlandi et al, 1989. Proc. Natl. Acad. Sci. U.S.A. 86:3833-3837; Winter et al 1991, Nature 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al 1975. Nature 256:4950497; Kozbor et al 1985. J. Immunol. Methods 81:31-42; Cote et al 1983. Proc. Natl. Acad. Sci. USA 80:2026-2030; Cole et al 1984. Mol. Cell. Biol. 62:109-120).

Using these methods it would be routine for the person skilled in the art to prepare antibodies having a binding site with the necessary specificity for LAG3. Candidate antibody molecules can then be screened using epitope mapping to determine whether they bind to the same epitope sequences as required by the anti-LAG3 antibodies of the present invention. Such epitope mapping methods are well known and routine in the art and can be readily adopted by the skilled person. Furthermore, an example of such methodology is provided in Example 11 in the present specification.

For the avoidance of doubt, each of the specific embodiments listed below for the anti-LAG3 antibodies of the present invention can also be considered independent aspects of the invention.

A preferred embodiment of the first aspect of the invention is wherein the said antibody molecule is a humanized antibody molecule.

A further preferred embodiment is wherein said antibody molecule is a monoclonal antibody, Fab, F(ab')2, Fv or scFv.

The terms "humanized", "Fab", "F(ab')2", "Fv" and "scFv" are well known in the art and further discussed herein in the Definitions section of the specification.

In a preferred embodiment, the anti-LAG3 antibody molecule has a heavy chain constant region selected from the group consisting of IgG1, IgG2, IgG3, IgG4, IgM, IgA and IgE constant regions. Preferably the heavy chain constant region is IgG4 with a S241P mutation.

In a preferred embodiment, the anti-LAG3 antibody molecule has a light chain constant region which is kappa or lambda.

A further preferred embodiment is wherein said anti-LAG3 antibody molecule comprises:

(a) heavy chain CDRs comprising the amino acid sequence of SEQ ID NO:39 (hcCDR1), SEQ ID NO:40 (hcCDR2) and SEQ ID NO:41 (hcCDR3) and has light chain CDRs comprising the amino acid sequence of SEQ ID NO:42 (lcCDR1), SEQ ID NO:43 (lcCDR2) and SEQ ID NO:44 (lcCDR3); or, (b) heavy chain CDRs comprising the amino acid sequence of SEQ ID NO:45 (hcCDR1), SEQ ID NO:46 (hcCDR2) and SEQ ID NO:47 (hcCDR3) and has light chain CDRs comprising the amino acid sequence of SEQ ID NO:48 (lcCDR1), SEQ ID NO:49 (lcCDR2) and SEQ ID NO:50 (lcCDR3).

As outlined above, the anti-LAG3 antibody molecules of the present invention are termed LAG3-1, LAG3-2, LAG3-3, LAG3-4 and LAG3-5. Provided herein is a sequence table which readily allows identification of individual amino acid sequences to specific anti-LAG3 antibody molecules of the present invention. A summary is provided in Table 6 in Example 9.

Methods of preparing anti-LAG3 antibody molecules of the present invention are well known in the art, and the skilled person would readily be able to prepare an antibody molecule. Examples of such methods are provided above in relation to the first aspect of the invention.

In a preferred embodiment, the anti-LAG3 antibody molecule has a heavy chain variable domain comprising an amino acid sequence at least 85% identical to any of SEQ ID NOs: 51, 53, 55, 57 and 59. Preferably said antibody molecule has a heavy chain variable domain comprising an amino acid sequence of any of SEQ ID NOs: 51, 53, 55, 57 and 59.

In a preferred embodiment the anti-LAG3 antibody molecule has a light chain variable domain comprising an amino acid sequence at least 85% identical to any of SEQ ID NOs: 52, 54, 56, 58 and 60. Preferably said antibody molecule has a light chain variable domain comprising the amino acid sequence of SEQ ID NOs: 52, 54, 56, 58 and 60.

Methods of calculating amino acid sequence identities are well known in the art and further discussed herein in the Definitions section of the specification.

In a preferred embodiment, the anti-LAG3 antibody molecule has a heavy chain variable domain comprising the amino acid sequence of SEQ ID NO: 51.

In a preferred embodiment, the anti-LAG3 antibody molecule has a heavy chain comprising the amino acid sequence of SEQ ID NO: 61.

In a preferred embodiment, the anti-LAG3 antibody molecule has a heavy chain variable domain comprising the amino acid sequence of SEQ ID NO: 53.

In a preferred embodiment, the anti-LAG3 antibody molecule has a heavy chain comprising the amino acid sequence of SEQ ID NO: 63.

In a preferred embodiment, the anti-LAG3 antibody molecule has a heavy chain variable domain comprising the amino acid sequence of SEQ ID NO: 55.

In a preferred embodiment, the anti-LAG3 antibody molecule has a heavy chain comprising the amino acid sequence of SEQ ID NO: 65.

In a preferred embodiment, the anti-LAG3 antibody molecule has a heavy chain variable domain comprising the amino acid sequence of SEQ ID NO: 57.

In a preferred embodiment, the anti-LAG3 antibody molecule has a heavy chain comprising the amino acid sequence of SEQ ID NO: 67.

In a preferred embodiment, the anti-LAG3 antibody molecule has a heavy chain variable domain comprising the amino acid sequence of SEQ ID NO: 59.

In a preferred embodiment, the anti-LAG3 antibody molecule has a heavy chain comprising the amino acid sequence of SEQ ID NO: 69.

In a preferred embodiment, the anti-LAG3 antibody molecule has a light chain variable domain comprising the amino acid sequence of SEQ ID NO: 52.

In a preferred embodiment, the anti-LAG3 antibody molecule has a light chain comprising the amino acid sequence of SEQ ID NO: 62.

In a preferred embodiment, the anti-LAG3 antibody has a light chain variable domain comprising the amino acid sequence of SEQ ID NO: 54.

In a preferred embodiment, the anti-LAG3 antibody molecule has a light chain comprising the amino acid sequence of SEQ ID NO: 64.

In a preferred embodiment, the anti-LAG3 antibody molecule has a light chain variable domain comprising the amino acid sequence of SEQ ID NO: 56.

In a preferred embodiment, the anti-LAG3 antibody molecule has a light chain comprising the amino acid sequence of SEQ ID NO: 66.

In a preferred embodiment, the anti-LAG3 antibody molecule has a light chain variable domain comprising the amino acid sequence of SEQ ID NO: 58.

In a preferred embodiment, the anti-LAG3 antibody molecule has a light chain comprising the amino acid sequence of SEQ ID NO: 68.

In a preferred embodiment, the anti-LAG3 antibody molecule has a light chain variable domain comprising the amino acid sequence of SEQ ID NO: 60.

In a preferred embodiment, the anti-LAG3 antibody molecule has a light chain comprising the amino acid sequence of SEQ ID NO: 70.

In a preferred embodiment, the anti-LAG3 antibody molecule has a heavy chain variable domain comprising the amino acid sequence of SEQ ID NO: 51 and a light chain variable domain comprising the amino acid sequence of SEQ ID NO: 52.

In a preferred embodiment, the anti-LAG3 antibody molecule has a heavy chain variable domain comprising the amino acid sequence of SEQ ID NO: 53 and a light chain variable domain comprising the amino acid sequence of SEQ ID NO: 54.

In a preferred embodiment, the anti-LAG3 antibody molecule has a heavy chain variable domain comprising the amino acid sequence of SEQ ID NO: 55 and a light chain variable domain comprising the amino acid sequence of SEQ ID NO: 56.

In a preferred embodiment, the anti-LAG3 antibody molecule has a heavy chain variable domain comprising the amino acid sequence of SEQ ID NO: 57 and a light chain variable domain comprising the amino acid sequence of SEQ ID NO: 58.

In a preferred embodiment, the anti-LAG3 antibody molecule has a heavy chain variable domain comprising the amino acid sequence of SEQ ID NO: 59 and a light chain variable domain comprising the amino acid sequence of SEQ ID NO: 60.

In a preferred embodiment, the anti-LAG3 antibody molecule has a heavy chain comprising the amino acid sequence of SEQ ID NO: 61 and a light chain comprising the amino acid sequence of SEQ ID NO: 62.

In a preferred embodiment, the anti-LAG3 antibody molecule has a heavy chain comprising the amino acid sequence of SEQ ID NO: 63 and a light chain comprising the amino acid sequence of SEQ ID NO: 64.

In a preferred embodiment, the anti-LAG3 antibody molecule has a heavy chain comprising the amino acid sequence of SEQ ID NO: 65 and a light chain comprising the amino acid sequence of SEQ ID NO: 66.

In a preferred embodiment, the anti-LAG3 antibody molecule has a heavy chain comprising the amino acid sequence of SEQ ID NO: 67 and a light chain comprising the amino acid sequence of SEQ ID NO: 68.

In a preferred embodiment, the anti-LAG3 antibody molecule has a heavy chain comprising the amino acid sequence of SEQ ID NO: 69 and a light chain comprising the amino acid sequence of SEQ ID NO: 70.

For all of the above embodiments it shall be understood that, by using the term "comprising", it is intended to also include an embodiment in which the respective molecule or domain "consists" of the amino acid sequence as indicated.

In a preferred embodiment, the anti-LAG3 antibody molecule is capable of binding to human LAG3 with a dissociation constant (KD) of less than 1 nM.

In some embodiments, the anti-LAG3 antibody molecule is capable of binding to human LAG3 and cynomolgus monkey LAG3 with high affinity. In some embodiments, high affinity refers to a $K_D$ of less than 0.5 nM, e.g. 0.4, 0.3, 0.2, 0.1, 0.09, 0.08, 0.07 or lower, as measured by SPR. A protocol for determining $K_D$ using SPR is provided in the accompanying examples.

In a further embodiment, the anti-LAG3 antibody molecule does not bind to mouse LAG3.

In a further embodiment, the anti-LAG3 antibody molecule is capable of one or more of the following properties: (i) binding to cynomolgus monkey LAG3; (ii) lack of binding to murine LAG3; (iii) inhibits binding of LAG3 to MHC II; and (iv) stimulates an immune response.

A further aspect of the invention provides an anti-LAG3 antibody molecule of the invention for use in medicine.

A further aspect of the present invention provides isolated nucleic acid molecules encoding the heavy chain variable domain and/or the light chain variable domain of an anti-LAG3 antibody molecule of the invention. Preferably the nucleic acid molecule comprises the nucleotide sequence of SEQ ID NOs: 91, 93, 95, 97 or 99 respectively encoding the heavy chain variable domain of SEQ ID NOs: 51, 53, 55, 57 or 59. Preferably the nucleic acid molecule comprises the nucleotide sequence of SEQ ID NOs: 92, 94, 96, 98 or 100 respectively encoding the light chain variable domain of SEQ ID NOs: 52, 54, 56, 58 or 60.

A further aspect of the invention provides an expression vector containing a DNA molecule comprising the nucleotide sequence encoding the heavy chain and/or the light chain of an anti-LAG3 antibody molecule of the invention. Preferably the expression vector contains a DNA molecule comprising the nucleotide sequence of SEQ ID NO: 101 and/or SEQ ID NO: 102, or comprising the nucleotide sequence of SEQ ID NO: 103 and/or SEQ ID NO: 104, or comprising the nucleotide sequence of SEQ ID NO: 105 and/or SEQ ID NO: 106, or comprising the nucleotide sequence of SEQ ID NO: 107 and/or SEQ ID NO: 108 or comprising the nucleotide sequence of SEQ ID NO: 109 and/or SEQ ID NO: 110.

In a specifically preferred embodiment, two expression vectors may be used, one of them for expression of the heavy chain, the other one for expression of the light chain, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promoter, enhancer, or terminator sequence.

The nucleic acids of the invention may be prepared or obtained in a manner known per se (e.g. by automated DNA synthesis and/or recombinant DNA technology), based on the information on the amino acid sequences for the antibodies of the invention given herein, as described further above in relation to anti-PD1 antibodies of the present invention.

In another aspect, the invention relates to a host cell having an expression vector encoding a heavy chain of an anti-LAG3 antibody molecule of the invention and an expression vector encoding a light chain of an anti-LAG3 antibody molecule of the invention.

According to a particularly preferred embodiment, said host cells are eukaryotic cells such as mammalian cells, e.g. those already set out above in connection with the anti-PD1 antibodies embodiment. In another embodiment, such host cells are bacterial cells. Other useful cells are yeast cells or other fungal cells.

Embodiments of the Invention Relating to Pharmaceutical Compositions Including Anti-PD1 and Anti-LAG3 Antibodies, Kit of Parts, Methods and Uses.

A further aspect of the invention provides a kit of parts comprising an anti-PD1 antibody molecule of the invention and an anti-LAG3 antibody molecule. Preferably the anti-LAG3 antibody molecule is an anti-LAG3 antibody molecule of the invention.

A further aspect of the invention provides a kit of parts comprising an anti-LAG3 antibody molecule of the invention and an anti-PD1 antibody molecule. Preferably the anti-PD1 antibody molecule is an anti-PD1 antibody molecule of the invention. Alternatively, another anti-PD1 antibody, such as pembrolizumab or nivolumab, can be used in such kit of parts.

A further aspect of the invention provides a pharmaceutical composition comprising an anti-PD1 antibody molecule of the invention. An embodiment of the invention is wherein the pharmaceutical composition further comprises an anti-LAG3 antibody molecule. Preferably the anti-LAG3 antibody molecule is an anti-LAG3 antibody molecule of the invention.

A further aspect of the invention provides a pharmaceutical composition comprising an anti-LAG3 antibody molecule of the invention. An embodiment of the invention is wherein the pharmaceutical composition further comprises an anti-PD1 antibody molecule. Preferably the anti-PD1 antibody molecule is an anti-PD1 antibody molecule of the invention. Alternatively, another anti-PD1 antibody, such as pembrolizumab or nivolumab, can be used in such pharmaceutical composition.

It will be clear to the skilled person that based on the above, there are also disclosed herewith pharmaceutical compositions for the treatment of a disease (as specified in more detail below) using the antibody molecules of the invention set out above, as well as methods of treating a disease (as specified in more detail below) making use of such pharmaceutical compositions or antibody molecules of the invention.

For the avoidance of doubt, the kit of parts and the pharmaceutical composition of the invention may comprise any of the specific anti-PD1 antibody molecules of the invention and/or anti-LAG3 antibody molecule of the invention as described above.

When the anti-PD1 antibody molecule of the invention and the anti-LAG3 antibody molecule of the invention are to be administered simultaneously via the same route of administration, they may be administered as different pharmaceutical formulations or compositions or as part of a combined pharmaceutical formulation or composition. Also, when the anti-PD1 antibody molecule of the invention and the anti-LAG3 antibody molecule of the invention are to be used as part of a combined treatment regimen, each of the antibodies may be administered in the same amount and according to the same regimen as used when one of the antibodies is used on its own, and such combined use may or may not lead to a synergistic effect. However, when the combined use of the antibodies leads to a synergistic effect, it may also be possible to reduce the amount of one or both of the antibodies, while still achieving the desired therapeutic action. This may for example be useful for avoiding, limiting or reducing any unwanted side-effects that are associated with the use of one or both of the antibodies when they are used in their usual amounts, while still obtaining the desired pharmacological or therapeutic effect.

Pharmaceutical Compositions, Methods of Administration, Dosages

The invention further relates to pharmaceutical compositions for the treatment of a diseases (as specified in more detail below), wherein such compositions comprise at least one antibody molecule of the invention. The invention further encompasses methods of treating a disease (as specified in more detail below) using at least one antibody molecule of the invention or pharmaceutical composition as set out before, and further encompasses the preparation of a medicament for the treatment of such disease by using such antibody molecule(s) of the invention or pharmaceutical composition.

The antibody molecules of the invention and/or the compositions comprising the same can be administered to a patient in need thereof in any suitable manner, depending on the specific pharmaceutical formulation or composition to be used. Thus, the antibody molecules of the invention and/or the compositions comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, or any other suitable manner in an effective amount or dose.

The antibody molecules of the invention and/or the compositions comprising the same are administered according to a regimen of treatment that is suitable for treating and/or alleviating the disease, disorder or condition to be treated or alleviated. The clinician will generally be able to determine a suitable treatment regimen, depending on factors such as the disease, disorder or condition to be treated or alleviated, the severity of the disease, the severity of the symptoms thereof, the specific antibody molecules of the invention to be used, the specific route of administration and pharmaceutical formulation or composition to be used, the age, gender, weight, diet, general condition of the patient, and similar factors well known to the clinician. Generally, the treatment regimen will comprise the administration of one or more antibody molecules of the invention, or of one or more compositions comprising the same, in therapeutically effective amounts or doses.

Generally, for the treatment and/or alleviation of the diseases, disorders and conditions mentioned herein and depending on the specific disease, disorder or condition to be treated, the potency of the specific antibody molecule of the invention to be used, the specific route of administration and the specific pharmaceutical formulation or composition used, the antibody molecules of the invention will generally be administered in an amount between 0.005 and 20.0 mg per kilogram of body weight and dose, preferably between 0.05 and 10.0 mg/kg/dose, and more preferably between 0.5 and 10 mg/kg/dose, either continuously (e.g. by infusion) or more preferably as single doses (such as e.g. twice a week, weekly, or monthly doses; cf. below), but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

Depending on the specific antibody molecule of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the antibody molecules of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

Formulations

For pharmaceutical use, the antibody molecules of the invention may be formulated as a pharmaceutical preparation comprising (i) at least one antibody of the invention (i.e. an anti-PD1 antibody of the invention or an anti-LAG3 antibody of the invention or both types of antibodies of the invention together) and (ii) at least one pharmaceutically acceptable carrier, diluent, excipient, adjuvant, and/or stabilizer, and (iii) optionally one or more further pharmacologically active polypeptides and/or compounds. By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, 18$^{th}$ Ed., Mack Publishing Company, USA (1990). For example, the antibodies of the invention may be formulated and administered in any manner known per se for conventional antibodies and antibody fragments and other pharmaceutically active proteins. Thus, according to a further embodiment, the invention relates to a pharmaceutical composition or preparation that contains at least one antibodys of the invention and at least one pharmaceutically acceptable carrier, diluent, excipient, adjuvant and/or stabilizer, and optionally one or more further pharmacologically active substances.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the antibody molecules of the invention may also contain a preservative to prevent the growth of microorganisms, such as antibacterial and antifungal agents, for example, p-hydroxybenzoates, parabens, chlorobutanol, phenol, sorbic acid, thiomersal, (alkali metal salts of) ethylenediamine tetraacetic acid, and the like. In many cases, it will be preferable to include isotonic agents, for example, sugars, buffers or sodium chloride. Optionally, emulsifiers and/or dispersants may be used. The proper fluidity can be maintained, for example, by the formation of liposomes, by the maintenance of the required particle size in the case of dispersions or by the use of surfactants. Other agents delaying absorption, for example, aluminum monostearate and gelatin, may also be added. The solutions may be filled into injection vials, ampoules, infusion bottles, and the like.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the antibodies of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s.c. administration) and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.5 to 7.0,
succinate buffers, pH 3.2 to 6.6, and
citrate buffers, pH 2.1 to 6.2, and, optionally, salts (e.g. NaCl) and/or sugars (such as e.g. sucrose and trehalose) and/or other polyalcohols (such as e.g. mannitol and glycerol) for providing isotonicity of the solution.

Preferred buffered protein solutions are solutions including about 0.05 mg/ml of the antibody of the invention dissolved in 25 mM phosphate buffer, pH 6.5, adjusted to isotonicity by adding 220 mM trehalose. In addition, other agents such as a detergent, e.g. 0.02% Tween-20 or Tween-80, may be included in such solutions. Formulations for subcutaneous application may include significantly higher concentrations of the antibody of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure.

According to a further aspect of the invention, an antibody molecule of the invention may be used in combination with a device useful for the administration of the antibody, such as a syringe, injector pen, micropump, or other device.

Therapeutic Uses

A further aspect of the invention provides a method of treating cancer comprising administering to a patient in need thereof a therapeutically effective amount of the anti-PD1 antibody molecule of the invention. In a preferred embodiment the method further comprises administering to such patient an anti-LAG3 antibody molecule. Preferably the anti-LAG3 antibody molecule is an anti-LAG3 antibody molecule of the invention.

A further aspect of the invention provides an anti-PD1 antibody molecule of the invention for use in a method of treating cancer. In a preferred embodiment the aspect further comprises the additional use of an anti-LAG3 antibody molecule. Preferably the anti-LAG3 antibody molecule is an anti-LAG3 antibody molecule of the invention.

A further aspect of the invention is the use of the anti-PD1 antibody molecule of the invention for preparing a pharmaceutical composition for treating cancer. In a preferred embodiment the aspect further comprises the additional use of an anti-LAG3 antibody molecule. Preferably the anti-LAG3 antibody molecule is an anti-LAG3 antibody molecule of the invention.

In an embodiment the anti-PD1 antibody molecule is to be administered simultaneously, concurrently, sequentially, successively, alternatively or separately, with the anti-LAG3 antibody molecule.

A further aspect of the invention provides a method of treating cancer comprising administering to a patient in need thereof a therapeutically effective amount of the anti-LAG3 antibody molecule of the invention. In a preferred embodiment the method further comprises administering to such patient an anti-PD1 antibody molecule. Preferably the anti-LAG3 antibody molecule is an anti-PD1 antibody molecule of the invention.

A further aspect of the invention provides an anti-LAG3 antibody molecule of the invention for use in a method of treating cancer. In a preferred embodiment the aspect further comprises the additional use of an anti-PD1 antibody molecule. Preferably the anti-PD1 antibody molecule is an anti-PD1 antibody molecule of the invention.

A further aspect of the invention is the use of the anti-LAG3 antibody molecule of the invention for preparing a pharmaceutical composition for treating cancer. In a preferred embodiment the aspect further comprises the additional use of an anti-PD1 antibody molecule. Preferably the anti-PD1 antibody molecule is an anti-PD1 antibody molecule of the invention.

In an embodiment the anti-LAG3 antibody molecule is to be administered simultaneously, concurrently, sequentially, successively, alternatively or separately, with the anti-PD1 antibody molecule.

For the avoidance of doubt, the medical uses aspects of the invention may comprise any of the specific anti-PD1 antibody molecule of the invention and/or anti-LAG3 antibody molecule of the invention as described above.

Due to their biological properties, the antibodies of the invention are suitable for treating diseases characterised by excessive or abnormal cell proliferation, such as cancer.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas) of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions described herein.

Exemplary cancers whose growth can be inhibited using the antibody molecules disclosed herein include cancers typically responsive to immunotherapy.

For example, the following cancers, tumors, and other proliferative diseases may be treated with antibodies according to the invention, without being restricted thereto:

Cancers of the head and neck; Cancers of the lung, such as e.g. non-small cell lung cancer (NSCLC) and small cell lung cancer (SCLC); Neoplasms of the mediastinum, such as e.g. neurogenic tumors and mesenchymal tumors; Cancers of the gastrointestinal (GI) tract, such as e.g. cancers of the esophagus, stomach (gastric cancer), pancreas, liver and biliary tree (including e.g. hepatocellular carcinoma (HCC)), and the small and large intestine (including e.g. colorectal cancer); Cancers of the prostate; Cancers of the testis; Gynecologic cancers, such as e.g. cancers of the ovary; Cancers of the breast, such as e.g. mammary carcinoma, hormone receptor positive breast cancer, Her2 positive breast cancer, and triple negative breast cancer; Cancers of the endocrine system; Sarcomas of the soft tissues, such as e.g. fibrosarcoma, rhabdomyosarcoma, angiosarcoma, Kaposi's sarcoma; Sarcomas of the bone, such as e.g. myeloma, osteosarcoma, Ewing's tumor, fibrosarcoma, osteochondroma, osteoblastoma, and chondroblastoma; Mesotheliomas; Cancers of the skin, such as e.g. basal cell carcinoma, squamous cell carcinoma, Merkel's cell carcinoma, and melanoma; Neoplasms of the central nervous system and brain, such as e.g. astrocytoma, glioblastoma, gliomas neuroblastomas, and retinoblastomas; Lymphomas and leukemias such as e.g. B-cell non-Hodgkin lymphomas (NHL), T-cell non-Hodgkin lymphomas, chronic B-cell lymphocytic leukemia (B-CLL), chronic T-cell lymphocytic leukemia (T-CLL), Hodgkin's disease (HD), large granular lymphocyte leukemia (LGL), chronic myelogenous leukemia (CML), acute myelogenous/myeloid leukemia (AML), acute lymphatic/lymphoblastic leukemia (ALL), multiple myeloma (MM), plasmacytoma, and myelodysplastic syndromes (MDS); and cancers of unknown primary site.

In a preferred embodiment of the invention the cancer is lung cancer, preferably non-small cell lung cancer (NSCLC).

All cancers, tumors, neoplasms, etc., mentioned above which are characterized by their specific location/origin in the body are meant to include both the primary tumors and the metastatic tumors derived therefrom.

It is possible that a patient is more likely to respond to treatment with an antibody molecule of the invention (as described herein) if that patient has a cancer which is characterized by having a high expression of PD-L1, and/or where the cancer is infiltrated by anti-tumor immune cells, e.g. tumor-infiltrating lymphocytes. Hence an embodiment of the invention is wherein the patient to be treated has a cancer which is characterized by having a high expression of PD-L1 and/or where the cancer is infiltrated by anti-tumor immune cells.

Furthermore, it is possible that a patient is more likely to respond to treatment with an antibody molecule of the invention (as described herein) if that patient has a cancer which is characterized by having a high-mutational burden. Examples of how high mutational burden can be assessed include determining whether the cancer is characterized by having microsatellite instabilities, or poor DNA mismatch repair efficiencies. It is thought that such cancers are more immunogenic and hence are more likely to respond to treatment with immunomodulatory therapeutic regimes, such as an antibody molecule of the invention. Hence an embodiment of the invention is wherein the patient to be treated has a cancer which is characterized by having a high-mutational burden.

The antibody molecules of the invention may be used in therapeutic regimens in the context of first line, second line, or any further line treatments.

The antibody molecules of the invention may be used for the prevention, short-term or long-term treatment of the above-mentioned diseases, optionally also in combination with radiotherapy and/or surgery.

Of course, the above also includes the use of the antibody molecules of the invention in various methods of treating the above diseases by administering a therapeutically effective dose to a patient in need thereof, as well as the use of these antibody molecules for the manufacture of medicaments for the treatment of such diseases, as well as pharmaceutical compositions including such antibody molecules of the inventions, as well as the preparation and/or manufacture of medicaments including such antibodies of the invention, and the like.

Combinations with Other Active Substances or Treatments

An antibody molecule of the invention, or the combination of an anti-PD1 antibody of the invention and an anti-LAG3 antibody of the invention, may be used on its own or in combination with one or more additional therapeutic agents, in particular selected from chemotherapeutic agents like DNA damaging agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the antibody molecule.

In certain embodiments, the additional therapeutic agent may be, without limitation, one or more inhibitors selected from the group of inhibitors of EGFR, VEGFR, HER2-neu, Her3, AuroraA, AuroraB, PLK and PI3 kinase, FGFR, PDGFR, Raf, Ras, KSP, PDK1, PTK2, IGF-R or IR.

Further examples of additional therapeutic agents are inhibitors of CDK, Akt, src/bcr abl, cKit, cMet/HGF, c-Myc, Flt3, HSP90, hedgehog antagonists, inhibitors of JAK/STAT, Mek, mTor, NFkappaB, the proteasome, Rho, an inhibitor of wnt signaling or an inhibitor of the ubiquitination pathway or another inhibitor of the Notch signaling pathway.

Examples for Aurora inhibitors are, without limitation, PHA-739358, AZD-1152, AT 9283, CYC-116, R-763, VX-680, VX-667, MLN-8045, PF-3814735.

An example for a PLK inhibitor is GSK-461364.

Examples for raf inhibitors are BAY-73-4506 (also a VEGFR inhibitor), PLX 4032, RAF-265 (also in addition a VEGFR inhibitor), sorafenib (also in addition a VEGFR inhibitor), and XL 281.

Examples for KSP inhibitors are ispinesib, ARRY-520, AZD-4877, CK-1122697, GSK 246053A, GSK-923295, MK-0731, and SB-743921.

Examples for a src and/or bcr-abl inhibitors are dasatinib, AZD-0530, bosutinib, XL 228 (also an IGF-1R inhibitor), nilotinib (also a PDGFR and cKit inhibitor), imatinib (also a cKit inhibitor), and NS-187.

An example for a PDK1 inhibitor is BX-517.

An example for a Rho inhibitor is BA-210.

Examples for PI3 kinase inhibitors are PX-866, BEZ-235 (also an mTor inhibitor), XL 418 (also an Akt inhibitor), XL-147, and XL 765 (also an mTor inhibitor).

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, and AV-299.

An example for a c-Myc inhibitor is CX-3543.

Examples for Flt3 inhibitors are AC-220 (also an inhibitor of cKit and PDGFR), KW 2449, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are tanespimycin, alvespimycin, IPI-504 and CNF 2024.

Examples for JAK/STAT inhibitors are CYT-997 (also interacting with tubulin), TG 101348 (also an inhibitor of Flt3), and XL-019.

Examples for Mek inhibitors are ARRY-142886, PD-325901, AZD-8330, and XL 518.

Examples for mTor inhibitors are temsirolimus, AP-23573 (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are AB-1010, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), XL-999 (also an inhibitor of Flt3, PDGFR, VEGFR, FGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609 and CUR-61414.

Examples for CDK inhibitors are seliciclib, AT-7519, P-276, ZK-CDK (also inhibiting VEGFR2 and PDGFR), PD-332991, R-547, SNS-032, PHA-690509, and AG 024322.

Examples for proteasome inhibitors are bortezomib, carfilzomib, and NPI-0052 (also an inhibitor of NFkappaB).

An example for an NFkappaB pathway inhibitor is NPI-0052.

An example for an ubiquitination pathway inhibitor is HBX-41108.

In preferred embodiments, the additional therapeutic agent is an anti-angiogenic agent.

Examples for anti-angiogenic agents are inhibitors of the FGFR, PDGFR and VEGFR or the respective ligands (e.g VEGF inhibitors like pegaptanib or the anti-VEGF antibody bevacizumab), and thalidomides, such agents being selected from, without limitation, nintedanib, bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs (immunomodulatory drugs), thalidomide derivative CC-4047, lenalidomide, ENMD 0995, IMC-D11, Ki 23057, brivanib, cediranib, XL-999 (also an inhibitor of cKit and Flt3), 1B3, CP 868596, IMC 3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, GW 786034, PF-337210, IMC-1121B, AVE-0005, AG-13736, E-7080, CHIR 258, sorafenib tosylate (also an inhibitor of Raf), RAF-265 (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL 880 (also an inhibitor of cMet), XL-647 (also an inhibitor of EGFR and EphB4), XL 820 (also an inhibitor of cKit), and nilotinib (also an inhibitor of cKit and brc-abl).

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, matuzumab; examples for a small molecule EGFR inhibitor, without limitation, are gefitinib, afatinib, osimertinib and olmutinib. Another example for an EGFR modulator is the EGF fusion toxin.

Among the EGFR and Her2 inhibitors useful for combination with the antibody molecule of the invention are lapatinib, gefitinib, erlotinib, cetuximab, trastuzumab, nimotuzumab, zalutumumab, vandetanib (also an inhibitor of VEGFR), pertuzumab, XL-647, HKI-272, BMS-599626 ARRY-334543, AV 412, mAB-806, BMS-690514, JNJ-26483327, AEE-788 (also an inhibitor of VEGFR), ARRY-333786, IMC-11F8, Zemab.

Other agents that may be advantageously combined in a therapy with the antibody molecules of the invention are tositumumab and ibritumomab tiuxetan (two radiolabelled anti-CD20 antibodies), alemtuzumab (an anti-CD52 antibody), denosumab, (an osteoclast differentiation factor ligand inhibitor), galiximab (a CD80 antagonist), ofatumumab (a CD20 inhibitor), zanolimumab (a CD4 antagonist), SGN40 (a CD40 ligand receptor modulator), rituximab (a CD20 inhibitor) or mapatumumab (a TRAIL-1 receptor agonist).

Other chemotherapeutic drugs that may be used in combination with the antibody molecules of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortisone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5 fluorouracil, capecitabine, decitabine, nelarabine, and gemcitabine, purine and adenosine analogues such as mercaptopurine thioguanine, cladribine and pentostatin, cytarabine, fludarabine); antitumor antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

In certain embodiments, the additional therapeutic agent may be a further immunotherapeutic agent, such as modulators of the following checkpoint inhibitors: TIM3, PD-L1 (e.g. atezolizumab, avelumab or durvalumab), PD-L2, CTLA-4, VISTA, BTLA, TIGIT, CD160, LAIR1, 2B4, CEACAM.

In other embodiments the immunotherapeutic agent may be a cancer vaccine.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation, and methods of preparing, the antibodies of the invention for the combined use with the above combination partners. Also included are the preparation, and methods of preparing, the above-mentioned combination partners for the combined use with the antibodies of the invention.

The antibody molecules of the invention may be used on their own or in combination with other treatment regimes, for example surgery and/or radiation therapy.

Kits and Methods of Manufacture and Purification

The invention also encompasses kits comprising at least one antibody of the invention and one or more other components selected from the group consisting of other drugs used for the treatment of the diseases and disorders as described above.

In one embodiment, the kit includes a composition containing an effective amount of an anti-PD1 antibody molecule of the invention in unit dosage form. In another embodiment, the kit includes a composition containing an effective amount of an anti-LAG3 antibody molecule of the invention in unit dosage form. In a further embodiment the kit includes both a composition containing an effective amount of an anti-PD1 antibody molecule of the invention in unit dosage form and a composition containing an effective amount of an anti-LAG3 antibody molecule of the invention in unit dosage form.

In some embodiments, the kit comprises a sterile container which contains such a composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, an antibody molecule of the invention, or a combination of both types of antibodies of the invention, are provided together with instructions for administering the antibody/antibodies to a subject having cancer. The instructions will generally include information about the use of the composition for the treatment or prevention of an cancer. In other embodiments, the instructions include at least one of the following: description of the therapeutic agent; dosage schedule and administration for treatment or prevention of cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention further provides methods of manufacturing an antibody molecule of the invention, such methods generally comprising the steps of:
  culturing host cells comprising an expression vector comprising a nucleic acid encoding an antibody molecule of the invention under conditions that allow formation of the antibody of the invention; and,
  recovering the antibody molecule expressed by the host cells from the culture; and
  optionally further purifying and/or modifying and/or formulating the antibody molecule of the invention.

A nucleic acid of the invention can e.g. be a DNA molecule comprising coding sequences as well as regulatory sequences and optionally natural or artificial introns, or can be a cDNA molecule. It may have its original codons or may have an optimized codon usage that has been specifically adapted for expression in the intended host cell or host organism. According to one embodiment of the invention, the nucleic acid of the invention is in essentially isolated form, as defined above.

The nucleic acid of the invention will typically be incorporated into an expression vector, i.e. a vector that can provide for expression of the polypeptide when transfected into a suitable host cell or other expression system.

For manufacturing the antibodies of the invention, the skilled artisan may choose from a great variety of expression systems well known in the art, e.g. those reviewed by Kipriyanow and Le Gall, 2004.

Expression vectors include plasmids, retroviruses, cosmids, EBV derived episomes, and the like. The expression vector and expression control sequences are selected to be compatible with the host cell. The antibody light chain gene and the antibody heavy chain gene can be inserted into separate vectors. In certain embodiments, both DNA sequences are inserted into the same expression vector.

Convenient vectors are those that encode a functionally complete human CH (constant heavy) or CL (constant light) immunoglobulin sequence, with appropriate restriction sites engineered so that any VH (variable heavy) or VL (variable light) sequence can be easily inserted and expressed, as described above. For the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA. The signal peptide may be an immunoglobulin signal peptide or a heterologous peptide from a non-immunoglobulin protein. Alternatively, the DNA sequence encoding the antibody chain may already contain a signal peptide sequence.

In addition to the antibody chain DNA sequences, the recombinant expression vectors typically carries regulatory sequences, optionally heterologous regulatory sequences, including promoters, enhancers, termination and polyadenylation signals and other expression control elements that control the expression of the antibody chains in a host cell. Examples for promoter sequences (exemplified for expression in mammalian cells) are promoters and/or enhancers derived from CMV (such as the CMV Simian Virus 40 (SV40) promoter/enhancer), adenovirus, (e. g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e. g. origins of replication) and selectable marker genes. Nucleic acid molecules encoding the heavy chain or an antigen-binding portion thereof and/or the light chain or an antigen-binding portion thereof of an antibody of the invention, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the heavy chain and the light chain are present on two expression vectors which are co-transfected into the host cell, preferably a mammalian cell.

Mammalian cell lines available as hosts for expression are well known in the art and include, inter alia, Chinese hamster ovary (CHO) cells, NS0, SP2/0 cells, HeLa cells, baby hamster kidney (BHK) cells, monkey kidney cells (COS), human carcinoma cells (e. g., Hep G2 and A-549 cells), 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used.

The antibody molecules of the invention are produced by culturing the host cells for a period of time sufficient to allow for expression of the antibody molecule in the host cells. Antibody molecules are preferably recovered from the culture medium as a secreted polypeptide or it can be recovered from host cell lysates if for example expressed without a secretory signal. It is necessary to purify the antibody molecules using standard protein purification methods used for recombinant proteins and host cell proteins in a way that substantially homogenous preparations of the antibody are obtained. By way of example, state-of-the art purification methods useful for obtaining antibody molecules of the invention include, as a first step, removal of cells and/or particulate cell debris from the culture medium or lysate. The antibody is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining an antibody molecule preparation, the purified antibody molecule may be dried, e.g. lyophilized, as described below for therapeutic applications.

EXAMPLES

Example 1: Generation of Mouse Antibodies Binding to PD1 and Blocking PDL-1 Binding to PD1

The extracellular domain (ECD) of human PD1 protein (amino acids 21-170 of GENBANK™ accession number AA063583.1) was synthesized and prepared as an immunogen. Mice were then immunized and then boosted with human PD1 ECD protein following standard laboratory immunization techniques.

Plasma was then harvested from the immunized mice and screened to identify individuals with sufficient titre of anti-PD1 immunoglobulin. Following standard laboratory methods, lymphocytes from the selected mice were harvested and fused with mouse myeloma cells to generate hybridomas. These hybridomas were subsequently screened to identify hybridomal lines which produced antibody molecules which exhibited binding in low nM affinity range to human PD1 (ECD), and also blocked the binding of human PD-L1 to PD1, using the assays described herein below.

Several hybridomas which produced antibodies that bound to human PD1 and blocked binding to human PD-L1 were selected, the antibody variable domains isolated and cloned using standard PCR primer sets.

From this study a murine hybridomal line, termed 77E11, was identified which produced monoclonal antibodies exhibiting low nM binding affinities to human PD1 (ECD) and also blocked the binding of PD-L1 to PD1.

The amino acids sequence of the variable domain of monoclonal antibody produced by 77E11 is shown in FIGS. 1a and 1b.

Example 2: Generation of Humanized Anti-PD1 Antibodies

V-genes of murine 77E11 hybridomal cell line were identified following PCR and sequencing protocols well known in the art. The V-genes were then fused to closest matching human germline genes, using standard molecular biology techniques. In the case of 77E11, this resulted in chimeric murine/human antibody molecules having of mouse Vk and Vh amino acid residues fused to human Ck and Ch1 amino acid residues.

Once prepared, the chimeric murine/human antibody was then subjected to "humanization" protocols. Here, mutated amino acid libraries of the chimeric 77E11 Fab clones were prepared. Additional library positions were also prepared so as to remove sequence liabilities (i.e. amino acid residues known to be immunogenic or to create potential manufacturing problems). These mutated libraries usually have 5 to 10 binary (mouse vs human) positions per V-region. Several smaller libraries can be built to address specific liabilities in more complex V-regions. Such libraries are prepared using standard methods in the art, and can be readily used by the skilled person.

Following completion of this stage, a number of different "humanized" Fabs derived from the original murine 77E11 Fab sequence were prepared. These humanized Fabs were tested for their ability to bind human PD1 and block the interaction of PD-L1 with PD1. Genetically engineered Fabs that perform equal to, or better than, the corresponding chimeric Fab were subsequently selected. Their amino acid sequence was analysed for percentage human sequence, probable immunogenicity, and removed sequence liabilities.

Following selection of the most favorable humanized Fabs, these were then placed in the human IgG4 (Pro) or IgG1KO immunoglobulin format. IgG4 (Pro) differs from canonical human IgG4 sequence by having serine 241 altered to proline, this alteration has been demonstrated to minimize dynamic Fab arm exchange between IgG4 molecules. IgG1 KO differs from canonical human IgG1 sequence by two amino acid substitutions (L234A, L235A) known to minimize effector function of antibody molecules.

On completion of this study, 5 different humanized versions of the original chimeric murine/human 77E11 Fab had been prepared. These are termed: PD1-1, PD1-2, PD1-3, PD1-4 and PD1-5.

The amino acids sequence of the CDRs for PD1-1, PD1-2, PD1-3, PD1-4 and PD1-5, the VH and VL sequences and the full HC and LC sequences are presented in the table at the end of this application. For the avoidance of doubt, a correlation between the antibodies and their SEQ ID number is also presented in the table below:

TABLE 1

| SEQ ID NOs for the anti-PD1 antibodies of the invention | | | | | |
|---|---|---|---|---|---|
| anti-PD1 antibody | CDR sequences | VH sequences | VL sequences | HC sequences | LC sequences |
| PD1-1 | 1-6 | 19 | 20 | 29 | 30 |
| PD1-2 | 7-12 | 21 | 22 | 31 | 32 |
| PD1-3 | 13-18 | 23 | 24 | 33 | 34 |
| PD1-4 | 13-18 | 25 | 26 | 35 | 36 |
| PD1-5 | 13-18 | 27 | 28 | 37 | 38 |

Example 3: Antibody Binding to Human PD1 and Blocking of PD1 Ligand Interaction

The binding of the representative humanized anti-PD1 antibodies derived from murine 77E11 hybridoma (as described in Example 2) to human PD1 was determined.

Binding affinities to recombinant monomeric human PD1 were measured by SPR using a ProteOn XPR36 instrument. PD1-1, PD1-2 and PD1-3 antibodies were captured on Protein A/G surfaces that was amine coupled to the surface. Human PD1 ECD was injected over the captured antibodies for 600 sec at a flowrate of 30 ul/min and a dissociation for 1200 sec. The concentrations of human PD1 ECD were 0 nM, 6.25 nM, 12.5 nM, 25 nM, 50 nM, and 100 nM. The background was subtracted from the raw data and sensorgrams were then fit globally to 1:1 Langmuir binding to provide affinity (KD) values.

Using that protocol, it was determined that antibodies PD1-1, PD1-2 and PD1-3 bind to human PD1 as presented in the table below.

TABLE 2

Binding to recombinant human PD1 ($K_D$, nM)

| Antibody | $K_D$, nM |
|---|---|
| PD1-1 | 16.6 |
| PD1-2 | 61.8 |
| PD1-3 | 6.0 |

PD1 antibodies of the invention were then tested for the ability to block binding of human PD-L1/2 to human PD1 expressed on the surface CHO cells. PD1 expressing CHO cells were incubated with fixed concentration of recombinant biotin labeled PD-L1 or PD-L2 in the presence of anti-PD1 antibodies of the invention (PD1- to PD1-5). The mixture was incubated for 1 hour at 37 degrees celsius. Cell bound PD-L1/L2 was detected with Europium labeled Streptavidin and fluorescence measured using Perkin Elmer Victor X4 plate reader. Data is displayed as percentage inhibition. 0% inhibition is defined as the fluorescence value of cells incubated with the ligand with no antibodies, and 100% inhibition was defined as the signal obtained with just cells without labeled ligands and antibodies. Percentage inhibition values were calculated in Excel and curve fitting was done with GraphPad Prism. Data points of the curve are mean values of triplicate measurements.

Figure 2B:
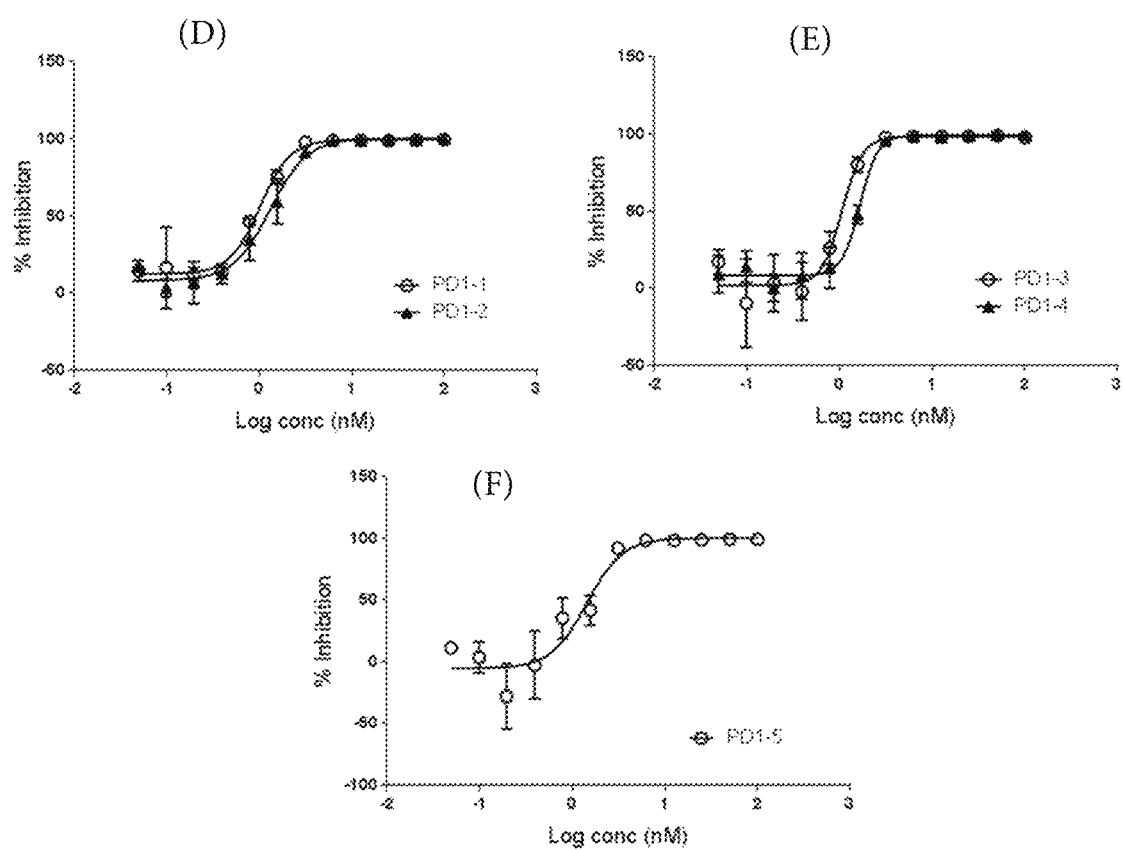

Inhibition curves and mAb concentrations needed to achieve 90% inhibition ($IC_{90}$) of ligand blocking are shown in FIGS. 2a and 2b and Table 3.

TABLE 3

Ligand blocking activities of PD1 mAbs

| Antibody | PD-L1 $IC_{90}$ (nM) | PD-L2 $IC_{90}$ (nM) |
|---|---|---|
| PD1-1 | 2.12 | 2.09 |
| PD1-2 | 2.97 | 3.64 |
| PD1-3 | 1.68 | 1.95 |
| PD1-4 | 2.04 | 2.71 |
| PD1-5 | 2.09 | 3.31 |

From this analysis it is clear that the humanized PD1 antibodies of the invention exhibit potent binding properties to PD1, and also efficiently inhibited the interaction of PD-1 with PD-L1 and PD-L2.

Example 4: Stimulation of Antigen-Specific T Cell Response by Anti-PD1 Antibody

Humanized anti-PD1 antibodies prepared according to the methods described above were subsequently tested for their ability to stimulate cytokine production of Tetanus specific CD4 memory T cells.

Figure 3:
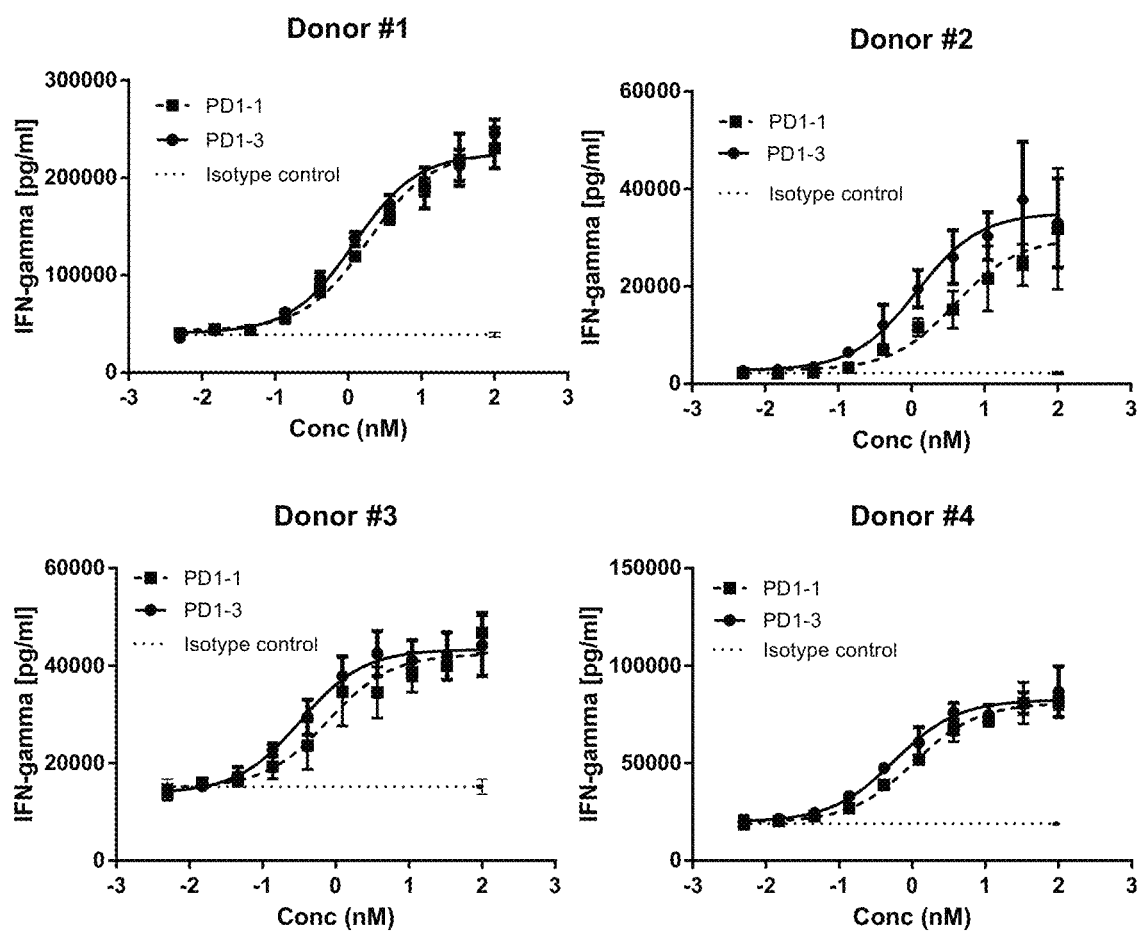
FIG. 3: Stimulation of antigen-specific T cell response by anti-PD1 antibody molecules. Shows the ability of anti-PD1 antibodies of the invention to stimulate interferon-gamma (IFN-gamma) production of tetanus specific CD4 memory T cells from four individual donors (Donors #1 to #4). For this assay, T cells from PBMCs derived from healthy donors were expanded in the presence of tetanus toxoid and co-cultured with autologous mature dendritic cells (DCs) loaded with tetanus toxoid for 2 days. The co-culture step was repeated a second time in a similar manner in the presence of PD1-1 and PD1-3. At the end of the second co-culture step supernatants were assessed for IFN-gamma levels by ELISA.

For this assay, T cells from PBMCs derived from healthy donors were expanded in the presence of tetanus toxoid and co-cultured with autologous mature dendritic cells (DCs) loaded with tetanus toxoid for 2 days. The co-culture step was repeated a second time in a similar manner in the presence of representative anti-PD1 antibodies of the invention. At the end of the second co-culture step, supernatants were analysed for IFN-gamma by ELISA and results are shown in FIG. 3.

All the PD1 antibodies of the invention tested show a clear dose dependent very potent activation of T cells as measured by IFN-gamma release. When the PD1 antibodies of the invention are combined with anti-LAG3 antibodies, superior activity can be observed when compared to reference prior art anti-PD1 antibody combinations (see Example 12 and FIG. 8).

Example 5: Epitope Mapping of the Humanized Anti-PD1 Monoclonal Antibodies

The epitope of a representative anti-PD1 antibody of the invention and a reference prior art antibody molecule having the same amino acid sequence as nivolumab were analyzed by hydrogen-deuterium exchange (HDX) experiments, which reveals epitope differences at individual amino acid level in antibody epitopes.

HDX analysis showed that the anti-PD1 antibody of the invention and the reference prior art antibody molecule bind to similar and overlapping regions of human PD1. However, the epitopes are not identical, with representative PD1 antibody of the invention binding to an additional sequence element as detailed in Table 4.

TABLE 4

Epitope Mapping of anti-PD1 antibody molecules by Hydrogen-Deuterium Exchange Mass Spectrometry

| Antibody | PD-1 Binding Regions (aa*) | Epitope |
|---|---|---|
| reference antibody for nivolumab | 125-138 | $A_{125}$ISLAPKAQIKESL\*\* (SEQ ID NO: 115) |
| PD1-3 | 80-95, 125-138 | AAFPEDRSQPGQDCRF (SEQ ID NO: 116) $A_{125}$ISLAPKAQIKESL\*\* (SEQ ID NO: 115) |

*PD1 used for numbering: GENBANK™ AA063583.1
Amino acids involved in binding are shown in bold**, differences are underlined Example 6: In Vivo Efficacy of Anti-PD1 Antibody Molecules of the Invention in a hPD-1 Knock-in Mouse Model The purpose of the study was to measure the efficacy of the anti-PD1 antibody molecules of the invention using a fully immune competent mouse harboring a genetic modification which replaces the extracellular domain of mouse PD1 with the corresponding region of human PD1. The mouse C57BL/6NTac-PDCD1$^{tm(PDCD1)Arte}$ used for this experiment was provided by ISIS INNOVATION LIMITED, Oxford, England and is termed from now on "hPD1 knock in mouse".

MC-38 cells were subcutaneously injected into the flank of hPD1 knock-in mice and treatment started at day 6 post cell injection. The mice received PBS, Isotype control or anti-PD1 antibody molecule of the invention at a dose of 10 mg/kg twice weekly (q3or4d) or PD1-3 was administered only once.

Figure 4A:
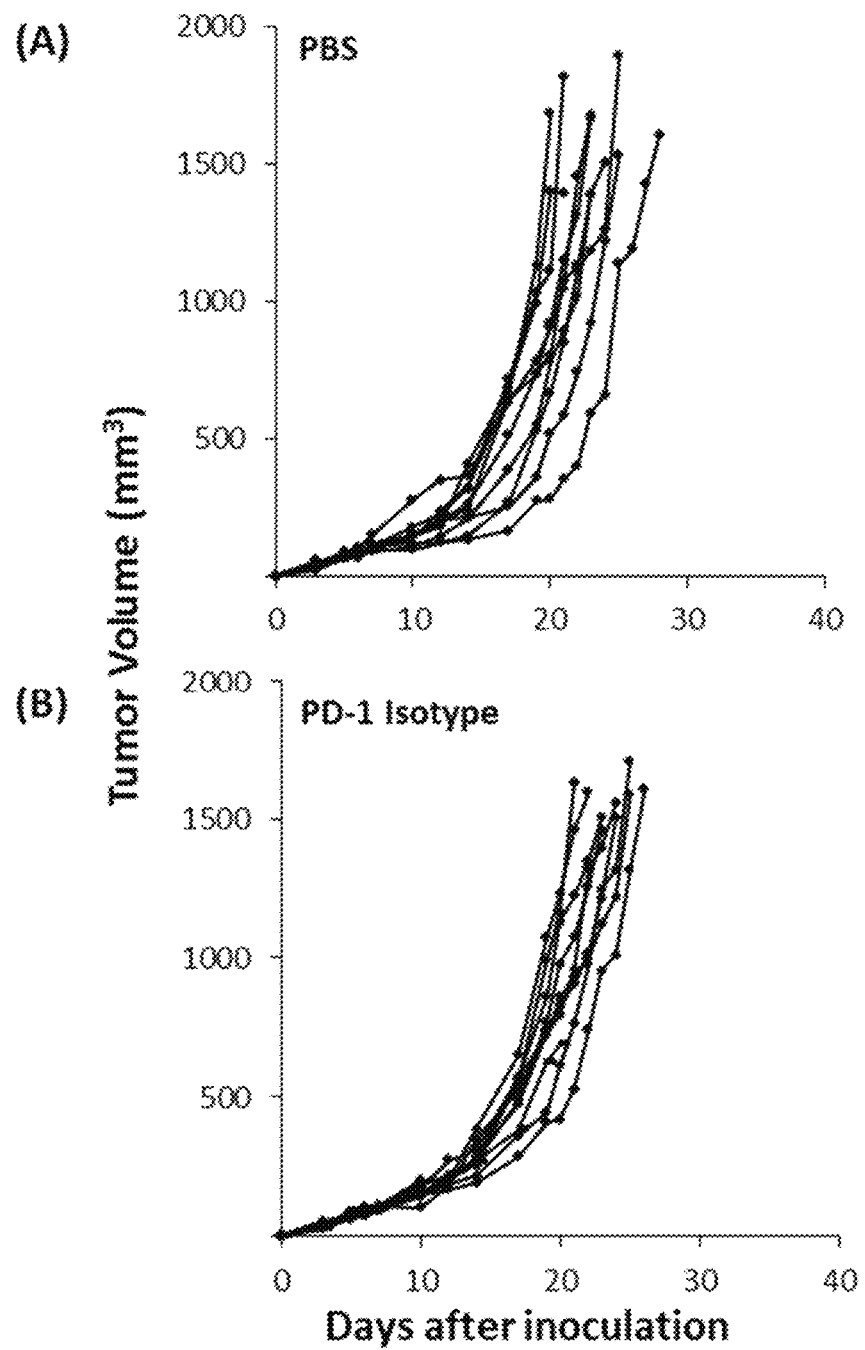
FIGS. 4a an 4b: In vivo efficacy of anti-PD1 antibody molecules in a hPD-1 knock-in mouse model. Shows individual tumor growth curves form colon carcinoma cell line (MC38) bearing mice. Mice were treated with (FIG. 4a(A)) PBS q3or4d, (FIG. 4a(B)) Isotype q3or4d, (FIG. 4b(C)) PD1-3 q3or4d or (FIG. 4b(D)) PD1-3 as single dose. PD1-3 and the Isotype were dosed at 10 mg/kg.
Figure 4B:
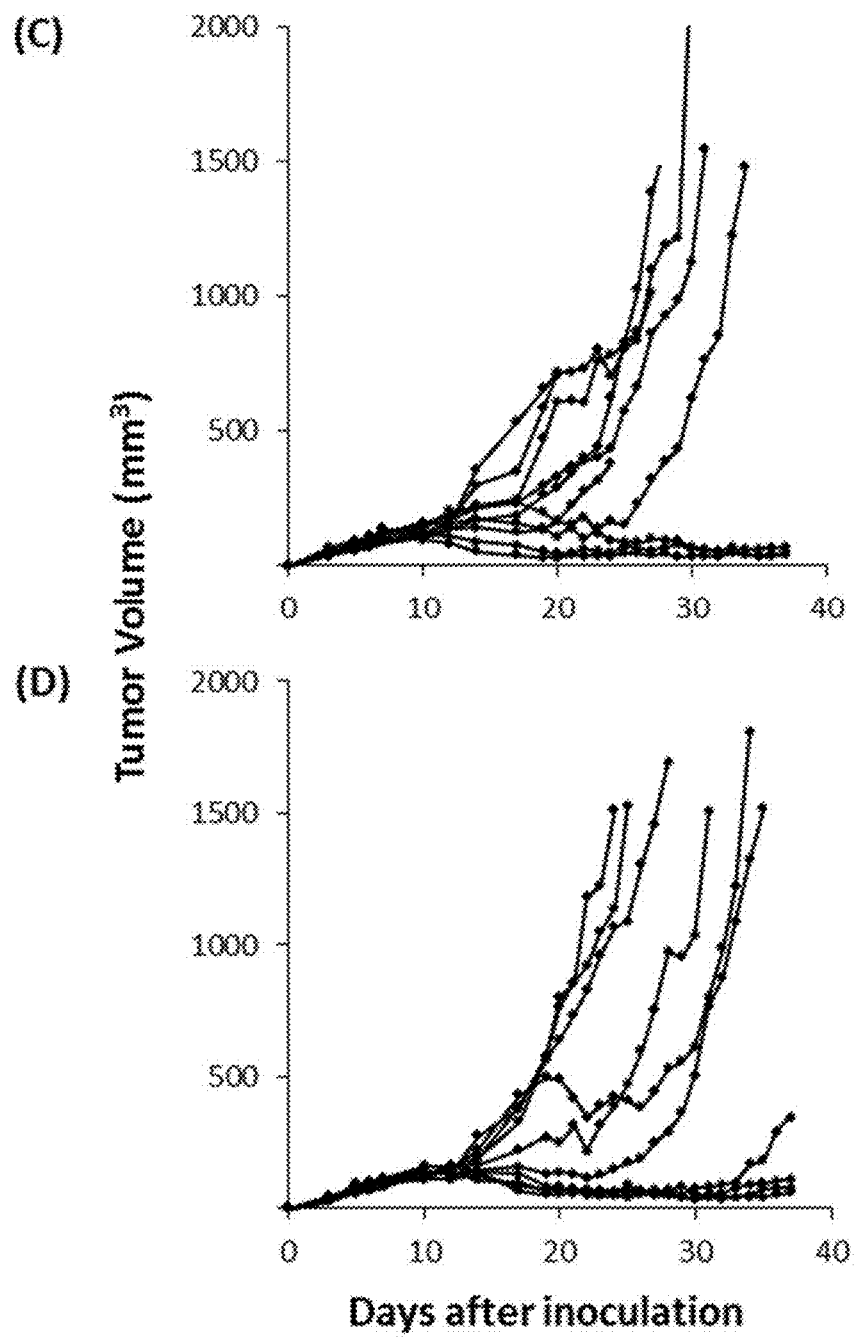
Figure 9A:
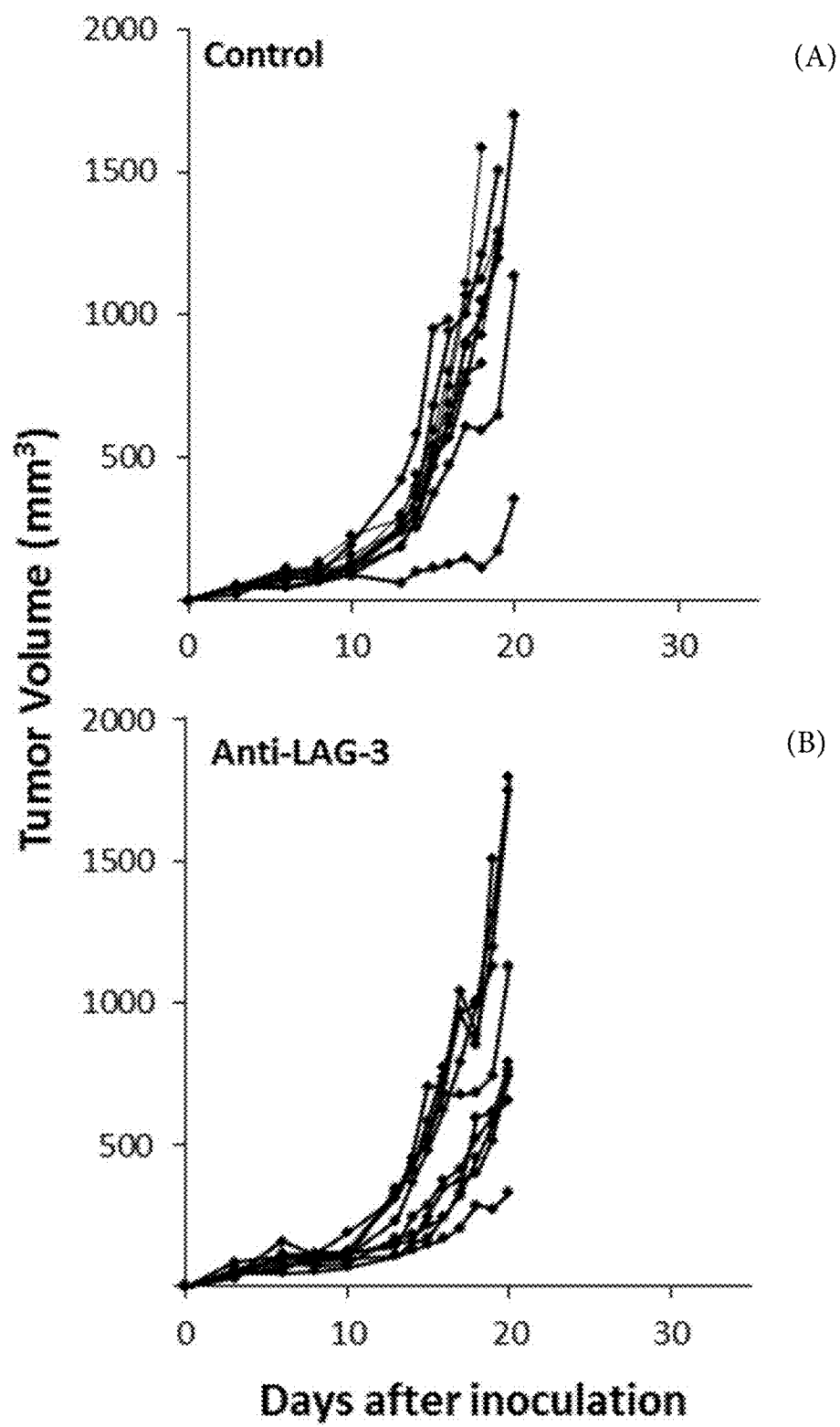
FIGS. 9a to 9j: In vivo efficacy of combination therapy of PD1 and LAG3 antibodies in syngeneic tumor models. Shown are individual growth curves of tumor bearing mice which were treated with tool antibodies twice weekly at a dose of 10 mg/kg.
Figure 9B:
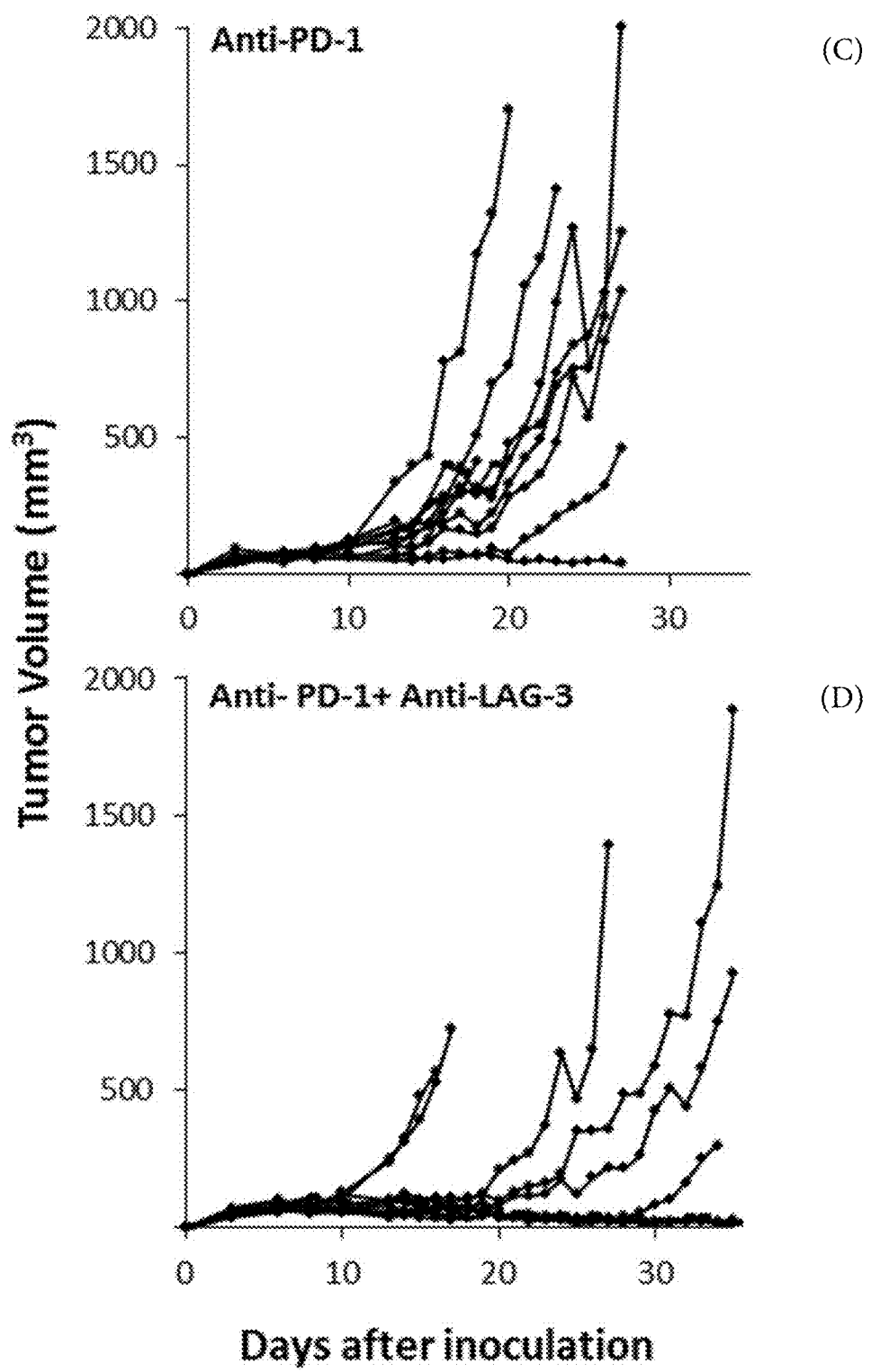
Figure 9C:
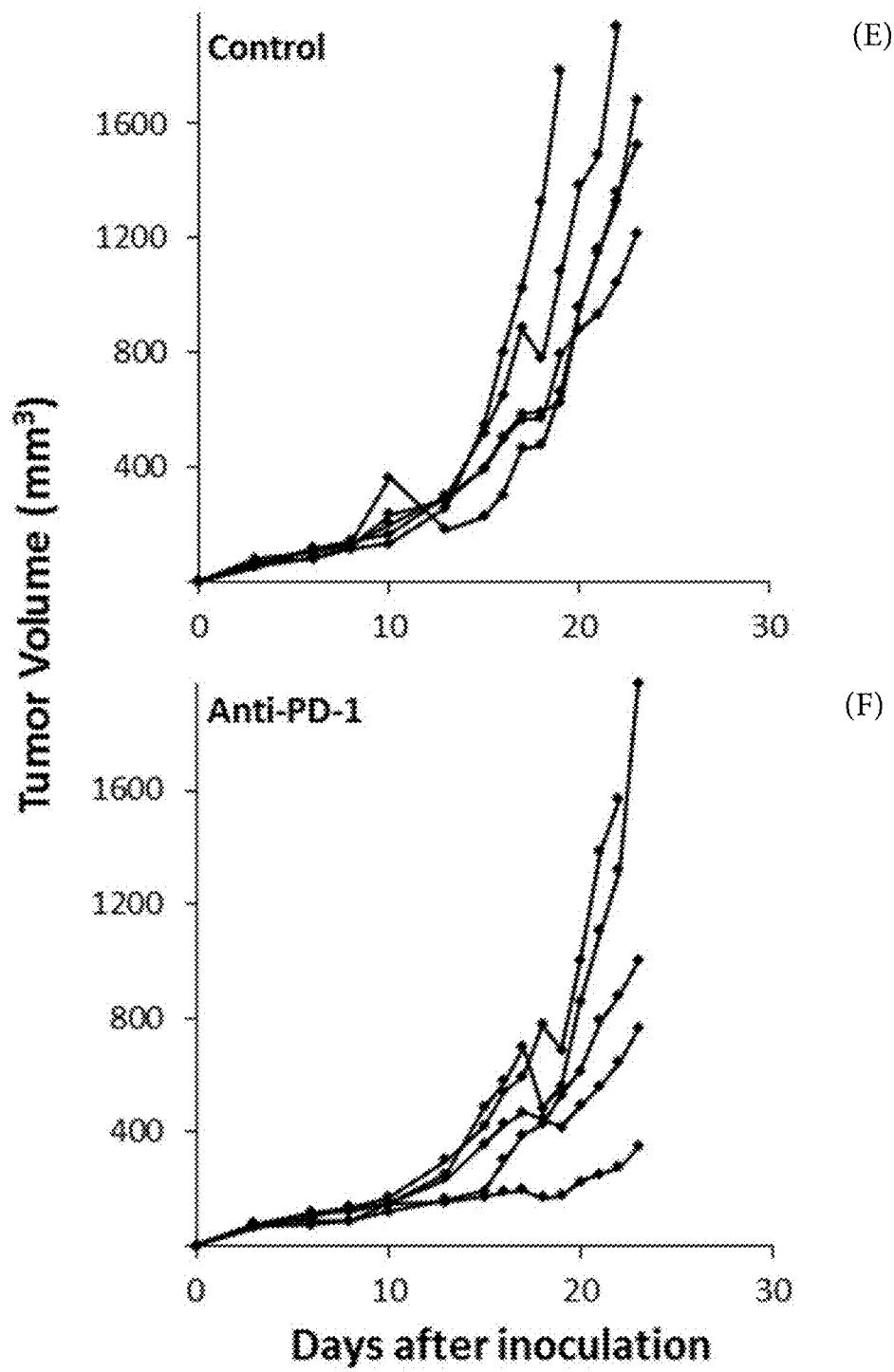
Figure 9D:
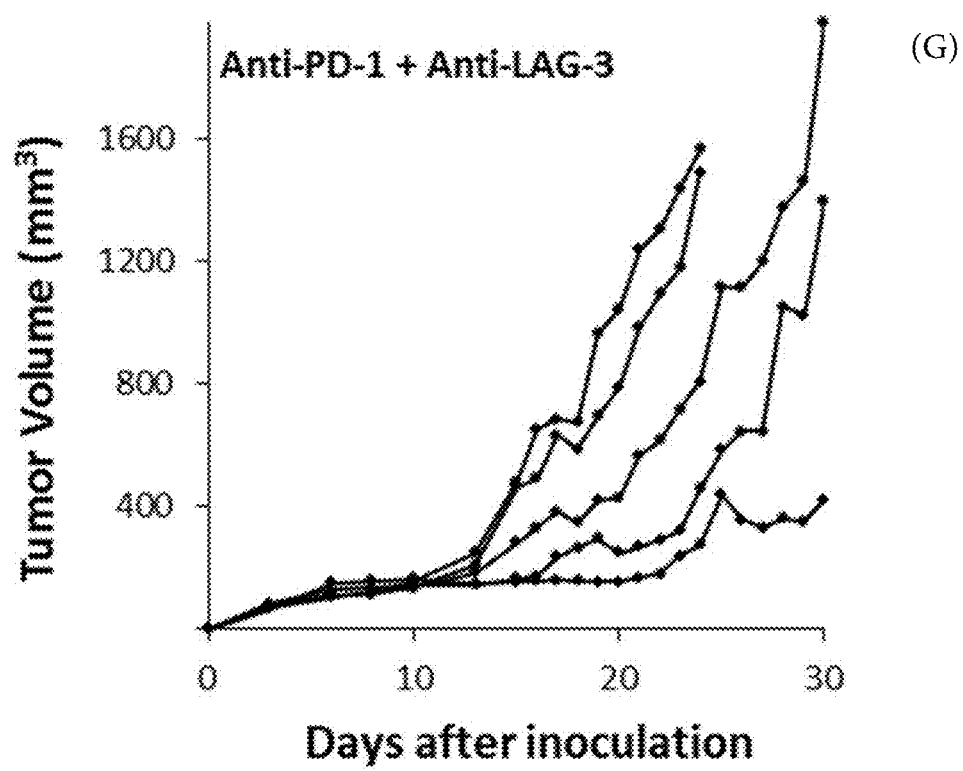
Figure 9E:
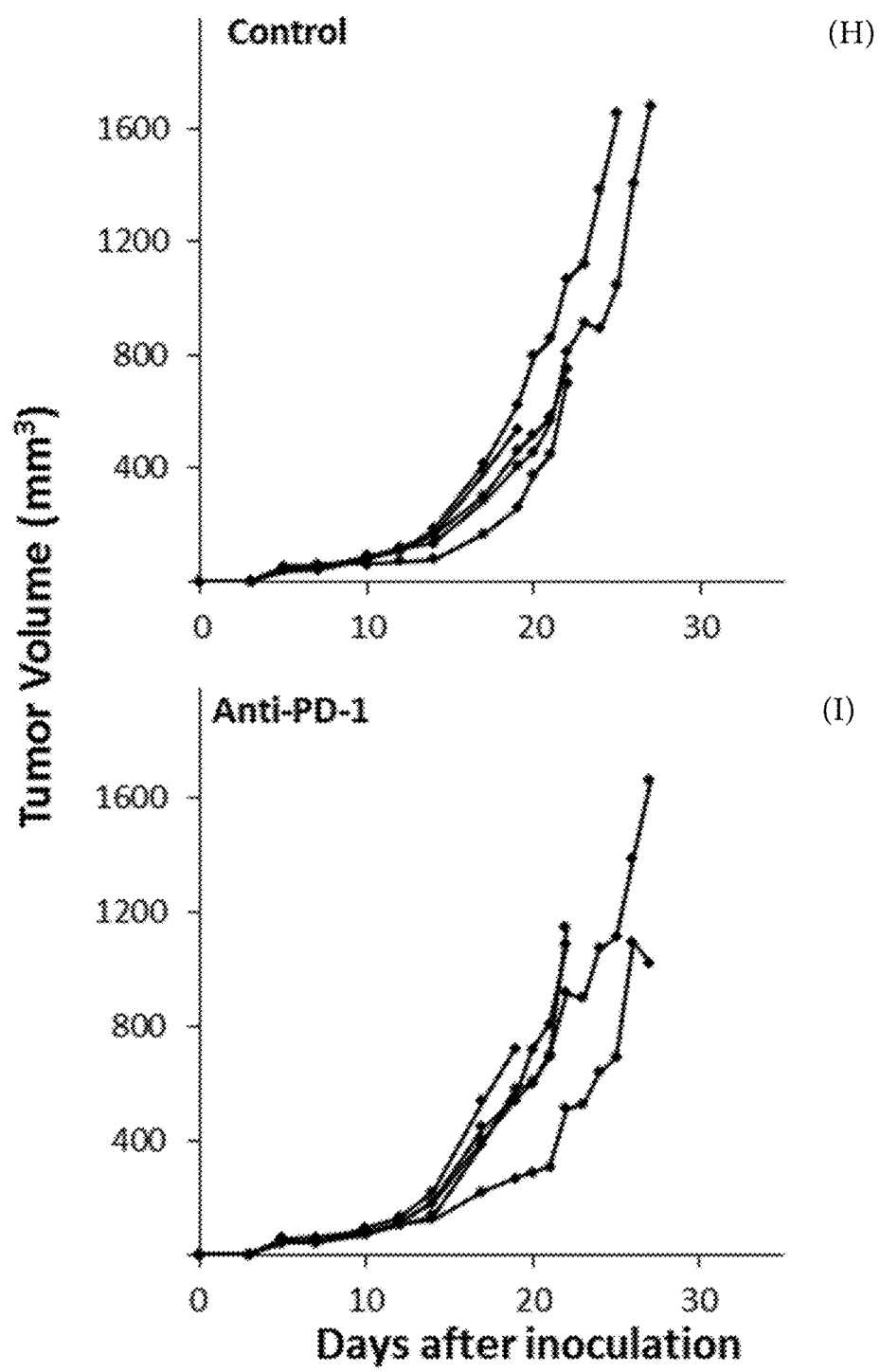
Figure 9F:
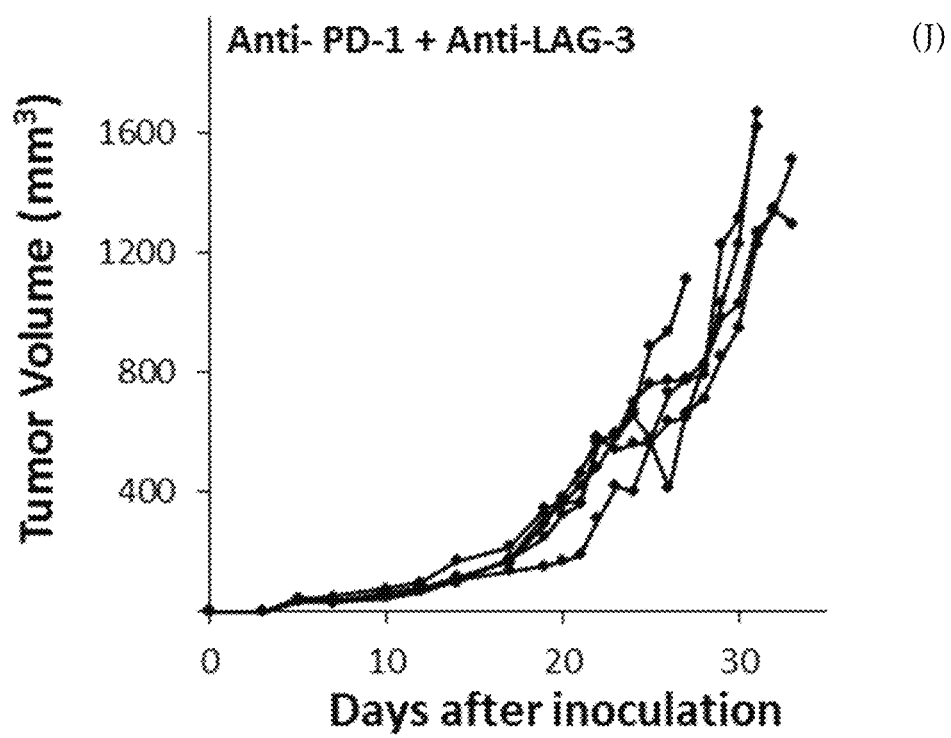
Figure 9G:
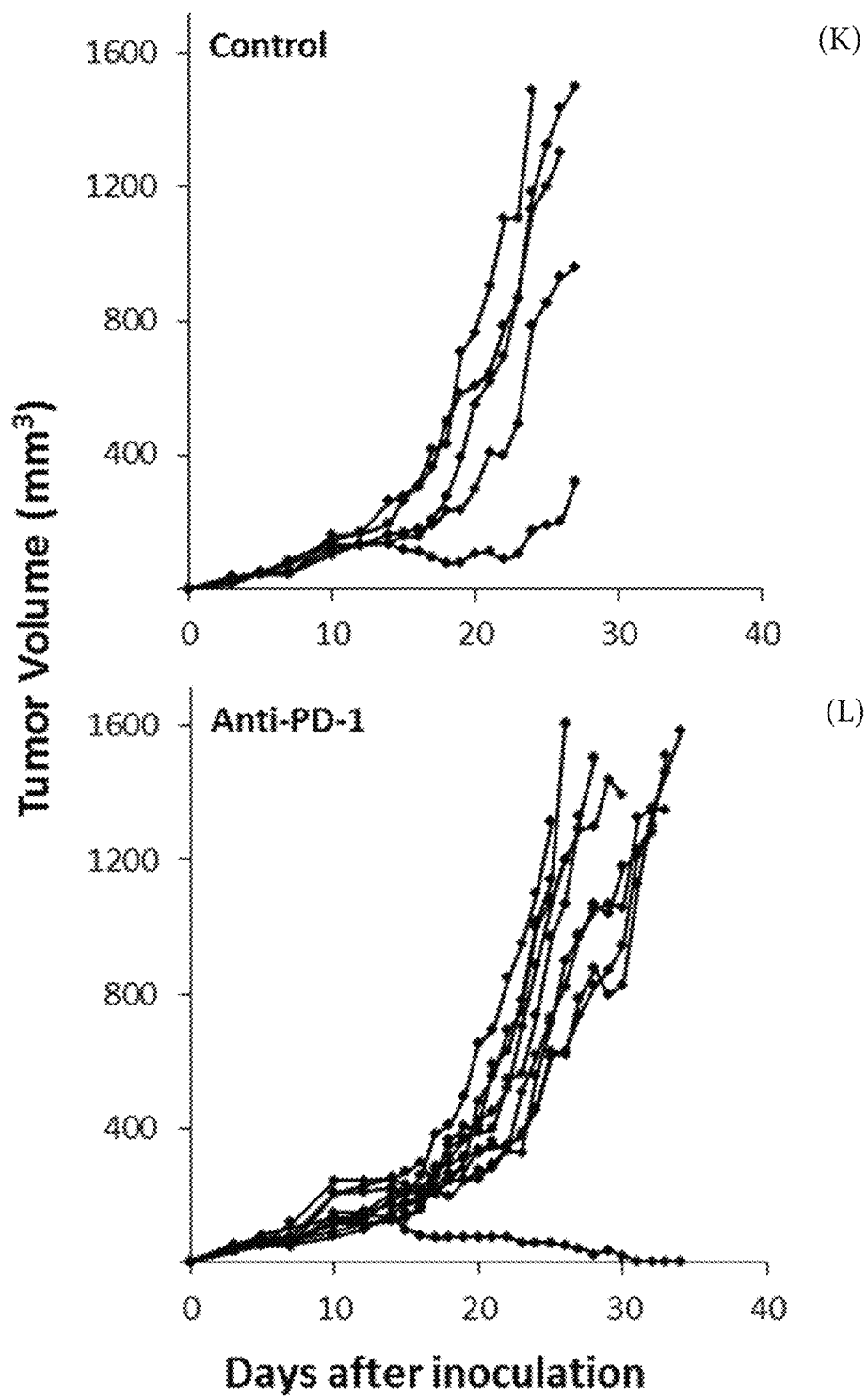
Figure 9H:
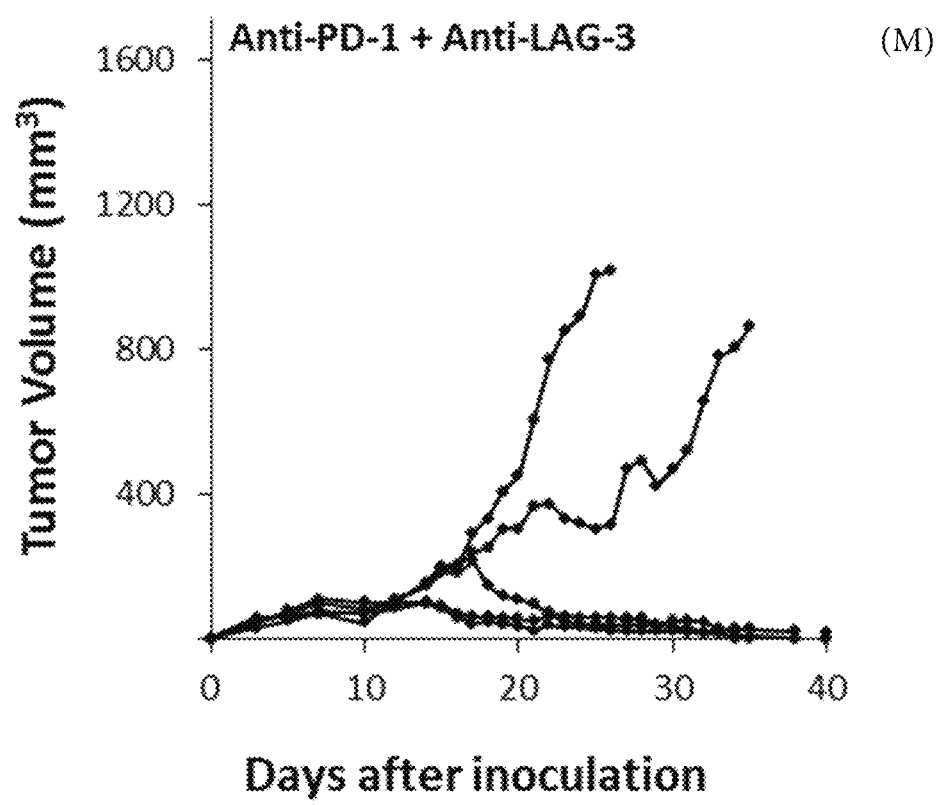
Figure 9I:
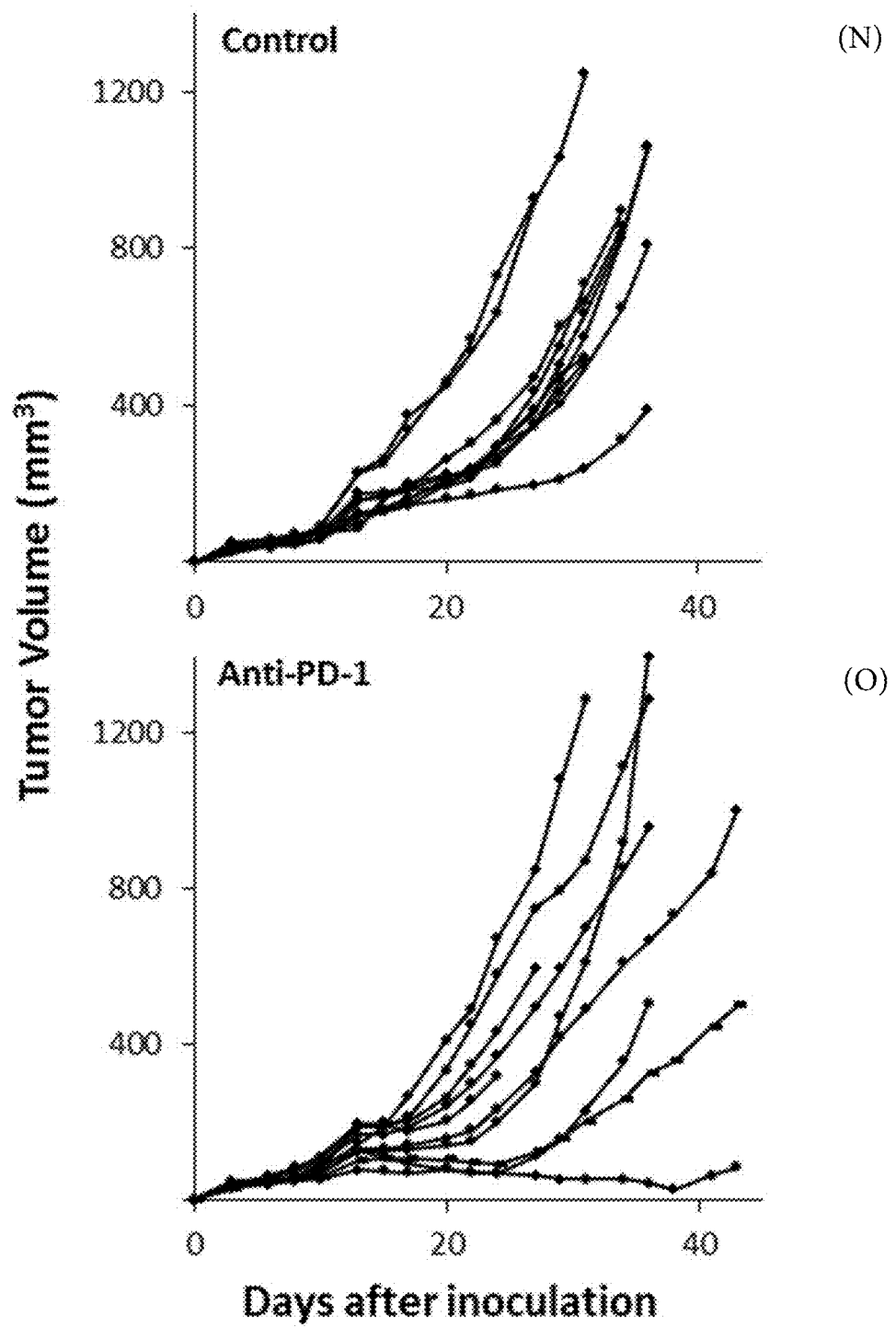
Figure 9J:
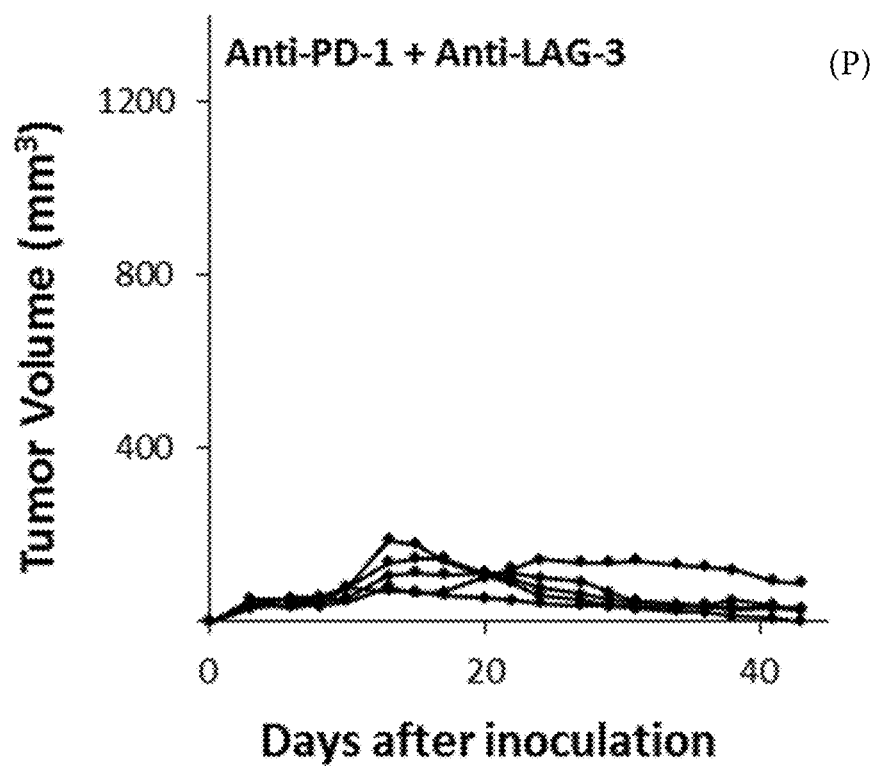

FIGS. 4a and 4b show the tumor volume over time for individual hPD1 knock-in mice implanted with MC38 and Table 5 summarizes tumor growth inhibition (TGI) at day 23 post cell injection and complete responses observed at the end of the study.

Complete response (CR) is defined when (i) the tumor size is the same or smaller compared to the first measurement and (ii) visual inspection of residual carrier material (matrigel) shows no tumor tissue. It could be demonstrated that the single dosing regimen of PD1-3 showed strong and anti-tumor effects (TGI-90%; with 2 mice showing a CR) equivalent as compared to twice weekly dosing regimen. This study shows that even a single dose of anti-PD1 antibody molecule of the invention is sufficient to achieve efficacy, which could be a consequence of longer half-life.

TABLE 5

TGI for PD1

| | TGI [%] | CR [n/10] |
| --- | --- | --- |
| PBS | — | 0 |
| PD-1 Isotype | 12 | 0 |
| PD1-3 (q3or4d) | 83 | 3 |
| PD1-3 (once) | 90 | 2 |

Example 7: Preclinical Pharmacokinetics of Anti-PD1 Antibody Molecules of the Invention Pharmacokinetic (PK) properties of the anti-PD1 antibody molecule of the invention were determined in a single dose i.v. PK study in Cynomolgus monkeys.

Anti-PD1 antibody molecule of the invention administered with a dose of 1 mg/kg i.v. displays a mean plasma clearance (CL) of 0.28 ml/h/kg. The mean volume of distribution (Vss) for PD1-3 was 58 ml/kg. The mean terminal half-life for PD1-3 was 11 d.

AUC and $c_{max}$ of PD1-3 at 1 mg/kg in Cynomolgus monkeys are nearly identical to the corresponding parameters of the IgG4Pro PD-1 antibodies nivolumab (BMS-936558, published in Wang, C. et al., Cancer Immunol. Res. 2:846-856, 2014) and pembrolizumab (MK-3475, published in FDA BLA document 125514Orig1s000 Pharmacology Review, 2014) in a comparable dose range.

Surprisingly and unexpectedly, the terminal half-live observed for PD1-3 was 1.5-2-fold higher than for nivolumab as shown in FIGS. 5a and 5b. This suggests that the anti-PD1 antibodies of the invention have a serum half-life of 11 days. This is in contrast to the known reference anti-PD1 antibody molecules which typically have a half-life of 4 to 6 days in the dose range 0.3-3 mg/kg. This surprising feature of the antibody molecules of the invention may allow for a patient to be treated with the antibody molecules of the invention less frequently than those of the art, which can translate to a reduction in the amount of antibody which has to be supplied, either in the form of reduced frequency of administration or in reduced amount of antibody to be used. Given that anti-PD1 antibody molecules can induce unwanted side effects in patients, as discussed above, then the anti-PD1 antibodies of the invention may have a significant and surprising clinical advantage over the art.

Example 8: Identification of Mouse Antibodies Binding to LAG3

The extracellular domain (ECD) of human LAG3 protein (amino acids 23-450 of GENBANK™ accession number NP_002277) was synthesized and prepared as an immunogen. Mice were then immunized and then boosted with human LAG3 ECD protein following standard laboratory immunization techniques.

Plasma was then harvested from the immunized mice and screened to identify individuals with sufficient titre of anti-LAG3 immunoglobulin. Following standard laboratory methods, lymphocytes from the selected mice were harvested and fused with mouse myeloma cells to generate hybridomas.

Several hybridomas which produced antibodies that specifically bound to human LAG3 were selected, the antibody variable domains isolated and cloned using standard PCR primer sets.

From this study a murine hybridomal line, termed 496G6, which produced monoclonal antibodies exhibiting low nM binding affinities to human LAG3 (ECD) was identified and selected for further study.

The amino acids sequence of the variable domain of monoclonal antibody produced by 496G6 is shown in FIGS. 6a and 6b.

Example 9: Generation of Humanized Anti-LAG3 Antibodies

In this example, the methods and results for the development of humanized derivatives of the monoclonal antibody produced by murine hybridoma line 496G6, described in Example 8, are provided.

V-genes of murine 496G6 hybridoma were identified following PCR and sequencing protocols well known in the art. The V-genes are then fused to closest matching human germline genes, using standard molecular biology techniques. In the case of 496G6, this resulted in chimeric murine/human antibody having of mouse Vk and Vh amino acid residues fused to human Ck and Ch1 amino acid residues.

Once prepared, the chimeric murine/human antibody was then subjected to standard "humanization" protocols well known in the art. In this method, mutated amino acid libraries of the chimeric 496G6 Fab clones were prepared. Additional library positions were also prepared so as to remove sequence liabilities (i.e. amino acid residues known to be immunogenic or to create potential manufacturing problems). These mutated libraries usually have 5 to 10 binary (mouse vs human) positions per V-region. Several smaller libraries can be built to address specific liabilities in more complex V-regions. Such libraries are prepared using standard methods in the art, and can be readily used by the skilled person.

Following completion of this stage, a number of different "humanized" Fabs derived from the original murine 496G6 Fab sequence were prepared. These humanized Fabs were tested for their ability to bind human LAG3 and block the interaction of MHCII with LAG3. Genetically engineered Fabs that perform equal to, or better than, the corresponding chimeric Fab were subsequently selected. Their amino acid sequence was analysed for percentage human sequence, probable immunogenicity, and removed sequence liabilities.

Following selection of the most favourable humanized Fabs, these were then placed in the Human IgG4 (Pro) immunoglobulin format. IgG4 (Pro) differs from canonical Human IgG4 sequence by having serine 241 altered to proline, this alteration has been demonstrated to minimize dynamic Fab arm exchange between IgG4 molecules.

On completion of this study, 5 different humanized antibody versions of the original chimeric murine/human 496G6

Fab had been prepared. These were termed: LAG3-1, LAG3-2, LAG3-3, LAG3-4 and LAG3-5.

The amino acids sequence of the CDRs for LAG3-1, LAG3-2, LAG3-3, LAG3-4, LAG3-5, the VH and VL sequences and the full HC and LC sequences are presented in the table at the end of this application. For the avoidance of doubt, a correlation between the antibodies and their SEQ ID number is also presented in the table below:

TABLE 6

SEQ ID NOs for the anti-LAG3 antibodies of the invention

| anti-LAG3 antibody | CDR sequences | VH sequences | VL sequences | HC sequences | LC sequences |
|---|---|---|---|---|---|
| LAG3-1 | 39-44 | 51 | 52 | 61 | 62 |
| LAG3-2 | 39-44 | 53 | 54 | 63 | 64 |
| LAG3-3 | 39-44 | 55 | 56 | 65 | 66 |
| LAG3-4 | 39-44 | 57 | 58 | 67 | 68 |
| LAG3-5 | 45-50 | 59 | 60 | 69 | 70 |

Example 10: Antibody Binding to Human LAG3 and Blocking of LAG3 Ligand Interaction Binding affinities to recombinant monomeric human LAG3 were measured using SPR.

LAG3-1, LAG3-2, LAG3-3, LAG3-4 and LAG3-5 antibodies were captured on Protein A/G surfaces. Human LAG3 ECD-Fc was injected over the captured antibodies for 300 sec at a flowrate of 30 ul/min and a dissociation for 1800 sec. The concentrations of human LAG3 ECD were 0 nM, 0.625 nM, 1.25 nM, 2.5 nM, and 5 nM. The background was subtracted from the raw data and sensorgrams were then fit globally to 1:1 Langmuir binding to provide affinity (KD) values.

Using this protocol, antibodies LAG3-1, LAG3-2, LAG3-3, LAG3-4 and LAG-3-5 were determined to bind to human LAG-3 with high affinity, as presented in the table below.

TABLE 7

Binding to recombinant human LAG3 ($K_D$, nM)

| Antibody | $K_D$, nM |
|---|---|
| LAG3-1 | 0.125 |
| LAG3-2 | 0.09 |
| LAG3-3 | 0.12 |
| LAG3-4 | 0.1 |
| LAG3-5 | 0.07 |

LAG3 antibodies of the invention were tested for blocking the binding of recombinant human LAG3 protein to Raji cells expressing its ligand MHC II using FACS. Recombinant human LAG3 extracellular domain fused to human Fc (hLAG3-hIgFc) was incubated with LAG3 antibodies LAG3-1, LAG3-2, LAG3-3, LAG3-4 and LAG3-5 for 15 minutes at room temperature (RT) prior to adding to Raji cells followed by further incubation for 30 minutes at 4° C. Cells were washed 3 times. HLAG3-mIgFc binding to Raji cells was detected using a PE labelled anti-human IgG. Analysis of HLAG3-mIgFc binding was carried out with a FACS Canto I (BD Bioscience). The results are summarized in FIG. 7 and demonstrate that all LAG3 antibodies of the invention tested selectively and effectively inhibit the binding of LAG3 to MHC II.

Example 11: Epitope Mapping of the Humanized Anti-LAG3 Monoclonal Antibodies

The epitope of a representative anti-LAG3 antibody of the invention and a reference antibody molecule having the same amino acid sequence as BMS-986016 (a prior art reference anti-LAG3 antibody molecule) were analyzed using a "competition binding" assay. The results showed no competition for binding to LAG3, which shows that the anti-LAG3 antibody of the invention binds to a different epitope than the prior art reference anti-LAG3 antibody molecule.

The epitope of representative anti-LAG3 antibody of the invention was further refined by hydrogen-deuterium exchange (HDX) experiments, which reveals epitope differences at individual amino acid level in antibody epitopes.

HDX analysis showed that the representative anti-LAG3 antibody of the invention binds to two distinct regions of human LAG3 as detailed in the Table 8.

TABLE 8

Epitope Mapping of anti-LAG3 mAbs by Hydrogen-Deuterium Exchange Mass Spectrometry

| Antibody | LAG3 Binding Regions (aa*) | Epitope |
|---|---|---|
| LAG3-1 | 33-40 and 125-135 | LLRRAGVT (SEQ ID NO: 111) and YRAAVHLRDRA (SEQ ID NO: 112) |

*LAG-3 used for numbering: GENBANK™ NP_002277

Example 12: Stimulation of Antigen-Specific T Cell Response with Anti-PD1 and Anti-LAG3 Antibodies Individual anti-PD1 and anti-LAG3 antibodies of the invention, and combinations of these antibodies, were tested for their ability to stimulate cytokine production of Tetanus specific CD4 memory T cells by ELISA and compared with prior art anti-PD1 and anti-LAG3 antibodies For this assay, T cells from healthy donor PBMCs were expanded in the presence of tetanus toxoid and co-cultured with autologous mature dendritic cells (DCs) loaded with tetanus toxoid for 2 days. The co-culture step was repeated a second time in a similar manner in the presence of anti-PD1, anti-LAG3 and a combination of anti-PD1 and anti-LAG3 antibody molecules using fixed amount of anti-PD1 mAb (200 nM) with increasing amounts of anti-LAG3 antibodies. At the end of the second co-culture step supernatants were analysed for IFN-gamma secretion.

Using this assay, the combination of anti-PD1 and anti-LAG3 antibodies of the invention was compared to nivolumab (OPDIVO®) (PD1 mAb) plus an antibody having the same amino acid sequence as BMS-986016 (LAG3 mAb) in 4 different donors. Increasing amounts of anti-LAG3 antibodies were used in combination with a fixed dose of anti-PD1 mAbs. The data shown was normalized to an anti-PD1 antibody used at saturating concentration indicated as 100% and results are shown in FIG. 8.

This data demonstrates that a combination of anti-PD1 and anti-LAG3 antibodies of the invention leads to a 1.5-2 fold increase of IFN-gamma production when compared to anti-PD1 mAb alone. Surprisingly the combination of anti- PD1 and anti-LAG3 antibodies of the invention is superior than that of the prior art anti-PD1 and anti-LAG3 antibodies.

Furthermore the data shows that in 3 out of 4 donors anti-PD1-3 (a representative of the PD1 antibody of the invention) is superior to nivolumab (OPDIVO®) as seen in the higher levels of IFN-gamma secretion at very low anti-LAG3 mAB levels (FIG. 8).

As can be appreciated, this superiority of the combination of the anti-LAG3 antibody molecules of the present invention with anti-PD1 antibody molecules of the present invention suggests that they would be able to be used to treat cancer at a lower dosage level than the prior art antibody therapeutics, which may allow for a therapeutic application with less unwanted side effects.

Given that anti-PD1 and anti-LAG3 antibody molecules may induce unwanted side effects in patients, as discussed above, then the anti-PD1 antibodies and anti-LAG3 antibodies of the invention could have a significant and surprising clinical advantage over the art by using lower dosage and/or less frequent administration regimes.

Example 13: In Vivo Efficacy of Combination Therapy of Anti-PD1 and Anti-LAG3 Antibodies in Syngeneic Tumor Models To test whether the combination treatment of anti-PD1 and anti-LAG3 antibodies of the invention results in superior efficacy in vivo, several preclinical tumor mouse models were treated with anti-PD1 and anti-LAG3 mAbs. All mouse tumor cell lines (MC38, Colon-26 colon-, B16F10 melanoma, LL/2 (LLC1) Lewis Lung- and 4T1 breast-cancer) were injected subcutaneously in either C57BL/6 or BALB/c depending on the origin of mouse tumor cell line. On day 3 post cell injection mice were treated intraperitoneally (ip) followed by twice weekly dosing. All antibodies were dosed at 10 mg/kg and the combination of anti-LAG3 and anti-PD1 antibodies of the invention was dosed at 10 mg/kg each. Antibodies used in this study were all obtained from BioXCell, West Lebanon, N.H., USA. The control group was treated with a rat IgG2a antibody (clone 2A3), the anti-PD1 antibody used has a rat IgG2a Fc part (clone RMP1-14) and the anti-LAG3 used in the study was on a rat IgG1 Fc part (clone C9B7W). Tumor size was measured at least three times per week in two dimensions (length×width) and the tumor volumes were calculated. Animals were euthanized if the volume of the tumor reached 1500 mm³ or if tumors were ulcerated.

The results for the TGI and CR are summarized in Table 9 and FIGS. 9a to 9j are showing the tumor volume over time for individual mice. In conclusion the study shows that an anti-PD1 treatment alone shows efficacy in the MC38 but not in the other models tested. However, with the exception of the LL/2 model, the combination treatment of anti-PD1 and anti-LAG3 antibodies of the invention substantially improved the efficacy of anti-PD1 monotherapy and several mice were tumor free at the end of the study in the MC-38, Colon-26 and 4T1 model. Of particular note is that in the PD1 resistant 4T1 model the combination shows a superior effect on the tumor growth and 3 out of 5 mice were complete tumor free.

TABLE 9

Summary of the tumor growth inhibition of all syngeneic models tested

| | Cell line | | | | |
|---|---|---|---|---|---|
| | MC38 | B16-F10 | LL/2 (LLC1) | Colon-26 | 4T1 |
| Mouse strain | C57BL/6 | C57BL/6 | C57BL/6 | BALB/c | BALB/c |
| Day of TGI calculation | 19 | 22 | 22 | 24 | 31 |
| TGI [%] for PD1 | 81 | 38 | 0 | 42 | 5 |
| TGI [%] for LAG3 | 47 | Not tested | Not tested | Not tested | Not tested |
| TGI [%] for PD1 + LAG3 | 99 | 58 | 29 | 99 | 99 |
| CR for PD1 | 1 (10) | 0 (10) | 0 (10) | 1 (10) | 0 (10) |
| CR for LAG3 | 0 (10) | Not tested | Not tested | Not tested | Not tested |
| CR for PD-1 + LAG3 | 4 (10) | 0 (10) | 0 (10) | 3 (5) | 3 (5) |

Example 14: Pharmaceutical Formulation for S.C. Administration

Any of the above antibody molecules of the invention can be selected for the manufacture of a pharmaceutical formulation for subcutaneous application having a composition as follows:

Drug substance: 100 mg/ml (1 to 3 nmol/ml)

Acetate buffer: 25 mM

Trehalose: 220 mM

Tween-20: 0.02%

Drug substance is formulated in a solution having the above composition, sterilized and stored at 2 to 8° C.

Example 15: Pharmaceutical Formulation for I.v. Administration

Any of the above antibody molecules of the invention can be selected for the manufacture of a pharmaceutical formulation for i.v. application. An example of a suitable pharmaceutical formulation for the antibody of the invention is as follows.

A 20 mL vial contains 20 mg/mL of the anti-PD1 antibody of the invention, in a buffer consisting of 21.5 mM sodium acetate, 3.5 mM acetic acid, 240 mM trehalose, 0.67 mM L-methionine, 0.04% w/v polysorbate 20, and water for injection (WFI).

A 20 mL vial contains 20 mg/mL of the anti-LAG3 antibody of the invention in a buffer consisting of 25 mM acetate, 240 mM trehalose, 0.67 mM methionine, 0.04% (w/v) polysorbate 20, pH 5.5, and water for injection (WFI).

Example 16: Pharmaceutical Use in Humans

The solutions outlined in Example 15 above is applied to a patient in need thereof, such as a human being suffering from a cancer, by intravenous infusion (dosage of 100 to 200 mg) every two to four weeks.

Sequences

| SEQUENCE NUMBER | SEQUENCE NAME | SEQUENCE |
|---|---|---|
| 1 | PD1-1HCDR1 | GFTFSASAMS |
| 2 | PD1-1HCDR2 | YISGGGGDTYYSSSVKG |
| 3 | PD1-1HCDR3 | HSNVNYYAMDY |
| 4 | PD1-1LCDR1 | RASENIDTSGISFMN |
| 5 | PD1-1LCDR2 | VASNQGS |
| 6 | PD1-1LCDR3 | QQSKEVPWT |
| 7 | PD1-2HCDR1 | GFTFSASAMS |
| 8 | PD1-2HCDR2 | YISGGGGDTYYSSSVKG |
| 9 | PD1-2HCDR3 | HSNPNYYAMDY |
| 10 | PD1-2LCDR1 | RASENIDTSGISFMN |
| 11 | PD1-2LCDR2 | VASNQGS |
| 12 | PD1-2LCDR3 | QQSKEVPWT |
| 13 | PD1-3HCDR1 | GFTFSKSAMS |
| 14 | PD1-3HCDR2 | YISGGGGDTYYSSSVKG |
| 15 | PD1-3HCDR3 | HSNVNYYAMDY |
| 16 | PD1-3LCDR1 | RASENIDVSGISFMN |
| 17 | PD1-3LCDR2 | VASNQGS |
| 18 | PD1-3LCDR3 | QQSKEVPWT |
| 19 | PD1VH1 | EVMLVESGGGLVQPGGSLRLSCTASGFTFSASAMS WVRQAPGKGLEWVAYISGGGGDTYYSSSVKGRFTI SRDNAKNSLYLQMNSLRAEDTAVYYCARHSNVNYY AMDYWGQGTLVTVSS |
| 20 | PD1VL1 | EIVLTQSPATLSLSPGERATMSCRASENIDTSGIS FMNWYQQKPGQAPKLLIYVASNQGSGIPARFSGSG SGTDFTLTISRLEPEDFAVYYCQQSKEVPWTFGQG TKLEIK |
| 21 | PD1VH2 | EVMLVESGGGLVQPGGSLRLSCTASGFTFSASAMS WVRQAPGKGLEWVAYISGGGGDTYYSSSVKGRFTI SRDNAKNSLYLQMNSLRAEDTAVYYCARHSNPNYY AMDYWGQGTLVTVSS |
| 22 | PD1VL2 | EIVLTQSPATLSLSPGERATMSCRASENIDTSGIS FMNWYQQKPGQAPKLLIYVASNQGSGIPARFSGSG SGTDFTLTISRLEPEDFAVYYCQQSKEVPWTFGQG TKLEIK |
| 23 | PD1VH3 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSS |
| 24 | PD1VL3 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIK |
| 25 | PD1VH4 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSS |
| 26 | PD1VL4 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIK |

-continued

| SEQUENCE NUMBER | SEQUENCE NAME | SEQUENCE |
|---|---|---|
| 27 | PD1VH5 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSS |
| 28 | PD1VL5 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIK |
| 29 | PD1HC1 | EVMLVESGGGLVQPGGSLRLSCTASGFTFSASAMS WVRQAPGKGLEWVAYISGGGGDTYYSSSVKGRFTI SRDNAKNSLYLQMNSLRAEDTAVYYCARHSNVNYY AMDYWGQGTLVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLG |
| 30 | PD1LC1 | EIVLTQSPATLSLSPGERATMSCRASENIDTSGIS FMNWYQQKPGQAPKLLIYVASNQGSGIPARFSGSG SGTDFTLTISRLEPEDFAVYYCQQSKEVPWTFGQG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC |
| 31 | PD1HC2 | EVMLVESGGGLVQPGGSLRLSCTASGFTFSASAMS WVRQAPGKGLEWVAYISGGGGDTYYSSSVKGRFTI SRDNAKNSLYLQMNSLRAEDTAVYYCARHSNPNYY AMDYWGQGTLVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLG |
| 32 | PD1LC2 | EIVLTQSPATLSLSPGERATMSCRASENIDTSGIS FMNWYQQKPGQAPKLLIYVASNQGSGIPARFSGSG SGTDFTLTISRLEPEDFAVYYCQQSKEVPWTFGQG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC |
| 33 | PD1HC3 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLG |
| 34 | PD1LC3 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC |

-continued

| SEQUENCE NUMBER | SEQUENCE NAME | SEQUENCE |
|---|---|---|
| 35 | PD1HC4 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLG |
| 36 | PD1LC4 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC |
| 37 | PD1HC5 | EVMLVESGGGLVQPGGSLRLSCTASGFTFSKSAMS WVRQAPGKGLEWVAYISGGGGDTYYSSSVKGRFTI SRDNAKNSLYLQMNSLRAEDTAVYYCARHSNVNYY AMDYWGQGTLVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLG |
| 38 | PD1LC5 | EIVLTQSPATLSLSPGERATMSCRASENIDVSGIS FMNWYQQKPGQAPKLLIYVASNQGSGIPARFSGSG SGTDFTLTISRLEPEDFAVYYCQQSKEVPWTFGQG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC |
| 39 | LAG-1HCDR1 | GFSLSTSDMGVG |
| 40 | LAG-1HCDR2 | HIWWDDVKRYNPALKS |
| 41 | LAG-1HCDR3 | IEDYGVSYYFDY |
| 42 | LAG-1LCDR1 | KASQDVSTAVA |
| 43 | LAG-1LCDR2 | SASYRYT |
| 44 | LAG-1LCDR3 | QQHYSIPLT |
| 45 | LAG-2HCDR1 | GFSLSTSDMGVG |
| 46 | LAG-2HCDR2 | HIWWDDVKRYNPALKS |
| 47 | LAG-2HCDR3 | IVDYGVSYYFDY |
| 48 | LAG-2LCDR1 | KASQDVSTAVA |
| 49 | LAG-2LCDR2 | SASYRYT |
| 50 | LAG-2LCDR3 | QQHYSIPLT |
| 51 | LAGVH1 | QVTLVESGGGVVQPGRSLRLSCAFSGFSLSTSDMG VGWIRQAPGKGLEWVAHIWWDDVKRYNPALKSRFT ISRDNSKNTLYLQMNSLRAEDTAVYFCARIEDYGV SYYFDYWGQGTTVTVSS |

-continued

| SEQUENCE NUMBER | SEQUENCE NAME | SEQUENCE |
|---|---|---|
| 52 | LAGVL1 | DIQMTQSPSFLSASVGDRVSITCKASQDVSTAVAW YQQKPGKAPKLLIYSASYRYTGVPDRFSGSGSGTD FTLTISSLQPEDFATYYCQQHYSIPLTFGQGTKLE IK |
| 53 | LAGVH2 | QVTLKESGPTLVKPTQTLTLTCSFSGFSLSTSDMG VGWIRQPPGKALEWLAHIWWDDVKRYNPALKSRLT ITKDTSKNQVVLTMTNMDPVDTATYFCARIEDYGV SYYFDYWGQGTTVTVSS |
| 54 | LAGVL2 | DIQMTQSPSFLSASVGDRVTFTCKASQDVSTAVAW YQQKPGKAPKLLIYSASYRYTGVPDRFSGSGSGTD FTLTISSLQPEDFATYYCQQHYSIPLTFGQGTKLE IK |
| 55 | LAGVH3 | QVTLVESGGGVVQPGRSLSLSCAFSGFSLSTSDMG VGWVRQPPGKGLEWVAHIWWDDVKRYNPALKSRFT ISRDNSKNTLYLQMNSLRAEDTATYYCARIEDYGV SYYFDYWGQGTTVTVSS |
| 56 | LAGVL3 | DIQMTQSPSFLSASVGDRVTITCKASQDVSTAVAW YQQKPGKAPKLLIYSASYRYTGVPDRFSGSGSGTD FTLTISSLQPEDFATYYCQQHYSIPLTFGAGTKLE IK |
| 57 | LAGVH4 | QVTLVESGGGVVQPGRSLRLSCAFSGFSLSTSDMG VGWIRQAPGKGLEWVAHIWWDDVKRYNPALKSRFT ISRDNSKNTLYLQMNSLRAEDTATYFCARIEDYGV SYYFDYWGQGTTVTVSS |
| 58 | LAGVL4 | DIVMTQSPSFLSASVGDRVTITCKASQDVSTAVAW YQQKPGKAPKLLIYSASYRYTGVPDRFSGSGSGTD FTLTISSLQPEDFATYYCQQHYSIPLTFGQGTKLE IK |
| 59 | LAGVH5 | QVTLKESGPTLVKPTQTLTLTCSFSGFSLSTSDMG VGWIRQPPGKALEWLAHIWWDDVKRYNPALKSRLT ITKDTSKNQVVLTMTNMDPVDTATYFCARIVDYGV SYYFDYWGQGTTVTVSS |
| 60 | LAGVL5 | DIQMTQSPSFLSASVGDRVSITCKASQDVSTAVAW YQQKPGKAPKLLIYSASYRYTGVPDRFSGSGSGTD FTLTISSLQPEDFAVYYCQQHYSIPLTFGQGTKLE IK |
| 61 | LAGHC1 | QVTLVESGGGVVQPGRSLRLSCAFSGFSLSTSDMG VGWIRQAPGKGLEWVAHIWWDDVKRYNPALKSRFT ISRDNSKNTLYLQMNSLRAEDTAVYFCARIEDYGV SYYFDYWGQGTTVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLG |
| 62 | LAGLC1 | DIQMTQSPSFLSASVGDRVSITCKASQDVSTAVAW YQQKPGKAPKLLIYSASYRYTGVPDRFSGSGSGTD FTLTISSLQPEDFATYYCQQHYSIPLTFGQGTKLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| 63 | LAGHC2 | QVTLKESGPTLVKPTQTLTLTCSFSGFSLSTSDMG VGWIRQPPGKALEWLAHIWWDDVKRYNPALKSRLT ITKDTSKNQVVLTMTNMDPVDTATYFCARIEDYGV SYYFDYWGQGTTVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY |

| SEQUENCE NUMBER | SEQUENCE NAME | SEQUENCE |
|---|---|---|
| | | VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLG |
| 64 | LAGLC2 | DIQMTQSPSFLSASVGDRVTFTCKASQDVSTAVAW YQQKPGKAPKLLIYSASYRYTGVPDRFSGSGSGTD FTLTISSLQPEDFATYYCQQHYSIPLTFGQGTKLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| 65 | LAGHC3 | QVTLVESGGGVVQPGRSLSLSCAFSGFSLSTSDMG VGWVRQPPGKGLEWVAHIWWDDVKRYNPALKSRFT ISRDNSKNTLYLQMNSLRAEDTATYYCARIEDYGV SYYFDYWGQGTTVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLG |
| 66 | LAGLC3 | DIQMTQSPSFLSASVGDRVTITCKASQDVSTAVAW YQQKPGKAPKLLIYSASYRYTGVPDRFSGSGSGTD FTLTISSLQPEDFATYYCQQHYSIPLTFGAGTKLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| 67 | LAGHC4 | QVTLVESGGGVVQPGRSLRLSCAFSGFSLSTSDMG VGWIRQAPGKGLEWVAHIWWDDVKRYNPALKSRFT ISRDNSKNTLYLQMNSLRAEDTATYFCARIEDYGV SYYFDYWGQGTTVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLG |
| 68 | LAGLC4 | DIVMTQSPSFLSASVGDRVTITCKASQDVSTAVAW YQQKPGKAPKLLIYSASYRYTGVPDRFSGSGSGTD FTLTISSLQPEDFATYYCQQHYSIPLTFGQGTKLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| 69 | LAGHC5 | QVTLKESGPTLVKPTQTLTLTCSFSGFSLSTSDMG VGWIRQPPGKALEWLAHIWWDDVKRYNPALKSRLT ITKDTSKNQVVLTMTNMDPVDTATYFCARIVDYGV SYYFDYWGQGTTVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLG |
| 70 | LAGLC5 | DIQMTQSPSFLSASVGDRVSITCKASQDVSTAVAW YQQKPGKAPKLLIYSASYRYTGVPDRFSGSGSGTD FTLTISSLQPEDFAVYYCQQHYSIPLTFGQGTKLE IKRTVAAPSVFIFPPSDEQLKSGTASVVCLLNNFY |

-continued

| SEQUENCE NUMBER | SEQUENCE NAME | SEQUENCE |
|---|---|---|
| | | PREAKVQWKVDNALQSGNSQESVTEQDSKDSTYSL SSTLTLSKADYEKHKVYACEVTHQGLSSPVTKSFN RGEC |
| 71 | nPD1VH1 | GAGGTGATGCTGGTCGAGAGCGGCGGCGGTCTCGT GCAGCCAGGCGGTAGCCTGCGCCTCAGCTGCACCG CCAGCGGCTTCACCTTCAGCGCTAGCGCCATGAGC TGGGTGCGCCAAGCCCCAGGCAAGGGCCTGGAGTG GGTGGCCTACATCAGCGGCGGCGGCGGCGACACCT ACTACAGCTCCAGCGTGAAGGGCCGCTTCACCATC AGCCGCGACAACGCCAAAAACAGCCTGTACCTGCA AATGAACAGCCTGCGCGCCGAGGACACCGCCGTGT ACTACTGCGCCCGCCACAGCAACGTCAACTACTAC GCCATGGACTACTGGGGCCAGGGCACCCTGGTGAC CGTGAGCAGC |
| 72 | nPD1VL1 | GAGATCGTGCTGACCCAGAGCCCAGCCACCCTGAG CCTGAGCCCAGGCGAGCGCGCCACCATGAGCTGCC GCGCCAGCGAGAACATCGACACCAGCGGCATCAGC TTCATGAACTGGTACCAGCAGAAGCCAGGCCAGGC CCCAAAGCTGCTGATCTACGTGGCCAGCAACCAGG GCAGCGGCATCCCAGCCCGCTTCAGCGGCAGCGGC AGCGGCACCGACTTCACCCTGACCATCAGCCGCCT GGAGCCAGAGGACTTCGCCGTGTACTACTGCCAGC AGAGCAAGGAAGTCCCATGGACCTTCGGCCAAGGT ACTAAGCTGGAGATCAAG |
| 73 | nPD1VH2 | GAGGTGATGCTGGTCGAGAGCGGCGGCGGTCTCGT GCAGCCAGGCGGTAGCCTGCGCCTCAGCTGCACCG CCAGCGGCTTCACCTTCAGCGCTAGCGCCATGAGC TGGGTGCGCCAAGCCCCAGGCAAGGGCCTGGAGTG GGTGGCCTACATCAGCGGCGGCGGCGGCGACACCT ACTACAGCTCCAGCGTGAAGGGCCGCTTCACCATC AGCCGCGACAACGCCAAAAACAGCCTGTACCTGCA AATGAACAGCCTGCGCGCCGAGGACACCGCCGTGT ACTACTGCGCCCGCCACAGCAACCCAAACTACTAC GCCATGGACTACTGGGGCCAGGGCACCCTGGTGAC CGTGAGCAGC |
| 74 | nPD1VL2 | GAGATCGTGCTGACCCAGAGCCCAGCCACCCTGAG CCTGAGCCCAGGCGAGCGCGCCACCATGAGCTGCC GCGCCAGCGAGAACATCGACACCAGCGGCATCAGC TTCATGAACTGGTACCAGCAGAAGCCAGGCCAGGC CCCAAAGCTGCTGATCTACGTGGCCAGCAACCAGG GCAGCGGCATCCCAGCCCGCTTCAGCGGCAGCGGC AGCGGCACCGACTTCACCCTGACCATCAGCCGCCT GGAGCCAGAGGACTTCGCCGTGTACTACTGCCAGC AGAGCAAGGAAGTCCCATGGACCTTCGGCCAAGGT ACTAAGCTGGAGATCAAG |
| 75 | nPD1VH3 | GAGGTGATGCTGGTCGAGAGCGGCGGCGGTCTCGT GCAGCCAGGCGGTAGCCTGCGCCTCAGCTGCACCG CCAGCGGCTTCACCTTCAGCAAGAGCGCCATGAGC TGGGTGCGCCAAGCCCCAGGCAAGGGCCTGGAGTG GGTGGCCTACATCAGCGGCGGCGGCGGCGACACCT ACTACAGCTCCAGCGTGAAGGGCCGCTTCACCATC AGCCGCGACAACGCCAAGAACAGCCTGTACCTGCA AATGAACAGCCTGCGCGCCGAGGACACCGCCGTGT ACTACTGCGCCCGCCACAGCAACGTCAACTACTAC GCCATGGACTACTGGGGCCAGGGCACCCTGGTGAC CGTGAGCAGC |
| 76 | nPD1VL3 | GAGATCGTGCTGACCCAGAGCCCAGCCACCCTAAG CCTGAGCCCAGGCGAGCGCGCCACCATGAGCTGCC GCGCCAGCGAGAACATCGACCACAGCGGCATCAGC TTCATGAACTGGTACCAGCAGAAGCCAGGCCAGGC CCCAAAGCTGCTGATCTACGTGGCCAGCAACCAGG GCAGCGGCATCCCAGCCCGCTTCAGCGGCAGCGGC AGCGGCACCGACTTCACCCTGACCATCAGCCGCCT GGAGCCAGAGGACTTCGCCGTGTACTACTGCCAGC AGAGCAAGGAAGTCCCATGGACCTTCGGCCAAGGT ACTAAGCTGGAGATCAAG |
| 77 | nPD1VH4 | GAGGTGATGCTGGTCGAGAGCGGCGGCGGTCTCGT GCAGCCAGGCGGTAGCCTGCGCCTCAGCTGCACCG CCAGCGGCTTCACCTTCAGCAAGAGCGCCATGAGC |

| SEQUENCE NUMBER | SEQUENCE NAME | SEQUENCE |
|---|---|---|
| | | TGGGTGCGCCAAGCCCCAGGCAAGGGCCTGGAGTG<br>GGTGGCCTACATCAGCGGCGGCGGCGGCGACACCT<br>ACTACAGCTCCAGCGTGAAGGGCCGCTTCACCATC<br>AGCCGCGACAACGCCAAGAACAGCCTGTACCTGCA<br>AATGAACAGCCTGCGCGCCGAGGACACCGCCGTGT<br>ACTACTGCGCCCGCCACAGCAACGTCAACTACTAC<br>GCCATGGACTACTGGGGCCAGGGCACCCTGGTGAC<br>CGTGAGCAGC |
| 78 | nPD1VL4 | GAGATCGTGCTGACCCAGAGCCCAGCCACCCTAAG<br>CCTGAGCCCAGGCGAGCGCGCCACCATGAGCTGCC<br>GCGCCAGCGAGAACATCGACCACAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT<br>ACTAAGCTGGAGATCAAG |
| 79 | nPD1VH5 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCAAGAGCGCCATGAGC<br>TGGGTGCGCCAAGCCCCAGGCAAGGGCCTGGAGTG<br>GGTGGCCTACATCAGCGGCGGCGGCGGCGACACCT<br>ACTACAGCTCCAGCGTGAAGGGCCGCTTCACCATC<br>AGCCGCGACAACGCCAAGAACAGCCTGTACCTGCA<br>AATGAACAGCCTGCGCGCCGAGGACACCGCCGTGT<br>ACTACTGCGCCCGCCACAGCAACGTCAACTACTAC<br>GCCATGGACTACTGGGGCCAGGGCACCCTGGTGAC<br>CGTGAGCAGC |
| 80 | nPD1VL5 | GAGATCGTGCTGACCCAGAGCCCAGCCACCCTGAG<br>CCTGAGCCCAGGCGAGCGCGCCACCATGAGCTGCC<br>GCGCCAGCGAGAACATCGACGTAAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT<br>ACTAAGCTGGAAATCAAG |
| 81 | nPD1HC1 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCGCTAGCGCCATGAGC<br>TGGGTGCGCCAAGCCCCAGGCAAGGGCCTGGAGTG<br>GGTGGCCTACATCAGCGGCGGCGGCGGCGACACCT<br>ACTACAGCTCCAGCGTGAAGGGCCGCTTCACCATC<br>AGCCGCGACAACGCCAAAAACAGCCTGTACCTGCA<br>AATGAACAGCCTGCGCGCCGAGGACACCGCCGTGT<br>ACTACTGCGCCCGCCACAGCAACGTCAACTACTAC<br>GCCATGGACTACTGGGGCCAGGGCACCCTGGTGAC<br>CGTGAGCAGCGCCTCCACAAAGGGCCCTTCCGTGT<br>TCCCCCTGGCCCCTTGCTCCCGGTCCACCTCCGAG<br>TCTACCGCCGCTCTGGGCTGCCTGGTCAAGGACTA<br>CTTCCCCGAGCCCGTGACCGTGTCCTGGAACTCTG<br>GCGCCCTGACCTCCGGCGTGCACACCTTCCCTGCT<br>GTGCTGCAGTCCTCCGGCCTGTACTCCCTGTCCTC<br>CGTCGTGACCGTGCCCTCCTCTAGCCTGGGCACCA<br>AGACCTACACCTGTAACGTGGACCACAAGCCCTCC<br>AACACCAAGGTGGACAAGCGGGTGGAATCTAAGTA<br>CGGCCCTCCCTGCCCCCCCTGCCCTGCCCCTGAAT<br>TTCTGGGCGGACCCTCCGTGTTCCTGTTCCCCCCA<br>AAGCCCAAGGACACCCTGATGATCTCCCGGACCCC<br>CGAAGTGACCTGCGTGGTGGTGGACGTGTCCCAGG<br>AAGATCCCGAGGTCCAGTTTAATTGGTACGTGGAC<br>GGCGTGGAAGTGCACAACGCCAAGACCAAGCCCAG<br>AGAGGAACAGTTCAACTCCACCTACCGGGTGGTGT<br>CCGTGCTGACCGTGCTGCACCAGGACTGGCTGAAC<br>GGCAAAGAGTACAAGTGCAAGGTGTCCAACAAGGG<br>CCTGCCCTCCAGCATCGAAAAGACCATCTCCAAGG<br>CCAAGGGCCAGCCCCGCGAGCCCCAGGTGTACACC<br>CTGCCTCCAAGCCAGGAAGAGATGACCAAGAACCA<br>GGTGTCCCTGACCTGTCTGGTCAAGGGCTTCTACC<br>CCTCCGATATCGCCGTGGAATGGGAGTCCAACGGC |

| SEQUENCE NUMBER | SEQUENCE NAME | SEQUENCE |
|---|---|---|
| | | CAGCCCGAGAACAACTACAAGACCACCCCCCCTGT<br>GCTGGACTCCGACGGCTCCTTCTTCCTGTACTCTC<br>GGCTGACCGTGGACAAGTCCCGGTGGCAGGAAGGC<br>AACGTCTTCTCCTGCTCCGTGATGCACGAGGCCCT<br>GCACAACCACTACACCCAGAAGTCCCTGTCCCTGA<br>GCCTGGGC |
| 82 | nPD1LC1 | GAGATCGTGCTGACCCAGAGCCCAGCCACCCTGAG<br>CCTGAGCCCAGGCGAGCGCGCCACCATGAGCTGCC<br>GCGCCAGCGAGAACATCGACACCAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT<br>ACTAAGCTGGAGATCAAGCGTACTGTGGCTGCACC<br>ATCTGTCTTCATCTTCCCGCCATCTGATGAGCAAT<br>TGAAATCTGGAACTGCCTCTGTTGTGTGCCTGCTG<br>AATAACTTCTATCCCAGAGAGGCCAAAGTACAGTG<br>GAAGGTGGATAACGCCCTCCAATCGGGTAACTCCC<br>AGGAGAGTGTCACAGAGCAGGACAGCAAGGACAGC<br>ACCTACAGCCTCAGCAGCACCCTGACGCTGAGCAA<br>AGCAGACTACGAGAAACACAAAGTCTACGCCTGCG<br>AAGTCACCCATCAGGGCCTGAGCTCGCCCGTCACA<br>AAGAGCTTCAACAGGGGAGAGTGT |
| 83 | nPD1HC2 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCGCTAGCGCCATGAGC<br>TGGGTGCGCCAAGCCCCAGGCAAGGGCCTGGAGTG<br>GGTGGCCTACATCAGCGGCGGCGGCGGCGACACCT<br>ACTACAGCTCCAGCGTGAAGGGCCGCTTCACCATC<br>AGCCGCGACAACGCCAAAAACAGCCTGTACCTGCA<br>AATGAACAGCCTGCGCGCCGAGGACACCGCCGTGT<br>ACTACTGCGCCCGCCACAGCAACCCAAACTACTAC<br>GCCATGGACTACTGGGGCCAGGGCACCCTGGTGAC<br>CGTGAGCAGCGCCTCCACAAAGGGCCCTTCCGTGT<br>TCCCCCTGGCCCCTTGCTCCCGGTCCACCTCCGAG<br>TCTACCGCCGCTCTGGGCTGCCTGGTCAAGGACTA<br>CTTCCCCGAGCCCGTGACCGTGTCCTGGAACTCTG<br>GCGCCCTGACCTCCGGCGTGCACACCTTCCCTGCT<br>GTGCTGCAGTCCTCCGGCCTGTACTCCCTGTCCTC<br>CGTCGTGACCGTGCCCTCCTCTAGCCTGGGCACCA<br>AGACCTACACCTGTAACGTGGACCACAAGCCCTCC<br>AACACCAAGGTGGACAAGCGGGTGGAATCTAAGTA<br>CGGCCCTCCCTGCCCCCCCTGCCCTGCCCCTGAAT<br>TTCTGGGCGGACCCTCCGTGTTCCTGTTCCCCCCA<br>AAGCCCAAGGACACCCTGATGATCTCCCGGACCCC<br>CGAAGTGACCTGCGTGGTGGTGGACGTGTCCCAGG<br>AAGATCCCGAGGTCCAGTTTAATTGGTACGTGGAC<br>GGCGTGGAAGTGCACAACGCCAAGACCAAGCCCAG<br>AGAGGAACAGTTCAACTCCACCTACCGGGTGGTGT<br>CCGTGCTGACCGTGCTGCACCAGGACTGGCTGAAC<br>GGCAAAGAGTACAAGTGCAAGGTGTCCAACAAGGG<br>CCTGCCCTCCAGCATCGAAAAGACCATCTCCAAGG<br>CCAAGGGCCAGCCCCGCGAGCCCCAGGTGTACACC<br>CTGCCTCCAAGCCAGGAAGAGATGACCAAGAACCA<br>GGTGTCCCTGACCTGTCTGGTCAAGGGCTTCTACC<br>CCTCCGATATCGCCGTGGAATGGGAGTCCAACGGC<br>CAGCCCGAGAACAACTACAAGACCACCCCCCCTGT<br>GCTGGACTCCGACGGCTCCTTCTTCCTGTACTCTC<br>GGCTGACCGTGGACAAGTCCCGGTGGCAGGAAGGC<br>AACGTCTTCTCCTGCTCCGTGATGCACGAGGCCCT<br>GCACAACCACTACACCCAGAAGTCCCTGTCCCTGA<br>GCCTGGGC |
| 84 | nPD1LC2 | GAGATCGTGCTGACCCAGAGCCCAGCCACCCTGAG<br>CCTGAGCCCAGGCGAGCGCGCCACCATGAGCTGCC<br>GCGCCAGCGAGAACATCGACACCAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT |

-continued

| SEQUENCE NUMBER | SEQUENCE NAME | SEQUENCE |
|---|---|---|
| | | ACTAAGCTGGAGATCAAGCGTACTGTGGCTGCACC<br>ATCTGTCTTCATCTTCCCGCCATCTGATGAGCAAT<br>TGAAATCTGGAACTGCCTCTGTTGTGTGCCTGCTG<br>AATAACTTCTATCCCAGAGAGGCCAAAGTACAGTG<br>GAAGGTGGATAACGCCCTCCAATCGGGTAACTCCC<br>AGGAGAGTGTCACAGAGCAGGACAGCAAGGACAGC<br>ACCTACAGCCTCAGCAGCACCCTGACGCTGAGCAA<br>AGCAGACTACGAGAAACACAAAGTCTACGCCTGCG<br>AAGTCACCCATCAGGGCCTGAGCTCGCCCGTCACA<br>AAGAGCTTCAACAGGGGAGAGTGT |
| 85 | nPD1HC3 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCAAGAGCGCCATGAGC<br>TGGGTGCGCCAAGCCCCAGGCAAGGGCCTGGAGTG<br>GGTGGCCTACATCAGCGGCGGCGGCGGCGACACCT<br>ACTACAGCTCCAGCGTGAAGGGCCGCTTCACCATC<br>AGCCGCGACAACGCCAAGAACAGCCTGTACCTGCA<br>AATGAACAGCCTGCGCGCCGAGGACACCGCCGTGT<br>ACTACTGCGCCCGCCACAGCAACGTCAACTACTAC<br>GCCATGGACTACTGGGGCCAGGGCACCCTGGTGAC<br>CGTGAGCAGCGCCTCCACAAAGGGCCCTTCCGTGT<br>TCCCCCTGGCCCCTTGCTCCCGGTCCACCTCCGAG<br>TCTACCGCCGCTCTGGGCTGCCTGGTCAAGGACTA<br>CTTCCCCGAGCCCGTGACCGTGTCCTGGAACTCTG<br>GCGCCCTGACCTCCGGCGTGCACACCTTCCCTGCT<br>GTGCTGCAGTCCTCCGGCCTGTACTCCCTGTCCTC<br>CGTCGTGACCGTGCCCTCCTCTAGCCTGGGCACCA<br>AGACCTACACCTGTAACGTGGACCACAAGCCCTCC<br>AACACCAAGGTGGACAAGCGGGTGGAATCTAAGTA<br>CGGCCCTCCCTGCCCCCCCTGCCCTGCCCCTGAAT<br>TTCTGGGCGGACCCTCCGTGTTCCTGTTCCCCCCA<br>AAGCCCAAGGACACCCTGATGATCTCCCGGACCCC<br>CGAAGTGACCTGCGTGGTGGTGGACGTGTCCCAGG<br>AAGATCCCGAGGTCCAGTTTAATTGGTACGTGGAC<br>GGCGTGGAAGTGCACAACGCCAAGACCAAGCCCAG<br>AGAGGAACAGTTCAACTCCACCTACCGGGTGGTGT<br>CCGTGCTGACCGTGCTGCACCAGGACTGGCTGAAC<br>GGCAAAGAGTACAAGTGCAAGGTGTCCAACAAGGG<br>CCTGCCCTCCAGCATCGAAAAGACCATCTCCAAGG<br>CCAAGGGCCAGCCCCGCGAGCCCCAGGTGTACACC<br>CTGCCTCCAAGCCAGGAAGAGATGACCAAGAACCA<br>GGTGTCCCTGACCTGTCTGGTCAAGGGCTTCTACC<br>CCTCCGATATCGCCGTGGAATGGGAGTCCAACGGC<br>CAGCCCGAGAACAACTACAAGACCACCCCCCCTGT<br>GCTGGACTCCGACGGCTCCTTCTTCCTGTACTCTC<br>GGCTGACCGTGGACAAGTCCCGGTGGCAGGAAGGC<br>AACGTCTTCTCCTGCTCCGTGATGCACGAGGCCCT<br>GCACAACCACTACACCCAGAAGTCCCTGTCCCTGA<br>GCCTGGGC |
| 86 | nPD1LC3 | GAGATCGTGCTGACCCAGAGCCCAGCCACCCTGAG<br>CCTGAGCCCAGGCGAGCGCGCCACCATGAGCTGCC<br>GCGCCAGCGAGAACATCGACGTAAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT<br>ACTAAGCTGGAAATCAAGCGTACTGTGGCTGCACC<br>ATCTGTCTTCATCTTCCCGCCATCTGATGAGCAAT<br>TGAAATCTGGAACTGCCTCTGTTGTGTGCCTGCTG<br>AATAACTTCTATCCCAGAGAGGCCAAAGTACAGTG<br>GAAGGTGGATAACGCCCTCCAATCGGGTAACTCCC<br>AGGAGAGTGTCACAGAGCAGGACAGCAAGGACAGC<br>ACCTACAGCCTCAGCAGCACCCTGACGCTGAGCAA<br>AGCAGACTACGAGAAACACAAAGTCTACGCCTGCG<br>AAGTCACCCATCAGGGCCTGAGCTCGCCCGTCACA<br>AAGAGCTTCAACAGGGGAGAGTGT |
| 87 | nPD1HC4 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCCGCAGCGCCATGAGC<br>TGGGTGCGCCAAGCCCCAGGCAAGGGCCTGGAGTG<br>GGTGGCCTACATCAGCGGCGGCGGCGGCGACACCT |

| SEQUENCE NUMBER | SEQUENCE NAME | SEQUENCE |
|---|---|---|
| | | ACTACAGCGTCAGCGTGAAGGGCCGCTTCACCATC<br>AGCCGCGACAACGCCAAGAACAGCCTGTACCTGCA<br>AATGAACAGCCTGCGCGCCGAGGACACCGCCGTGT<br>ACTACTGCGCCCGCCACAGCAACTACAACTACTAC<br>GCCATGGACTACTGGGGCCAGGGCACCCTGGTGAC<br>CGTGAGCAGCGCCTCCACCAAGGGCCCATCGGTCT<br>TCCCGCTAGCACCCTCCTCCAAGAGCACCTCTGGG<br>GGCACAGCGGCCCTGGGCTGCCTGGTCAAGGACTA<br>CTTCCCCGAACCGGTGACGGTGTCGTGGAACTCAG<br>GCGCCCTGACCAGCGGCGTGCACACCTTCCCGGCT<br>GTCCTACAGTCCTCAGGACTCTACTCCCTCAGCAG<br>CGTGGTGACCGTGCCCTCCAGCAGCTTGGGCACCC<br>AGACCTACATCTGCAACGTGAATCACAAGCCCAGC<br>AACACCAAGGTGGACAAGCGCGTTGAGCCCAAATC<br>TTGTGACAAAACTCACACATGCCCACCGTGCCCAG<br>CACCTGAAGCCGCTGGGGGACCGTCAGTCTTCCTC<br>TTCCCCCCAAAACCCAAGGACACCCTCATGATCTC<br>CCGGACCCCTGAGGTCACATGCGTGGTGGTGGACG<br>TGAGCCACGAAGACCCTGAGGTCAAGTTCAACTGG<br>TACGTGGACGGCGTGGAGGTGCATAATGCCAAGAC<br>AAAGCCGCGGGAGGAGCAGTACAACAGCACGTACC<br>GTGTGGTCAGCGTCCTCACCGTCCTGCACCAGGAC<br>TGGCTGAATGGCAAGGAGTACAAGTGCAAGGTCTC<br>CAACAAAGCCCTCCCAGCCCCCATCGAGAAAACCA<br>TCTCCAAAGCCAAAGGGCAGCCCCGAGAACCACAG<br>GTGTACACCCTGCCCCCATCCCGCGAGGAGATGAC<br>CAAGAACCAGGTAAGTTTGACCTGCCTGGTCAAAG<br>GCTTCTATCCCAGCGACATCGCCGTGGAGTGGGAG<br>AGCAATGGGCAGCCGGAGAACAACTACAAGACCAC<br>GCCTCCCGTGCTGGACTCCGACGGCTCCTTCTTCC<br>TCTATAGCAAGCTCACCGTGGACAAGAGCAGGTGG<br>CAGCAGGGGAACGTCTTCTCATGCTCCGTGATGCA<br>TGAGGCTCTGCACAACCACTACACGCAGAAGAGCC<br>TCTCCCTGTCTCCGGGT |
| 88 | nPD1LC4 | GAGATCGTGCTGACCCAGAGCCCAGCCACCCTAAG<br>CCTGAGCCCAGGCGAGCGCGCCACCATGAGCTGCC<br>GCGCCAGCGAGAACATCGACCACAGCGGCATCAGC<br>TTCATGAACTGGTACCAGCAGAAGCCAGGCCAGGC<br>CCCAAAGCTGCTGATCTACGTGGCCAGCAACCAGG<br>GCAGCGGCATCCCAGCCCGCTTCAGCGGCAGCGGC<br>AGCGGCACCGACTTCACCCTGACCATCAGCCGCCT<br>GGAGCCAGAGGACTTCGCCGTGTACTACTGCCAGC<br>AGAGCAAGGAAGTCCCATGGACCTTCGGCCAAGGT<br>ACTAAGCTGGAGATCAAGCGTACTGTGGCTGCACC<br>ATCTGTCTTCATCTTCCCGCCATCTGATGAGCAAT<br>TGAAATCTGGAACTGCCTCTGTTGTGTGCCTGCTG<br>AATAACTTCTATCCCAGAGAGGCCAAAGTACAGTG<br>GAAGGTGGATAACGCCCTCCAATCGGGTAACTCCC<br>AGGAGAGTGTCACAGAGCAGGACAGCAAGGACAGC<br>ACCTACAGCCTCAGCAGCACCCTGACGCTGAGCAA<br>AGCAGACTACGAGAAACACAAAGTCTACGCCTGCG<br>AAGTCACCCATCAGGGCCTGAGCTCGCCCGTCACA<br>AAGAGCTTCAACAGGGGAGAGTGT |
| 89 | nPD1HC5 | GAGGTGATGCTGGTCGAGAGCGGCGGCGGTCTCGT<br>GCAGCCAGGCGGTAGCCTGCGCCTCAGCTGCACCG<br>CCAGCGGCTTCACCTTCAGCCGCAGCGCCATGAGC<br>TGGGTGCGCCAAGCCCCAGGCAAGGGCCTGGAGTG<br>GGTGGCCTACATCAGCGGCGGCGGCGGCGACACCT<br>ACTACAGCGTCAGCGTGAAGGGCCGCTTCACCATC<br>AGCCGCGACAACGCCAAGAACAGCCTGTACCTGCA<br>AATGAACAGCCTGCGCGCCGAGGACACCGCCGTGT<br>ACTACTGCGCCCGCCACAGCAACTACAACTACTAC<br>GCCATGGACTACTGGGGCCAGGGCACCCTGGTGAC<br>CGTGAGCAGCGCCTCCACAAAGGGCCCTTCCGTGT<br>TCCCCCTGGCCCCTTGCTCCCGGTCCACCTCCGAG<br>TCTACCGCCGCTCTGGGCTGCCTGGTCAAGGACTA<br>CTTCCCCGAGCCCGTGACCGTGTCCTGGAACTCTG<br>GCGCCCTGACCTCCGGCGTGCACACCTTCCCTGCT<br>GTGCTGCAGTCCTCCGGCCTGTACTCCCTGTCCTC<br>CGTCGTGACCGTGCCCTCCTCAGCCTGGGCACCA<br>AGACCTACACCTGTAACGTGGACCACAAGCCCTCC<br>AACACCAAGGTGGACAAGCGGGTGGAATCTAAGTA<br>CGGCCCTCCCTGCCCCCCCTGCCCTGCCCCTGAAT<br>TTCTGGGCGGACCCTCCGTGTTCCTGTTCCCCCCA |

| SEQUENCE NUMBER | SEQUENCE NAME | SEQUENCE |
|---|---|---|
| | | AAGCCCAAGGACACCCTGATGATCTCCCGGACCCC CGAAGTGACCTGCGTGGTGGTGGACGTGTCCCAGG AAGATCCCGAGGTCCAGTTTAATTGGTACGTGGAC GGCGTGGAAGTGCACAACGCCAAGACCAAGCCCAG AGAGGAACAGTTCAACTCCACCTACCGGGTGGTGT CCGTGCTGACCGTGCTGCACCAGGACTGGCTGAAC GGCAAAGAGTACAAGTGCAAGGTGTCCAACAAGGG CCTGCCCTCCAGCATCGAAAAGACCATCTCCAAGG CCAAGGGCCAGCCCCGCGAGCCCCAGGTGTACACC CTGCCTCCAAGCCAGGAAGAGATGACCAAGAACCA GGTGTCCCTGACCTGTCTGGTCAAGGGCTTCTACC CCTCCGATATCGCCGTGGAATGGGAGTCCAACGGC CAGCCCGAGAACAACTACAAGACCACCCCCCCTGT GCTGGACTCCGACGGCTCCTTCTTCCTGTACTCTC GGCTGACCGTGGACAAGTCCCGGTGGCAGGAAGGC AACGTCTTCTCCTGCTCCGTGATGCACGAGGCCCT GCACAACCACTACACCCAGAAGTCCCTGTCCCTGA GCCTGGGC |
| 90 | nPD1LC5 | GAGATCGTGCTGACCCAGAGCCCAGCCACCCTAAG CCTGAGCCCAGGCGAGCGCGCCACCATGAGCTGCC GCGCCAGCGAGAACATCGACCACAGCGGCATCAGC TTCATGAACTGGTACCAGCAGAAGCCAGGCCAGGC CCCAAAGCTGCTGATCTACGTGGCCAGCAACCAGG GCAGCGGCATCCCAGCCCGCTTCAGCGGCAGCGGC AGCGGCACCGACTTCACCCTGACCATCAGCCGCCT GGAGCCAGAGGACTTCGCCGTGTACTACTGCCAGC AGAGCAAGGAAGTCCCATGGACCTTCGGCCAAGGT ACTAAGCTGGAGATCAAGCGTACTGTGGCTGCACC ATCTGTCTTCATCTTCCCGCCATCTGATGAGCAAT TGAAATCTGGAACTGCCTCTGTTGTGTGCCTGCTG AATAACTTCTATCCCAGAGAGGCCAAAGTACAGTG GAAGGTGGATAACGCCCTCCAATCGGGTAACTCCC AGGAGAGTGTCACAGAGCAGGACAGCAAGGACAGC ACCTACAGCCTCAGCAGCACCCTGACGCTGAGCAA AGCAGACTACGAGAAACACAAAGTCTACGCCTGCG AAGTCACCCATCAGGGCCTGAGCTCGCCCGTCACA AAGAGCTTCAACAGGGGAGAGTGT |
| 91 | nLAGVH1 | CAGGTCACCCTGAAGGAGAGCGGCCCAACCCTGGT GAAGCCAACCCAGACCCTGACCCTGACCTGCAGCT TCAGCGGCTTCTCCCTGAGCACCAGCGACATGGGC GTGGGCTGGATTCGCCAACCACCAGGCAAGGCCCT GGAGTGGCTGGCCCACATCTGGTGGGACGACGTGA AGCGCTACAACCCAGCCCTGAAGAGCCGCCTGACC ATCACCAAGGACACCAGCAAGAACCAGGTGGTGCT GACCATGACC |
| 92 | nLAGVL1 | GACATCCAGATGACCCAGAGCCCTAGCTTCCTGAG CGCCAGCGTCGGCGACCGCGTGACCTTCACCTGCA AGGCCAGCCAGGACGTGAGCACCGCCGTCGCCTGG TATCAGCAGAAGCCTGGCAAGGCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCACC |
| 93 | nLAGVH2 | CAGGTGACCCTGGTGGAGAGCGGCGGCGGCGTCGT GCAGCCAGGCCGCAGCCTGAGCCTGAGCTGCGCTT TCAGCGGCTTCAGCCTCAGCACCAGCGACATGGGC GTGGGCTGGGTCCGCCAACCACCAGGCAAGGGCCT GGAGTGGGTGGCCCACATCTGGTGGGACGACGTGA AGCGCTACAACCCAGCCCTGAAGAGCCGCTTTACC ATCAGCCGCGACAACAGCAAGAACACCCTGTACCT GCAAATGAAC |
| 94 | nLAGVL2 | ACATCCAGATGACCCAGAGCCCTAGCTTCCTGAGC GCCAGCGTCGGCGACCGCGTGACGATCACCTGCAA GGCCAGCCAGGACGTGAGCACCGCCGTCGCCTGGT ATCAGCAGAAGCCTGGCAAGGCCCCAAAGCTGCTG ATCTACAGCGCCAGCTACCGCTACACCGGCGTGCC AGACCGCTTCAGCGGCAGCGGCAGCGGCACCGACT TCACCCTGACCATCAGCAGCCTGCAACCAGAGGAC TTCGCCACC |

| SEQUENCE NUMBER | SEQUENCE NAME | SEQUENCE |
|---|---|---|
| 95 | nLAGVH3 | CAGGTGACCCTGGTGGAGAGCGGCGGCGGCGTCGT GCAGCCAGGCCGCAGCCTGCGCCTGAGCTGCGCTT TCAGCGGCTTCAGCCTCAGCACCAGCGACATGGGC GTGGGCTGGATCCGCCAAGCCCAGGCAAGGGCCT GGAGTGGGTGGCCCACATCTGGTGGGACGACGTGA AGCGCTACAACCCAGCCCTGAAGAGCCGCTTTACC ATCAGCCGCGACAACAGCAAGAACACCCTGTACCT GCAAATGAAC |
| 96 | nLAGVL3 | GACATCGTGATGACCCAGAGCCCTAGCTTCCTGAG CGCCAGCGTCGGCGACCGCGTGACCATCACCTGCA AGGCCAGCCAGGACGTGAGCACCGCCGTCGCCTGG TATCAGCAGAAGCCTGGCAAGGCCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCACC |
| 97 | nLAGVH4 | CAGGTGACCCTGGTGGAGAGCGGCGGCGGCGTCGT GCAGCCAGGCCGCAGCCTGCGCCTGAGCTGCGCTT TCAGCGGCTTCAGCCTCAGCACCAGCGACATGGGC GTGGGCTGGATCCGCCAAGCCCAGGCAAGGGCCT GGAGTGGGTGGCCCACATCTGGTGGGACGACGTGA AGCGCTACAACCCAGCCCTGAAGAGCCGCTTTACC ATCAGCCGCGACAACAGCAAGAACACCCTGTACCT GCAAATGAAC |
| 98 | nLAGVL4 | GACATCCAGATGACCCAGAGCCCTAGCTTCCTGAG CGCCAGCGTCGGCGACCGCGTGAGCATCACCTGCA AGGCCAGCCAGGACGTGAGCACCGCCGTCGCCTGG TATCAGCAGAAGCCTGGCAAGGCCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCACC |
| 99 | nLAGVH5 | CAGGTCACCCTGAAGGAGAGCGGCCCAACCCTGGT GAAGCCAACCCAGACCCTGACCCTGACCTGCAGCT TCAGCGGCTTCTCCCTGAGCACCAGCGACATGGGC GTGGGCTGGATTCGCCAACCACCAGGCAAGGCCCT GGAGTGGCTGGCCCACATCTGGTGGGACGACGTGA AGCGCTACAACCCAGCCCTGAAGAGCCGCCTGACC ATCACCAAGGACACCAGCAAGAACCAGGTGGTGCT GACCATGACC |
| 100 | nLAGVL5 | GACATCCAGATGACCCAGAGCCCTAGCTTCCTGAG CGCCAGCGTCGGCGACCGCGTGAGCATCACCTGCA AGGCCAGCCAGGACGTGAGCACCGCCGTCGCCTGG TATCAGCAGAAGCCTGGCAAGGCCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCGTG |
| 101 | nLAGHC1 | CAGGTCACCCTGAAGGAGAGCGGCCCAACCCTGGT GAAGCCAACCCAGACCCTGACCCTGACCTGCAGCT TCAGCGGCTTCTCCCTGAGCACCAGCGACATGGGC GTGGGCTGGATTCGCCAACCACCAGGCAAGGCCCT GGAGTGGCTGGCCCACATCTGGTGGGACGACGTGA AGCGCTACAACCCAGCCCTGAAGAGCCGCCTGACC ATCACCAAGGACACCAGCAAGAACCAGGTGGTGCT GACCATGACCAACATGGACCCAGTGGACACCGCCA CCTACTTCTGCGCCCGCATCGAGGACTACGGCGTG AGCTACTACTTCGACTACTGGGGCCAGGGCACCAC CGTGACCGTGAGCAGCGCCTCCACAAAGGGCCCTT CCGTGTTCCCCCTGGCCCCTTGCTCCCGGTCCACC TCCGAGTCTACCGCCGCTCTGGGCTGCCTGGTCAA GGACTACTTCCCCGAGCCCGTGACCGTGTCCTGGA ACTCTGGCGCCCTGACCTCCGGCGTGCACACCTTC CCTGCTGTGCTGCAGTCCTCCGGCCTGTACTCCCT GTCCTCCGTCGTGACCGTGCCCTCCTCTAGCCTGG GCACCAAGACCTACACCTGTAACGTGGACCACAAG CCCTCCAACACCAAGGTGGACAAGGGGTGGAATC TAAGTACGGCCCTCCCTGCCCCCCCTGCCCTGCCC CTGAATTTCTGGGCGGACCCTCCGTGTTCCTGTTC |

| SEQUENCE NUMBER | SEQUENCE NAME | SEQUENCE |
|---|---|---|
| | | CCCCCAAAGCCCAAGGACACCCTGATGATCTCCCG<br>GACCCCCGAAGTGACCTGCGTGGTGGTGGACGTGT<br>CCCAGGAAGATCCCGAGGTCCAGTTTAATTGGTAC<br>GTGGACGGCGTGGAAGTGCACAACGCCAAGACCAA<br>GCCCAGAGAGGAACAGTTCAACTCCACCTACCGGG<br>TGGTGTCCGTGCTGACCGTGCTGCACCAGGACTGG<br>CTGAACGGCAAAGAGTACAAGTGCAAGGTGTCCAA<br>CAAGGGCCTGCCCTCCAGCATCGAAAAGACCATCT<br>CCAAGGCCAAGGGCCAGCCCCGCGAGCCCCAGGTG<br>TACACCCTGCCTCCAAGCCAGGAAGAGATGACCAA<br>GAACCAGGTGTCCCTGACCTGTCTGGTCAAGGGCT<br>TCTACCCCTCCGATATCGCCGTGGAATGGGAGTCC<br>AACCGGCAGCCCGAGAACAACTACAAGACCACCCC<br>CCCTGTGCTGGACTCCGACGGCTCCTTCTTCCTGT<br>ACTCTCGGCTGACCGTGGACAAGTCCCGGTGGCAG<br>GAAGGCAACGTCTTCTCCTGCTCCGTGATGCACGA<br>GGCCCTGCACAACCACTACACCCAGAAGTCCCTGT<br>CCCTGAGCCTGGGC |
| 102 | nLAGLC1 | GACATCCAGATGACCCAGAGCCCTAGCTTCCTGAG<br>CGCCAGCGTCGGCGACCGCGTGACCTTCACCTGCA<br>AGGCCAGCCAGGACGTGAGCACCGCCGTCGCCTGG<br>TATCAGCAGAAGCCTGGCAAGGCCCCAAAGCTGCT<br>GATCTACAGCGCCAGCTACCGCTACACCGGCGTGC<br>CAGACCGCTTCAGCGGCAGCGGCAGCGGCACCGAC<br>TTCACCCTGACCATCAGCAGCCTGCAACCAGAGGA<br>CTTCGCCACCTACTACTGCCAGCAGCACTACAGCA<br>TCCCACTGACCTTTGGCCAGGGCACCAAGCTGGAG<br>ATCAAGCGTACTGTGGCTGCACCATCTGTCTTCAT<br>CTTCCCGCCATCTGATGAGCAATTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| 103 | nLAGHC2 | CAGGTGACCCTGGTGGAGAGCGGCGGCGGCGTCGT<br>GCAGCCAGGCCGCAGCCTGAGCCTGAGCTGCGCTT<br>TCAGCGGCTTCAGCCTCAGCACCAGCGACATGGGC<br>GTGGGCTGGGTCCGCCAACCACCAGGCAAGGGCCT<br>GGAGTGGGTGGCCCACATCTGGTGGGACGACGTGA<br>AGCGCTACAACCCAGCCCTGAAGAGCCGCTTTACC<br>ATCAGCCGCGACAACAGCAAGAACACCCTGTACCT<br>GCAAATGAACAGCCTGCGCGCCGAGGACACCGCCA<br>CCTACTACTGCGCCCGCATCGAGGACTACGGCGTG<br>AGCTACTACTTCGACTACTGGGGCCAGGGCACCAC<br>CGTGACCGTGAGCAGCGCCTCCACAAAGGGCCCTT<br>CCGTGTTCCCCCTGGCCCCTTGCTCCCGGTCCACC<br>TCCGAGTCTACCGCCGCTCTGGGCTGCCTGGTCAA<br>GGACTACTTCCCCGAGCCCGTGACCGTGTCCTGGA<br>ACTCTGGCGCCCTGACCTCCGGCGTGCACACCTTC<br>CCTGCTGTGCTGCAGTCCTCCGGCCTGTACTCCCT<br>GTCCTCCGTCGTGACCGTGCCCTCCTCTAGCCTGG<br>GCACCAAGACCTACACCTGTAACGTGGACCACAAG<br>CCCTCCAACACCAAGGTGGACAAGCGGGTGGAATC<br>TAAGTACGGCCCTCCCTGCCCCCCCTGCCCTGCCC<br>CTGAATTTCTGGGCGGACCCTCCGTGTTCCTGTTC<br>CCCCCAAAGCCCAAGGACACCCTGATGATCTCCCG<br>GACCCCCGAAGTGACCTGCGTGGTGGTGGACGTGT<br>CCCAGGAAGATCCCGAGGTCCAGTTTAATTGGTAC<br>GTGGACGGCGTGGAAGTGCACAACGCCAAGACCAA<br>GCCCAGAGAGGAACAGTTCAACTCCACCTACCGGG<br>TGGTGTCCGTGCTGACCGTGCTGCACCAGGACTGG<br>CTGAACGGCAAAGAGTACAAGTGCAAGGTGTCCAA<br>CAAGGGCCTGCCCTCCAGCATCGAAAAGACCATCT<br>CCAAGGCCAAGGGCCAGCCCCGCGAGCCCCAGGTG<br>TACACCCTGCCTCCAAGCCAGGAAGAGATGACCAA<br>GAACCAGGTGTCCCTGACCTGTCTGGTCAAGGGCT<br>TCTACCCCTCCGATATCGCCGTGGAATGGGAGTCC<br>AACCGGCAGCCCGAGAACAACTACAAGACCACCCC<br>CCCTGTGCTGGACTCCGACGGCTCCTTCTTCCTGT<br>ACTCTCGGCTGACCGTGGACAAGTCCCGGTGGCAG<br>GAAGGCAACGTCTTCTCCTGCTCCGTGATGCACGA |

| SEQUENCE NUMBER | SEQUENCE NAME | SEQUENCE |
|---|---|---|
| | | GGCCCTGCACAACCACTACACCCAGAAGTCCCTGT CCCTGAGCCTGGGC |
| 104 | nLAGLC2 | GACATCCAGATGACCCAGAGCCCTAGCTTCCTGAG CGCCAGCGTCGGCGACCGCGTGACGATCACCTGCA AGGCCAGCCAGGACGTGAGCACCGCCGTCGCCTGG TATCAGCAGAAGCCTGGCAAGGCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCACCTACTACTGCCAGCAGCACTACAGCA TCCCACTGACCTTTGGCGCCGGCACCAAGCTGGAG ATCAAGCGTACTGTGGCTGCACCATCTGTCTTCAT CTTCCCGCCATCTGATGAGCAATTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| 105 | nLAGHC3 | CAGGTGACCCTGGTGGAGAGCGGCGGCGGCGTCGT GCAGCCAGGCCGCAGCCTGCGCCTGAGCTGCGCTT TCAGCGGCTTCAGCCTCAGCACCAGCGACATGGGC GTGGGCTGGATCCGCCAAGCCCCAGGCAAGGGCCT GGAGTGGGTGGCCCACATCTGGTGGGACGACGTGA AGCGCTACAACCCAGCCCTGAAGAGCCGCTTTACC ATCAGCCGCGACAACAGCAAGAACACCCTGTACCT GCAAATGAACAGCCTGCGCGCCGAGGACACCGCCA CCTACTTCTGCGCCCGCATCGAGGACTACGGCGTG AGCTACTACTTCGACTACTGGGGCCAGGGCACCAC CGTGACCGTGAGCAGCGCCTCCACAAAGGGCCCTT CCGTGTTCCCCCTGGCCCCTTGCTCCCGGTCCACC TCCGAGTCTACCGCCGCTCTGGGCTGCCTGGTCAA GGACTACTTCCCCGAGCCCGTGACCGTGTCCTGGA ACTCTGGCGCCCTGACCTCCGGCGTGCACACCTTC CCTGCTGTGCTGCAGTCCTCCGGCCTGTACTCCCT GTCCTCCGTCGTGACCGTGCCCTCCTCTAGCCTGG GCACCAAGACCTACACCTGTAACGTGGACCACAAG CCCTCCAACACCAAGGTGGACAAGCGGGTGGAATC TAAGTACGGCCCTCCCTGCCCCCCCTGCCCTGCCC CTGAATTTCTGGGCGGACCCTCCGTGTTCCTGTTC CCCCCAAAGCCCAAGGACACCCTGATGATCTCCCG GACCCCCGAAGTGACCTGCGTGGTGGTGGACGTGT CCCAGGAAGATCCCGAGGTCCAGTTTAATTGGTAC GTGGACGGCGTGGAAGTGCACAACGCCAAGACCAA GCCCAGAGAGGAACAGTTCAACTCCACCTACCGGG TGGTGTCCGTGCTGACCGTGCTGCACCAGGACTGG CTGAACGGCAAAGAGTACAAGTGCAAGGTGTCCAA CAAGGGCCTGCCCTCCAGCATCGAAAAGACCATCT CCAAGGCCAAGGGCCAGCCCCGCGAGCCCCAGGTG TACACCCTGCCTCCAAGCCAGGAAGAGATGACCAA GAACCAGGTGTCCCTGACCTGTCTGGTCAAGGGCT TCTACCCCTCCGATATCGCCGTGGAATGGGAGTCC AACGGCCAGCCCGAGAACAACTACAAGACCACCCC CCCTGTGCTGGACTCCGACGGCTCCTTCTTCCTGT ACTCTCGGCTGACCGTGGACAAGTCCCGGTGGCAG GAAGGCAACGTCTTCTCCTGCTCCGTGATGCACGA GGCCCTGCACAACCACTACACCCAGAAGTCCCTGT CCCTGAGCCTGGGC |
| 106 | nLAGLC3 | GACATCGTGATGACCCAGAGCCCTAGCTTCCTGAG CGCCAGCGTCGGCGACCGCGTGACCATCACCTGCA AGGCCAGCCAGGACGTGAGCACCGCCGTCGCCTGG TATCAGCAGAAGCCTGGCAAGGCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCACCTACTACTGCCAGCAGCACTACAGCA TCCCACTGACCTTTGGCCAGGGCACCAAGCTGGAG ATCAAGCGTACTGTGGCTGCACCATCTGTCTTCAT CTTCCCGCCATCTGATGAGCAATTGAAATCTGGAA CTGCCTCTGTTGTGTGCCTGCTGAATAACTTCTAT CCCAGAGAGGCCAAAGTACAGTGGAAGGTGGATAA |

| SEQUENCE NUMBER | SEQUENCE NAME | SEQUENCE |
|---|---|---|
| | | CGCCCTCCAATCGGGTAACTCCCAGGAGAGTGTCA |
| | | CAGAGCAGGACAGCAAGGACAGCACCTACAGCCTC |
| | | AGCAGCACCCTGACGCTGAGCAAAGCAGACTACGA |
| | | GAAACACAAAGTCTACGCCTGCGAAGTCACCCATC |
| | | AGGGCCTGAGCTCGCCCGTCACAAAGAGCTTCAAC |
| | | AGGGGAGAGTGT |
| 107 | nLAGHC4 | CAGGTGACCCTGGTGGAGAGCGGCGGCGGCGTCGT |
| | | GCAGCCAGGCCGCAGCCTGCGCCTGAGCTGCGCTT |
| | | TCAGCGGCTTCAGCCTCAGCACCAGCGACATGGGC |
| | | GTGGGCTGGATCCGCCAAGCCCCAGGCAAGGGCCT |
| | | GGAGTGGGTGGCCCACATCTGGTGGGACGACGTGA |
| | | AGCGCTACAACCCAGCCCTGAAGAGCCGCTTTACC |
| | | ATCAGCCGCGACAACAGCAAGAACACCCTGTACCT |
| | | GCAAATGAACAGCCTGCGCGCCGAGGACACCGCCG |
| | | TGTACTTCTGCGCCCGCATCGAGGACTACGGCGTG |
| | | AGCTACTACTTCGACTACTGGGGCCAGGGCACCAC |
| | | CGTGACCGTGAGCAGCGCCTCCACAAAGGGCCCTT |
| | | CCGTGTTCCCCCTGGCCCCTTGCTCCCGGTCCACC |
| | | TCCGAGTCTACCGCCGCTCTGGGCTGCCTGGTCAA |
| | | GGACTACTTCCCCGAGCCCGTGACCGTGTCCTGGA |
| | | ACTCTGGCGCCCTGACCTCCGGCGTGCACACCTTC |
| | | CCTGCTGTGCTGCAGTCCTCCGGCCTGTACTCCCT |
| | | GTCCTCCGTCGTGACCGTGCCCTCCTCTAGCCTGG |
| | | GCACCAAGACCTACACCTGTAACGTGGACCACAAG |
| | | CCCTCCAACACCAAGGTGGACAAGCGGGTGGAATC |
| | | TAAGTACGGCCCTCCCTGCCCCCCCCTGCCCTGCCC |
| | | CTGAATTTCTGGGCGGACCCTCCGTGTTCCTGTTC |
| | | CCCCCAAAGCCCAAGGACACCCTGATGATCTCCCG |
| | | GACCCCCGAAGTGACCTGCGTGGTGGTGGACGTGT |
| | | CCCAGGAAGATCCCGAGGTCCAGTTTAATTGGTAC |
| | | GTGGACGGCGTGGAAGTGCACAACGCCAAGACCAA |
| | | GCCCAGAGAGGAACAGTTCAACTCCACCTACCGGG |
| | | TGGTGTCCGTGCTGACCGTGCTGCACCAGGACTGG |
| | | CTGAACGGCAAAGAGTACAAGTGCAAGGTGTCCAA |
| | | CAAGGGCCTGCCCTCCAGCATCGAAAAGACCATCT |
| | | CCAAGGCCAAGGGCCAGCCCCGCGAGCCCCAGGTG |
| | | TACACCCTGCCTCCAAGCCAGGAAGAGATGACCAA |
| | | GAACCAGGTGTCCCTGACCTGTCTGGTCAAGGGCT |
| | | TCTACCCCTCCGATATCGCCGTGGAATGGGAGTCC |
| | | AACGGCCAGCCCGAGAACAACTACAAGACCACCCC |
| | | CCCTGTGCTGGACTCCGACGGCTCCTTCTTCCTGT |
| | | ACTCTCGGCTGACCGTGGACAAGTCCCGGTGGCAG |
| | | GAAGGCAACGTCTTCTCCTGCTCCGTGATGCACGA |
| | | GGCCCTGCACAACCACTACACCCAGAAGTCCCTGT |
| | | CCCTGAGCCTGGGC |
| 108 | nLAGLC4 | GACATCCAGATGACCCAGAGCCCTAGCTTCCTGAG |
| | | CGCCAGCGTCGGCGACCGCGTGAGCATCACCTGCA |
| | | AGGCCAGCCAGGACGTGAGCACCGCCGTCGCCTGG |
| | | TATCAGCAGAAGCCTGGCAAGGCCCCAAAGCTGCT |
| | | GATCTACAGCGCCAGCTACCGCTACACCGGCGTGC |
| | | CAGACCGCTTCAGCGGCAGCGGCAGCGGCACCGAC |
| | | TTCACCCTGACCATCAGCAGCCTGCAACCAGAGGA |
| | | CTTCGCCACCTACTACTGCCAGCAGCACTACAGCA |
| | | TCCCACTGACCTTTGGCCAGGGCACCAAGCTGGAG |
| | | ATCAAGCGTACTGTGGCTGCACCATCTGTCTTCAT |
| | | CTTCCCGCCATCTGATGAGCAATTGAAATCTGGAA |
| | | CTGCCTCTGTTGTGTGCCTGCTGAATAACTTCTAT |
| | | CCCAGAGAGGCCAAAGTACAGTGGAAGGTGGATAA |
| | | CGCCCTCCAATCGGGTAACTCCCAGGAGAGTGTCA |
| | | CAGAGCAGGACAGCAAGGACAGCACCTACAGCCTC |
| | | AGCAGCACCCTGACGCTGAGCAAAGCAGACTACGA |
| | | GAAACACAAAGTCTACGCCTGCGAAGTCACCCATC |
| | | AGGGCCTGAGCTCGCCCGTCACAAAGAGCTTCAAC |
| | | AGGGGAGAGTGT |
| 109 | nLAGHC5 | CAGGTCACCCTGAAGGAGAGCGGCCCCAACCCTGGT |
| | | GAAGCCAACCCAGACCCTGACCCTGACCTGCAGCT |
| | | TCAGCGGCTTCTCCCTGAGCACCAGCGACATGGGC |
| | | GTGGGCTGGATTCGCCAACCACCAGGCAAGGCCCT |
| | | GGAGTGGCTGGCCCACATCTGGTGGGACGACGTGA |
| | | AGCGCTACAACCCAGCCCTGAAGAGCCGCCTGACC |
| | | ATCACCAAGGACACCAGCAAGAACCAGGTGGTGCT |
| | | GACCATGACCAACATGGACCCAGTGGACACCGCCA |
| | | CCTACTTCTGCGCCCGCATCGTGGACTACGGCGTG |

| SEQUENCE NUMBER | SEQUENCE NAME | SEQUENCE |
|---|---|---|
| | | AGCTACTACTTCGACTACTGGGGCCAGGGCACCAC CGTGACCGTGAGCAGCGCCTCCACAAAGGGCCCTT CCGTGTTCCCCCTGGCCCCTTGCTCCCGGTCCACC TCCGAGTCTACCGCCGCTCTGGGCTGCCTGGTCAA GGACTACTTCCCCGAGCCCGTGACCGTGTCCTGGA ACTCTGGCGCCCTGACCTCCGGCGTGCACACCTTC CCTGCTGTGCTGCAGTCCTCCGGCCTGTACTCCCT GTCCTCCGTCGTGACCGTGCCCTCCTCTAGCCTGG GCACCAAGACCTACACCTGTAACGTGGACCACAAG CCCTCCAACACCAAGGTGGACAAGCGGGTGGAATC TAAGTACGGCCCTCCCTGCCCCCCCTGCCCTGCCC CTGAATTTCTGGGCGGACCCTCCGTGTTCCTGTTC CCCCCAAAGCCCAAGGACACCCTGATGATCTCCCG GACCCCCGAAGTGACCTGCGTGGTGGTGGACGTGT CCCAGGAAGATCCCGAGGTCCAGTTTAATTGGTAC GTGGACGGCGTGGAAGTGCACAACGCCAAGACCAA GCCCAGAGAGGAACAGTTCAACTCCACCTACCGGG TGGTGTCCGTGCTGACCGTGCTGCACCAGGACTGG CTGAACGGCAAAGAGTACAAGTGCAAGGTGTCCAA CAAGGGCCTGCCCTCCAGCATCGAAAAGACCATCT CCAAGGCCAAGGGCCAGCCCCGCGAGCCCCAGGTG TACACCCTGCCTCCAAGCCAGGAAGAGATGACCAA GAACCAGGTGTCCCTGACCTGTCTGGTCAAGGGCT TCTACCCCTCCGATATCGCCGTGGAATGGGAGTCC AACGGCCAGCCCGAGAACAACTACAAGACCACCCC CCCTGTGCTGGACTCCGACGGCTCCTTCTTCCTGT ACTCTCGGCTGACCGTGGACAAGTCCCGGTGGCAG GAAGGCAACGTCTTCTCCTGCTCCGTGATGCACGA GGCCCTGCACAACCACTACACCCAGAAGTCCCTGT CCCTGAGCCTGGGC |
| 110 | nLAGLC5 | GACATCCAGATGACCCAGAGCCCTAGCTTCCTGAG CGCCAGCGTCGGCGACCGCGTGAGCATCACCTGCA AGGCCAGCCAGGACGTGAGCACCGCCGTCGCCTGG TATCAGCAGAAGCCTGGCAAGGCCCCCAAAGCTGCT GATCTACAGCGCCAGCTACCGCTACACCGGCGTGC CAGACCGCTTCAGCGGCAGCGGCAGCGGCACCGAC TTCACCCTGACCATCAGCAGCCTGCAACCAGAGGA CTTCGCCGTGTACTACTGCCAGCAGCACTACAGCA TCCCACTGACCTTTGGCCAGGGCACCAAGCTGGAG ATCAAGCGTACTGTGGCTGCACCATCTGTCTTCAT CTTCCCGCCATCTGATGAGCAATTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| 111 | LAG3 epitope1 | LLRRAGVT |
| 112 | LAG3 epitope2 | YRAAVHLRDRA |
| 113 | 77E11 VK | DIVLTQSPASLAVSLGQRATMSCRASENIDNSGIS FMNWFQQKPGQPPKLLIYVASNQGSGVPARFSGSG SGTDFRLTIHPLEEDDTAMYFCQQSKEVPWTFGGG TKLEIK |
| 114 | 77E11 VH | EVMLVESGGGLVKPGGSLKLSCTASGFTFSNSAMS WVRQTPERRLEWVAYISGGGGDTYYSDSVKGRFTI SRDNAKDTLYLHMSSLRSEDTALHYCARHSNSNYY AMDYWGQGTSVTVSS |
| 115 | PD1 epitope | AISLAPKAQIKESL |
| 116 | PD1 epitope | AAFPEDRSQPGQDCRF |
| 117 | 496G6 VK | DIVMTQSHKFMSTSVGDRVSFTCKASQDVNTAVAW YQQKPGQSPKLLIYSASYRYTGVPDRFTGSGSGTD FTFTISSVQAEDLALYYCQQHYSIPLTFGAGTKLE LK |

| SEQUENCE NUMBER | SEQUENCE NAME | SEQUENCE |
|---|---|---|
| 118 | 496G6 VH | QVTLKESGPGILQPSQTLSLTCSFSGFSLSTSDMG VGWIRQPSGKGLEWLAHIWWDDVKRYNPALKSRLT ISKDTSSSQVFLMIASVDTADTATYFCARIEDYGV SYYFDYWGQGTTLTVSS |

FURTHER EMBODIMENTS OF THE INVENTION

Embodiment 1

An anti-PD1 antibody molecule comprising:
(a) heavy chain CDRs comprising the amino acid sequence of SEQ ID NO:1 (hcCDR1), SEQ ID NO:2 (hcCDR2) and SEQ ID NO:3 (hcCDR3) and has light chain CDRs comprising the amino acid sequence of SEQ ID NO:4 (lcCDR1), SEQ ID NO:5 (lcCDR2) and SEQ ID NO:6 (lcCDR3); or,
(b) heavy chain CDRs comprising the amino acid sequence of SEQ ID NO:7 (hcCDR1), SEQ ID NO:8 (hcCDR2) and SEQ ID NO:9 (hcCDR3) and has light chain CDRs comprising the amino acid sequence of SEQ ID NO:10 (lcCDR1), SEQ ID NO:11 (lcCDR2) and SEQ ID NO:12 (lcCDR3); or,
(c) heavy chain CDRs comprising the amino acid sequence of SEQ ID NO:13 (hcCDR1), SEQ ID NO:14 (hcCDR2) and SEQ ID NO:15 (hcCDR3) and has light chain CDRs comprising the amino acid sequence of SEQ ID NO:16 (lcCDR1), SEQ ID NO:17 (lcCDR2) and SEQ ID NO:18 (lcCDR3).

Embodiment 2

The anti-PD1 antibody molecule of embodiment 1 wherein said antibody molecule is a humanized antibody molecule.

Embodiment 3

The anti-PD1 antibody molecule of embodiment 1 or 2 wherein said antibody molecule is a monoclonal antibody molecule, Fab, F(ab')2, Fv or scFv.

Embodiment 4

The anti-PD1 antibody molecule of any of the previous embodiments which comprises a heavy chain constant region selected from the group consisting of IgG1, IgG2, IgG3, IgG4, IgM, IgA and IgE constant regions.

Embodiment 5

The anti-PD1 antibody molecule of embodiment 4 wherein the heavy chain constant region is IgG4, preferably IgG4 with a S241P mutation.

Embodiment 6

The anti-PD1 antibody molecule of any of embodiments 1 to 5 wherein the light chain constant region is kappa or lambda.

Embodiment 7

The anti-PD1 antibody molecule of any of embodiments 1 to 5 wherein said antibody molecule has a heavy chain variable domain comprising an amino acid sequence at least 85% identical to any of SEQ ID NOs: 19, 21, 23, 25 and 27.

Embodiment 8

The anti-PD1 antibody molecule of any of embodiments 1 to 7 wherein said antibody molecule has a heavy chain variable domain comprising an amino acid sequence of any of SEQ ID NOs: 19, 21, 23, 25 and 27.

Embodiment 9

The anti-PD1 antibody molecule of any of embodiments 1 to 8 wherein said antibody molecule has a light chain variable domain comprising an amino acid sequence at least 85% identical to any of SEQ ID NOs: 20, 22, 24, 26 and 28.

Embodiment 10

The anti-PD1 antibody molecule of any of embodiments 1 to 9 wherein said antibody molecule has a light chain variable domain comprising the amino acid sequence of SEQ ID NOs: 20, 22, 24, 26 and 28.

Embodiment 11

The anti-PD1 antibody molecule of any of embodiments 1 to 10 wherein said antibody molecule has a heavy chain comprising the amino acid sequence of SEQ ID NO: 29, 31, 33, 35 or 37.

Embodiment 12

The anti-PD1 antibody molecule of any of embodiments 1 to 11 wherein said antibody molecule has a light chain comprising the amino acid sequence of SEQ ID NO: 30, 32, 34, 36 or 38.

Embodiment 13

The anti-PD1 antibody molecule of any of embodiments 1 to 12 wherein said antibody molecule has a heavy chain variable domain comprising the amino acid sequence of SEQ ID NO: 19 and a light chain variable domain comprising the amino acid sequence of SEQ ID NO: 20, or a heavy chain variable domain comprising the amino acid sequence of SEQ ID NO: 21 and a light chain variable domain comprising the amino acid sequence of SEQ ID NO: 22, or a heavy chain variable domain comprising the amino acid sequence of SEQ ID NO: 23 and a light chain variable domain comprising the amino acid sequence of SEQ ID NO: 24, or a heavy chain variable domain comprising the amino acid sequence of SEQ ID NO: 25 and a light chain variable domain comprising the amino acid sequence of SEQ ID NO: 26, or a heavy chain variable domain comprising the amino acid sequence of SEQ ID NO: 27 and a light chain variable domain comprising the amino acid sequence of SEQ ID NO: 28.

Embodiment 14

The anti-PD1 antibody molecule of any of embodiments 1 to 13 wherein said antibody molecule has a heavy chain comprising the amino acid sequence of SEQ ID NO: 29 and a light chain comprising the amino acid sequence of SEQ ID NO: 30 or a heavy chain comprising the amino acid sequence of SEQ ID NO: 31 and a light chain comprising the amino acid sequence of SEQ ID NO: 32, or a heavy chain comprising the amino acid sequence of SEQ ID NO: 33 and a light chain comprising the amino acid sequence of SEQ ID NO:34, or a heavy chain comprising the amino acid sequence of SEQ ID NO: 35 and a light chain comprising the amino acid sequence of SEQ ID NO: 36, or a heavy chain comprising the amino acid sequence of SEQ ID NO: 37 and a light chain comprising the amino acid sequence of SEQ ID NO: 38.

Embodiment 15

The anti-PD1 antibody molecule of any of embodiments 1 to 14 which is capable of reducing the binding of human PD-L1/L2 with human PD1.

Embodiment 16

The anti-PD1 antibody molecule of any of embodiments 1 to 15 which is capable of enhancing an antigen-specific T cell response.

Embodiment 17

An isolated nucleic acid molecule encoding the heavy chain variable domain and/or the light chain variable domain of an antibody molecule of any of embodiments 1 to 16.

Embodiment 18

The nucleic acid molecule of embodiment 17 which has the nucleotide sequence of SEQ ID NOs: 71, 73, 75, 77 or 79 encoding the heavy chain variable domain of the antibody molecule defined in embodiment 8.

Embodiment 19

The nucleic acid molecule of embodiment 17 which has the nucleotide sequence of SEQ ID NOs: 72, 74, 76, 78 or 80 encoding the light chain variable domain of the antibody molecule defined in embodiment 10.

Embodiment 20

An expression vector containing a nucleic acid molecule comprising the nucleotide sequence encoding the heavy chain variable domain and/or the light chain variable domain of an antibody molecule of any one of embodiments 1 to 16.

Embodiment 21

The expression vector of embodiment 20 containing a nucleic acid molecule comprising the nucleotide sequence of SEQ ID NO: 71 and/or SEQ ID NO: 72, or comprising the nucleotide sequence of SEQ ID NO: 73 and/or SEQ ID NO: 74, or comprising the nucleotide sequence of SEQ ID NO: 75 and/or SEQ ID NO: 76, or comprising the nucleotide sequence of SEQ ID NO: 77 and/or SEQ ID NO: 78 or comprising the nucleotide sequence of SEQ ID NO: 79 and/or SEQ ID NO: 80.

Embodiment 22

The expression vector of embodiment 20 or 21 comprising, in addition, a nucleic acid molecule encoding the heavy chain constant domains and/or the light chain constant domain, respectively, linked to the nucleic acid molecule encoding the heavy chain variable domain and/or the light chain variable domain, respectively.

Embodiment 23

A host cell having an expression vector encoding a heavy chain of an antibody molecule of any one of embodiments 1 to 16, and an expression vector encoding a light chain of an antibody molecule of any one of claims 1 to 16.

Embodiment 24

The host cell of embodiment 23 wherein the cell is a mammalian cell.

Embodiment 25

A method of manufacturing an antibody molecule of any of embodiments 1 to 16 comprising the steps of:
culturing a host cell according to embodiment 23 or 24 under conditions that allow formation of an antibody molecule according to any of embodiments 1 to 16; and,
recovering said antibody molecule.

Embodiment 26

The method of embodiment 25, additionally comprising the step of purifying said antibody molecule.

Embodiment 27

The method of embodiment 25 or 26, additionally comprising the step of formulating said antibody molecule into a pharmaceutical composition.

Embodiment 28

The antibody molecule of any of embodiments 1 to 16 for use in medicine.

Embodiment 29

A pharmaceutical composition comprising an anti-PD1 antibody of any of embodiments 1 to 16 and a pharmaceutically acceptable carrier.

Embodiment 30

The pharmaceutical composition of embodiment 29 further comprising an anti-LAG3 antibody molecule.

Embodiment 31

A kit of parts comprising an anti-PD1 antibody of any of embodiments 1 to 16 and an anti-LAG3 antibody molecule.

Embodiment 32

The composition of embodiment 30 or the kit of embodiment 31 wherein said anti-LAG3 antibody molecule binds an epitope of human LAG3 comprising the amino acid sequence LLRRAGVT (SEQ ID NO: 111) and/or YRAAVHLRDRA (SEQ ID NO: 112).

Embodiment 33

The composition or the kit of any of embodiments 30 to 32 wherein said anti-LAG3 antibody molecule comprises:
(a) heavy chain CDRs comprising the amino acid sequence of SEQ ID NO:39 (hcCDR1), SEQ ID NO:40 (hcCDR2) and SEQ ID NO:41 (hcCDR3) and has light chain CDRs comprising the amino acid sequence of SEQ ID NO:42 (lcCDR1), SEQ ID NO:43 (lcCDR2) and SEQ ID NO:44 (lcCDR3); or,
(b) heavy chain CDRs comprising the amino acid sequence of SEQ ID NO:45 (hcCDR1), SEQ ID NO:46 (hcCDR2) and SEQ ID NO:47 (hcCDR3) and has light chain CDRs comprising the amino acid sequence of SEQ ID NO:48 (lcCDR1), SEQ ID NO:49 (lcCDR2) and SEQ ID NO:50 (lcCDR3).

Embodiment 34

The composition or the kit of any of embodiments 30 to 33 wherein said anti-LAG3 antibody molecule has
a heavy chain variable domain comprising the amino acid sequence of SEQ ID NO: 51 and has a light chain variable domain comprising the amino acid sequence of SEQ ID NO: 52, or
a heavy chain variable domain comprising the amino acid sequence of SEQ ID NO: 53 and has a light chain variable domain comprising the amino acid sequence of SEQ ID NO: 54, or
a heavy chain variable domain comprising the amino acid sequence of SEQ ID NO: 55 and has a light chain variable domain comprising the amino acid sequence of SEQ ID NO: 56, or
a heavy chain variable domain comprising the amino acid sequence of SEQ ID NO: 57 and has a light chain variable domain comprising the amino acid sequence of SEQ ID NO: 58, or
a heavy chain variable domain comprising the amino acid sequence of SEQ ID NO: 59 and has a light chain variable domain comprising the amino acid sequence of SEQ ID NO: 60.

Embodiment 35

The composition or the kit of any of embodiments 30 to 34 wherein said anti-LAG3 antibody molecule has
a heavy chain comprising the amino acid sequence of SEQ ID NO: 61 and has a light chain comprising the amino acid sequence of SEQ ID NO: 62, or
a heavy chain comprising the amino acid sequence of SEQ ID NO: 63 and has a light chain comprising the amino acid sequence of SEQ ID NO: 64, or
a heavy chain comprising the amino acid sequence of SEQ ID NO: 65 and has a light chain comprising the amino acid sequence of SEQ ID NO: 66, or
a heavy chain comprising the amino acid sequence of SEQ ID NO: 67 and has a light chain comprising the amino acid sequence of SEQ ID NO: 68, or
a heavy chain comprising the amino acid sequence of SEQ ID NO: 69 and has a light chain comprising the amino acid sequence of SEQ ID NO: 70.

Embodiment 36

The composition or the kit of any of embodiments 30 to 35 further comprising one or more additional therapeutic agents.

Embodiment 37

A method of treating cancer comprising administering to a patient in need thereof a therapeutically effective amount of the anti-PD1 antibody molecule of any of embodiments 1 to 16.

Embodiment 38

The anti-PD1 antibody molecule of any of embodiments 1 to 16, for use in a method of treating cancer.

Embodiment 39

Use of the anti-PD1 antibody molecule of any of embodiments 1 to 16 for preparing a pharmaceutical composition for treating cancer.

Embodiment 40

The method or use of an anti-PD1 antibody molecule of any of embodiments 37 to 39 further comprising an anti-LAG3 antibody molecule.

Embodiment 41

The method or use of embodiment 40 wherein the anti-PD1 antibody molecule is to be administered simultaneously, concurrently, sequentially, successively, alternatively or separately, with the anti-LAG3 antibody molecule.

Embodiment 42

The method or use of embodiment 40 or 41 wherein said LAG3 antibody molecule binds an epitope of human LAG3 comprising the amino acid sequence LLRRAGVT (SEQ ID NO: 111) and/or YRAAVHLRDRA (SEQ ID NO: 112).

Embodiment 43

The method or use of embodiments 40 to 42 wherein said LAG3 antibody molecule comprises:
(a) heavy chain CDRs comprising the amino acid sequence of SEQ ID NO:39 (hcCDR1), SEQ ID NO:40 (hcCDR2) and SEQ ID NO:41 (hcCDR3) and has light chain CDRs comprising the amino acid sequence of SEQ ID NO:42 (lcCDR1), SEQ ID NO:43 (lcCDR2) and SEQ ID NO:44 (lcCDR3); or,
(b) heavy chain CDRs comprising the amino acid sequence of SEQ ID NO:45 (hcCDR1), SEQ ID NO:46 (hcCDR2) and SEQ ID NO:47 (hcCDR3) and has light chain CDRs comprising the amino acid sequence of SEQ ID NO:48 (lcCDR1), SEQ ID NO:49 (lcCDR2) and SEQ ID NO:50 (lcCDR3).

Embodiment 44

The method or use of any of embodiments 20 to 43 wherein said anti-LAG3 antibody molecule has
- a heavy chain variable domain comprising the amino acid sequence of SEQ ID NO: 51 and has a light chain variable domain comprising the amino acid sequence of SEQ ID NO: 52, or
- a heavy chain variable domain comprising the amino acid sequence of SEQ ID NO: 53 and has a light chain variable domain comprising the amino acid sequence of SEQ ID NO: 54, or
- a heavy chain variable domain comprising the amino acid sequence of SEQ ID NO: 55 and has a light chain variable domain comprising the amino acid sequence of SEQ ID NO: 56, or
- a heavy chain variable domain comprising the amino acid sequence of SEQ ID NO: 57 and has a light chain variable domain comprising the amino acid sequence of SEQ ID NO: 58, or
- a heavy chain variable domain comprising the amino acid sequence of SEQ ID NO: 59 and has a light chain variable domain comprising the amino acid sequence of SEQ ID NO: 60.

Embodiment 45

The method or use of any of embodiments 40 to 44 wherein said anti-LAG3 antibody molecule has
- a heavy chain comprising the amino acid sequence of SEQ ID NO: 61 and has a light chain comprising the amino acid sequence of SEQ ID NO: 62, or
- a heavy chain comprising the amino acid sequence of SEQ ID NO: 63 and has a light chain comprising the amino acid sequence of SEQ ID NO: 64, or
- a heavy chain comprising the amino acid sequence of SEQ ID NO: 65 and has a light chain comprising the amino acid sequence of SEQ ID NO: 66, or
- a heavy chain comprising the amino acid sequence of SEQ ID NO: 67 and has a light chain comprising the amino acid sequence of SEQ ID NO: 68, or
- a heavy chain comprising the amino acid sequence of SEQ ID NO: 69 and has a light chain comprising the amino acid sequence of SEQ ID NO: 70.

Embodiment 46

The method or use of any of embodiments 37 to 45 wherein said cancer is a solid tumor cancer or a cancer of the hematopoietic system.

Embodiment 47

The method or use of any of embodiments 37 to 46 wherein the antibody molecule(s) is administered in combination with one or more further therapeutic agents or procedures.

Embodiment 48

The method or use of embodiment 47 wherein the one or more further therapeutic agents or procedures is selected from chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy.

Embodiment 49

An anti-LAG3 antibody molecule which binds to an epitope of human LAG3 comprising the amino acid sequence LLRRAGVT (SEQ ID NO: 111) and/or YRAAVHLRDRA (SEQ ID NO: 112).

Embodiment 50

The anti-LAG3 antibody molecule of embodiment 49 wherein said antibody molecule is a humanized antibody molecule.

Embodiment 51

The anti-LAG3 antibody molecule of embodiment 49 or 50 wherein said antibody molecule is a monoclonal antibody molecule, Fab, F(ab')2, Fv or scFv.

Embodiment 52

The anti-LAG3 antibody molecule of any of embodiments 49 to 51 which comprises a heavy chain constant region selected from the group consisting of IgG1, IgG2, IgG3, IgG4, IgM, IgA and IgE constant regions.

Embodiment 53

The anti-LAG3 antibody molecule of embodiment 52 wherein the heavy chain constant region is IgG4, preferably IgG4 with a S241P mutation.

Embodiment 54

The anti-LAG3 antibody molecule of any of embodiments 49 to 53 wherein the light chain constant region is kappa or lambda.

Embodiment 55

An anti-LAG3 antibody molecule comprising:
(a) heavy chain CDRs comprising the amino acid sequence of SEQ ID NO:39 (hcCDR1), SEQ ID NO:40 (hcCDR2) and SEQ ID NO:41 (hcCDR3) and has light chain CDRs comprising the amino acid sequence of SEQ ID NO:42 (lcCDR1), SEQ ID NO:43 (lcCDR2) and SEQ ID NO:44 (lcCDR3); or
(b) heavy chain CDRs comprising the amino acid sequence of SEQ ID NO:45 (hcCDR1), SEQ ID NO:46 (hcCDR2) and SEQ ID NO:47 (hcCDR3) and has light chain CDRs comprising the amino acid sequence of SEQ ID NO:48 (lcCDR1), SEQ ID NO:49 (lcCDR2) and SEQ ID NO:50 (lcCDR3).

Embodiment 56

The anti-LAG3 antibody molecule of any of embodiments 49 to 55 wherein said antibody molecule has a heavy chain variable domain comprising an amino acid sequence at least 85% identical to any of SEQ ID NOs: 51, 53, 55, 57 and 59.

Embodiment 57

The anti-LAG3 antibody molecule of any of embodiments 49 to 56 wherein said antibody molecule has a heavy chain variable domain comprising an amino acid sequence of any of SEQ ID NOs: 51, 53, 55, 57 and 59.

Embodiment 58

The anti-LAG3 antibody molecule of any of embodiments 49 to 57 wherein said antibody molecule has a light chain variable domain comprising an amino acid sequence at least 85% identical to any of SEQ ID NOs: 52, 54, 56, 58 and 60.

Embodiment 59

The anti-LAG3 antibody molecule of any of embodiments 49 to 58 wherein said antibody molecule has a light chain variable domain comprising the amino acid sequence of SEQ ID NOs: 52, 54, 56, 58 and 60.

Embodiment 60

The anti-LAG3 antibody molecule of any of embodiments 49 to 59 wherein said antibody molecule has a heavy chain comprising the amino acid sequence of SEQ ID NO: 61, 63, 65, 67 or 69.

Embodiment 61

The anti-LAG3 antibody molecule of any of embodiments 49 to 60 wherein said antibody molecule has a light chain comprising the amino acid sequence of SEQ ID NO: 62, 64, 66, 68 or 70.

Embodiment 62

The anti-LAG3 antibody molecule of any of embodiments 49 to 61 wherein said antibody molecule has
- a heavy chain variable domain comprising the amino acid sequence of SEQ ID NO: 51 and a light chain variable domain comprising the amino acid sequence of SEQ ID NO: 52, or
- a heavy chain variable domain comprising the amino acid sequence of SEQ ID NO: 53 and a light chain variable domain comprising the amino acid sequence of SEQ ID NO: 54, or
- a heavy chain variable domain comprising the amino acid sequence of SEQ ID NO: 55 and a light chain variable domain comprising the amino acid sequence of SEQ ID NO: 56, or
- a heavy chain variable domain comprising the amino acid sequence of SEQ ID NO: 57 and a light chain variable domain comprising the amino acid sequence of SEQ ID NO: 58, or
- a heavy chain variable domain comprising the amino acid sequence of SEQ ID NO: 59 and a light chain variable domain comprising the amino acid sequence of SEQ ID NO: 60.

63

The anti-LAG3 antibody molecule of any of embodiments 49 to 62 wherein said antibody molecule has
- a heavy chain comprising the amino acid sequence of SEQ ID NO: 61 and a light chain comprising the amino acid sequence of SEQ ID NO: 62, or
- a heavy chain comprising the amino acid sequence of SEQ ID NO: 63 and a light chain comprising the amino acid sequence of SEQ ID NO: 64, or
- a heavy chain comprising the amino acid sequence of SEQ ID NO: 65 and a light chain comprising the amino acid sequence of SEQ ID NO: 66, or
- a heavy chain comprising the amino acid sequence of SEQ ID NO: 67 and a light chain comprising the amino acid sequence of SEQ ID NO: 68, or
- a heavy chain comprising the amino acid sequence of SEQ ID NO: 69 and a light chain comprising the amino acid sequence of SEQ ID NO: 70.

Embodiment 64

The anti-LAG3 antibody molecule of any of embodiments 49 to 63 for use in medicine.

Embodiment 65

A pharmaceutical composition comprising an anti-LAG3 antibody of any of embodiments 49 to 63 and a pharmaceutically acceptable carrier.

Embodiment 66

The pharmaceutical composition of embodiment 65 further comprising
- an anti-PD1 antibody molecule, preferably an anti-PD1 antibody molecule of any of embodiments 1 to 16, pembrolizumab, or nivolumab, or
- an anti-PDL-1 antibody molecule, preferably atezolizumab, avelumab or durvalumab.

Embodiment 67

A kit of parts comprising
- an anti-LAG3 antibody molecule of any of embodiments 49 to 63 and
- an antibody molecule selected from the group consisting of anti-PD1 antibody molecules of any of embodiments 1 to 16, pembrolizumab, nivolumab, atezolizumab, avelumab and durvalumab.

Embodiment 68

The composition or the kit of parts of any of embodiments 65 to 67 further comprising one or more additional therapeutic agents.

Embodiment 69

A method of treating cancer comprising administering to a patient in need thereof a therapeutically effective amount of the anti-LAG3 antibody molecule of any of embodiments 49 to 63.

Embodiment 70

The anti-LAG3 antibody molecule of any of embodiments 49 to 63 for use in a method of treating cancer.

Embodiment 71

Use of an anti-LAG3 antibody molecule of any of embodiments 49 to 63 for preparing a pharmaceutical composition for treating cancer.

Embodiment 72

The method or use of any of embodiments 69 to 71 further comprising
an anti-PD1 antibody molecule or an anti-PDL1 antibody molecule.

Embodiment 73

The method or use of embodiment 72 wherein said anti-PD1 antibody molecule is an anti-PD1 antibody molecule of any of embodiments 1 to 16, pembrolizumab, or nivolumab, or wherein said anti-PDL-1 antibody molecule is atezolizumab, avelumab or durvalumab.

Embodiment 74

The method or use of embodiment 72 or embodiment 73 wherein the anti-LAG3 antibody molecule is to be administered simultaneously, concurrently, sequentially, successively, alternatively or separately, with the anti-PD1 or anti-PDL1 antibody molecule.

Embodiment 75

An isolated nucleic acid molecule encoding the heavy chain variable domain and/or the light chain variable domain of an antibody molecule of any of embodiments 49 to 63.

Embodiment 76

An expression vector containing a nucleic acid molecule encoding the heavy chain variable domain and/or the light chain variable domain of an antibody molecule of any one of embodiments 49 to 63.

Embodiment 77

The expression vector of embodiment 76 containing a nucleic acid molecule encoding the heavy chain and/or the light chain of an antibody molecule of any one of embodiments 49 to 63.

Embodiment 78

A host cell transfected with an expression vector of embodiment 76 or 77.

Embodiment 79

A method of manufacturing an antibody molecule of any of embodiments 49 to 63 comprising the steps of:
culturing a host cell according to embodiment 78 under conditions that allow formation of an antibody molecule according to any of embodiments 49 to 63 and recovering said antibody molecule.

Embodiment 80

The method of embodiment 79, additionally comprising the step of purifying said antibody molecule.

Embodiment 81

The method of embodiment 80, additionally comprising the step of formulating said antibody molecule into a pharmaceutical composition.

Embodiment 82

A pharmaceutical combination comprising an anti-PD1 antibody molecule according to any one of embodiments 1 to 16 and an anti-LAG3 antibody molecule according to any one of embodiments 49 to 63.

Embodiment 83

A pharmaceutical combination comprising an anti-PD1 antibody molecule selected from the group consisting of anti-PD1 antibody molecules PD1-1, PD1-2, PD1-3, PD1-4, and PD1-5, and an anti-LAG3 antibody molecule selected from the group consisting of anti-LAG3 antibody molecules LAG3-1, LAG3-2, LAG3-3, LAG3-4, and LAG3-5.

What is claimed is:

1. An anti-PD1 antibody molecule comprising a heavy chain variable domain comprising heavy chain CDRs comprising the amino acid sequence of SEQ ID NO:13 (hcCDR1), SEQ ID NO:14 (hcCDR2) and SEQ ID NO:15 (hcCDR3) and a light chain variable domain comprising light chain CDRs comprising the amino acid sequence of SEQ ID NO:16 (lcCDR1), SEQ ID NO:17 (lcCDR2) and SEQ ID NO:18 (lcCDR3).

2. The anti-PD1 antibody molecule of claim 1, wherein said antibody molecule is a humanized antibody molecule.

3. The anti-PD1 antibody molecule of claim 1, wherein said antibody molecule is selected from the group consisting of a monoclonal antibody molecule, a Fab, a F(ab')2, a Fv and an scFv.

4. The anti-PD1 antibody molecule of claim 1 which comprises a heavy chain constant region selected from the group consisting of IgG1, IgG2, IgG3, IgG4, IgM, IgA and IgE constant regions.

5. The anti-PD1 antibody molecule of claim 4, wherein the heavy chain constant region is a human heavy chain constant region of an IgG4 with a S241P mutation.

6. The anti-PD1 antibody molecule of claim 1, wherein the antibody molecule comprises a light chain constant region selected from the group consisting of kappa and lambda.

7. The anti-PD1 antibody molecule of claim 1, wherein said antibody molecule comprises a heavy chain variable domain comprising the amino acid sequence of SEQ ID NO: 23.

8. The anti-PD1 antibody molecule of claim 1, wherein said antibody molecule comprises a light chain variable domain comprising the amino acid sequence of SEQ ID NO: 24.

9. The anti-PD1 antibody molecule of claim 1, wherein said antibody molecule has a heavy chain comprising the amino acid sequence of SEQ ID NO: 33.

10. The anti-PD1 antibody molecule of claim 1, wherein said antibody molecule has a light chain comprising the amino acid sequence of SEQ ID NO: 34.

11. An anti-PD1 antibody molecule, wherein said antibody molecule comprises a heavy chain variable domain comprising the amino acid sequence of SEQ ID NO: 23 and a light chain variable domain comprising the amino acid sequence of SEQ ID NO: 24.

12. An anti-PD1 antibody molecule, wherein said antibody molecule has a heavy chain comprising the amino acid sequence of SEQ ID NO: 33 and a light chain comprising the amino acid sequence of SEQ ID NO:34.

13. An isolated nucleic acid molecule encoding the heavy chain variable domain and the light chain variable domain of an antibody molecule of claim 1.

14. The nucleic acid molecule of claim 13 which has the nucleotide sequence of SEQ ID NO: 75 encoding the heavy chain variable domain comprising the amino acid sequence of SEQ ID NO: 23.

15. The nucleic acid molecule of claim 13 which has the nucleotide sequence of SEQ ID NO: 76 encoding the light chain variable domain comprising the amino acid sequence of SEQ ID NO: 24.

16. An expression vector comprising a nucleic acid molecule comprising a nucleotide sequence encoding the heavy chain variable domain and the light chain variable domain of an antibody molecule of claim 1.

17. The expression vector of claim 16 comprising a nucleic acid molecule comprising the nucleotide sequence of SEQ ID NO: 75 and SEQ ID NO: 76.

18. The expression vector of claim 16, wherein said nucleic acid molecule further comprises a nucleotide sequence encoding heavy chain constant domains and light chain constant domain, respectively, linked to the nucleotide sequence encoding the heavy chain variable domain and the light chain variable domain, respectively.

19. A host cell comprising an expression vector comprising a nucleic acid molecule comprising a nucleotide sequence encoding a heavy chain variable domain of an antibody molecule of claim 1, and an expression vector comprising a nucleic acid molecule comprising the nucleotide sequence encoding a light chain variable domain of an antibody molecule of claim 1.

20. The host cell of claim 19, wherein the cell is a mammalian cell.

21. A method of manufacturing an antibody molecule of claim 1 comprising the steps of:
culturing a host cell comprising an expression vector comprising a nucleic acid molecule comprising a nucleotide sequence encoding a heavy chain variable domain of an antibody molecule of claim 1, and an expression vector comprising a nucleic acid molecule comprising a nucleotide sequence encoding a light chain variable domain of an antibody molecule of claim 1 under conditions that allow formation of an antibody molecule according to claim 1; and,
recovering said antibody molecule.

22. The method of claim 21, further comprising the step of purifying said antibody molecule.

23. The method of claim 21, further comprising the step of formulating said antibody molecule into a pharmaceutical composition.

24. A pharmaceutical composition comprising an anti-PD1 antibody of claim 1 and a pharmaceutically acceptable carrier.

25. A method of treating cancer comprising administering to a patient having cancer a therapeutically effective amount of the anti-PD1 antibody molecule of claim 1.

26. The method of claim 25, wherein said cancer is a solid tumor cancer or a cancer of the hematopoietic system.

27. The method of claim 25, wherein the antibody molecule is administered in combination with one or more further therapeutic agents or procedures.

28. The method of claim 27, wherein the one or more further therapeutic agents or procedures is selected from chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, and a cellular immunotherapy.

29. A host cell comprising an expression vector comprising a nucleic acid molecule comprising a nucleotide sequence encoding a heavy chain variable domain of an antibody molecule of claim 11, and an expression vector comprising a nucleic acid molecule comprising a nucleotide sequence encoding a light chain variable domain of an antibody molecule of claim 11.

30. The host cell of claim 29, wherein the cell is a mammalian cell.

31. A method of manufacturing an antibody molecule of claim 11 comprising the steps of:
culturing a host cell comprising an expression vector comprising a nucleic acid molecule comprising a nucleotide sequence encoding a heavy chain variable domain of an antibody molecule of claim 11, and an expression vector comprising a nucleic acid molecule comprising a nucleotide sequence encoding a light chain variable domain of an antibody molecule of claim 11 under conditions that allow formation of an antibody molecule according to claim 11; and,
recovering said antibody molecule.

32. The method of claim 31, further comprising the step of purifying said antibody molecule.

33. The method of claim 31, further comprising the step of formulating said antibody molecule into a pharmaceutical composition.

34. A pharmaceutical composition comprising an anti-PD1 antibody of claim 11 and a pharmaceutically acceptable carrier.

35. A host cell comprising an expression vector comprising a nucleic acid molecule comprising a nucleotide sequence encoding a heavy chain variable domain of an antibody molecule of claim 12, and an expression vector comprising a nucleic acid molecule comprising a nucleotide sequence encoding a light chain variable domain of an antibody molecule of claim 12.

36. The host cell of claim 35, wherein the cell is a mammalian cell.

37. A method of manufacturing an antibody molecule of claim 12 comprising the steps of:
culturing a host cell comprising an expression vector comprising a nucleic acid molecule comprising a nucleotide sequence encoding a heavy chain variable domain of an antibody molecule of claim 12, and an expression vector comprising a nucleic acid molecule comprising a nucleotide sequence encoding a light chain variable domain of an antibody molecule of claim 12 under conditions that allow formation of an antibody molecule according to claim 12; and,
recovering said antibody molecule.

38. The method of claim 37, further comprising the step of purifying said antibody molecule.

39. The method of claim 37, further comprising the step of formulating said antibody molecule into a pharmaceutical composition.

40. A pharmaceutical composition comprising an anti-PD1 antibody of claim 12 and a pharmaceutically acceptable carrier.

41. An anti-PD-1 antibody molecule, wherein said antibody molecule has a heavy chain, wherein the amino acid sequence of said heavy chain consists of the amino acids of SEQ ID NO: 33, and a light chain, wherein the amino acid sequence of said light chain consists of the amino acids of SEQ ID NO:34.

42. A host cell comprising an expression vector comprising a nucleic acid molecule comprising a nucleotide sequence encoding a heavy chain variable domain of an antibody molecule of claim 41, and an expression vector comprising a nucleic acid molecule comprising a nucleotide sequence encoding a light chain variable domain of an antibody molecule of claim 41.

43. The host cell of claim 42, wherein the cell is a mammalian cell.

44. A method of manufacturing an antibody molecule of claim 41 comprising the steps of:
culturing a host cell comprising an expression vector comprising a nucleic acid molecule comprising a nucleotide sequence encoding a heavy chain variable domain of an antibody molecule of claim 41, and an expression vector comprising a nucleic acid molecule comprising a nucleotide sequence encoding a light chain variable domain of an antibody molecule of claim 41 under conditions that allow formation of an antibody molecule according to claim 41; and,
recovering said antibody molecule.

45. The method of claim 44, further comprising the step of purifying said antibody molecule.

46. The method of claim 44, further comprising the step of formulating said antibody molecule into a pharmaceutical composition.

47. A pharmaceutical composition comprising an anti-PD1 antibody of claim 41 and a pharmaceutically acceptable carrier.

48. A method of treating cancer comprising administering to a patient having cancer a therapeutically effective amount of the anti-PD1 antibody molecule of claim 11.

49. The method of claim 48, wherein said cancer is a solid tumor cancer or a cancer of the hematopoietic system.

50. The method of claim 48, wherein the antibody molecule is administered in combination with one or more further therapeutic agents or procedures.

51. The method of claim 50, wherein the one or more further therapeutic agents or procedures is selected from chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, and a cellular immunotherapy.

52. A method of treating cancer comprising administering to a patient having cancer a therapeutically effective amount of the anti-PD1 antibody molecule of claim 12.

53. The method of claim 52, wherein said cancer is a solid tumor cancer or a cancer of the hematopoietic system.

54. The method of claim 52, wherein the antibody molecule is administered in combination with one or more further therapeutic agents or procedures.

55. The method of claim 54, wherein the one or more further therapeutic agents or procedures is selected from chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, and a cellular immunotherapy.

56. A method of treating cancer comprising administering to a patient having cancer a therapeutically effective amount of the anti-PD1 antibody molecule of claim 41.

57. The method of claim 56, wherein said cancer is a solid tumor cancer or a cancer of the hematopoietic system.

58. The method of claim 56, wherein the antibody molecule is administered in combination with one or more further therapeutic agents or procedures.

59. The method of claim 58, wherein the one or more further therapeutic agents or procedures is selected from chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, and a cellular immunotherapy.

60. The anti-PD1 antibody molecule of claim 1 which comprises a human heavy chain constant region selected from the group consisting of IgG1, IgG2, IgG3, and IgG4 constant regions.

61. The anti-PD1 antibody molecule of claim 1, wherein the antibody molecule comprises a human light chain constant region selected from the group consisting of kappa and lambda.

62. An isolated nucleic acid molecule encoding the heavy chain variable domain or the light chain variable domain of an antibody molecule of claim 1.

63. The nucleic acid molecule of claim 62 which has the nucleotide sequence of SEQ ID NO: 75 encoding the heavy chain variable domain comprising the amino acid sequence of SEQ ID NO: 23.

64. The nucleic acid molecule of claim 62 which has the nucleotide sequence of SEQ ID NO: 76 encoding the light chain variable domain comprising the amino acid sequence of SEQ ID NO: 24.

65. An expression vector comprising a nucleic acid molecule comprising a nucleotide sequence encoding the heavy chain variable domain or the light chain variable domain of an antibody molecule of claim 1.

66. The expression vector of claim 65 comprising a nucleic acid molecule comprising the nucleotide sequence of SEQ ID NO: 75 or SEQ ID NO: 76.

67. The expression vector of claim 65, wherein said nucleic acid molecule further comprises a nucleotide sequence encoding heavy chain constant domains or light chain constant domain, respectively, linked to the nucleotide sequence encoding the heavy chain variable domain or the light chain variable domain, respectively.

\* \* \* \* \*